US 6,953,594 B2
Oct. 11, 2005

(12) United States Patent
Lee et al.

(54) METHOD OF PREPARING A POORLY CRYSTALLINE CALCIUM PHOSPHATE AND METHODS OF ITS USE

(75) Inventors: Dosuk D. Lee, Brookline, MA (US); Christian Rey, Aureville (FR); Maria Aiolova, Brookline, MA (US); Aliassghar Tofighi, Belmont, MA (US)

(73) Assignee: Etex Corporation, Cambridge, MA (US)

(*) Notice: Subject to any disclaimer, the term of this patent is extended or adjusted under 35 U.S.C. 154(b) by 79 days.

(21) Appl. No.: 09/993,739

(22) Filed: Nov. 23, 2001

(65) Prior Publication Data

US 2003/0049329 A1 Mar. 13, 2003

Related U.S. Application Data

(63) Continuation of application No. 09/284,297, filed as application No. PCT/US97/18631 on Oct. 16, 1997, which is a continuation of application No. 08/729,016, filed on Oct. 10, 1996, now abandoned, and a continuation of application No. 08/729,344, filed on Oct. 16, 1996, now Pat. No. 6,117,456, and a continuation of application No. 08/729,343, filed on Oct. 16, 1996.

(51) Int. Cl.$^7$ ............................................. A61K 33/42
(52) U.S. Cl. .................. 424/602; 424/422; 424/423; 424/484; 424/603; 428/403; 428/404; 523/115; 523/218; 523/219; 623/16
(58) Field of Search ................... 523/115, 218, 523/219, 116; 428/404, 403; 264/4, 4.7, 4.3, 4.46; 106/690, 691, 696; 623/16; 423/308, 311; 424/484, 602, 603, 423, 426, 422

(56) References Cited

U.S. PATENT DOCUMENTS

| | | | |
|---|---|---|---|
| 4,157,378 A | 6/1979 | Tomlinson et al. | 423/301 |
| 4,429,691 A | 2/1984 | Niwa et al. | 128/92 |

(Continued)

FOREIGN PATENT DOCUMENTS

| | | |
|---|---|---|
| EP | 0 268 463 | 5/1988 |
| EP | 0 347 028 | 11/1989 |

(Continued)

OTHER PUBLICATIONS

Appel et al. "Recent Advances in Implants for Bone Growth Promotion" *Exp. Opin. Ther. Patents* 4:1461 (1994).

(Continued)

Primary Examiner—Neil S. Levy
(74) Attorney, Agent, or Firm—Paul T. Clark; Clark & Elbing LLP

(57) ABSTRACT

The present invention provides a novel process for producing a calcium phosphate cement or filler which hardens in a temperature dependent fashion in association with an endothermic reaction. In the reaction a limited amount of water is mixed with dry calcium phosphate precursors to produce a hydrated precursor paste. Hardening of the paste occurs rapidly at body temperature and is accompanied by the conversion of one or more of the reactants to poorly crystalline apatitic calcium phosphate. The hardened cements, fillers, growth matrices, orthopedic and delivery devices of the invention are rapidly resorbable and stimulate hard tissue growth and healing. A composite material is provided including a strongly bioresorbable, poorly crystalline apatitic calcium phosphate composite and a supplementary material. The supplementary material is in intimate contact with the hydroxyapatite material in an amount effective to impart a selected characteristic to the composite. The supplemental material may be biocompatible, bioresorbable or non-resorbable. A method for treating a bone defect also is provided by identifying a bone site suitable for receiving an implant, and introducing a strongly resorbable, poorly crystalline apatitic calcium phosphate at the implant site, whereby bone is formed at the implant site. The implant site may be a variety of sites, such as a tooth socket, non-union bone, bone prosthesis, an osteoporotic bone, an intervertebral space, an alveolar ridge or a bone fracture.

14 Claims, 20 Drawing Sheets

U.S. PATENT DOCUMENTS

| | | | |
|---|---|---|---|
| 4,440,750 A * | 4/1984 | Glowacki et al. ............. 424/95 |
| 4,612,053 A | 9/1986 | Brown et al. ................. 706/35 |
| 4,684,673 A | 8/1987 | Adachi ....................... 523/116 |
| 4,698,375 A | 10/1987 | Dorman et al. |
| 4,713,076 A | 12/1987 | Draenert et al. |
| 4,722,948 A | 2/1988 | Sanderson et al. |
| 4,737,411 A | 4/1988 | Graves, Jr. et al. ......... 428/403 |
| 4,849,193 A | 7/1989 | Palmer et al. ............... 423/308 |
| 4,880,610 A | 11/1989 | Constantz ................... 423/305 |
| RE33,161 E | 2/1990 | Brown et al. ............... 423/308 |
| 4,917,702 A | 4/1990 | Scheicher et al. ............ 623/16 |
| RE33,221 E | 5/1990 | Brown et al. ............... 423/308 |
| 4,938,938 A | 7/1990 | Ewers et al. ................ 423/308 |
| 4,959,104 A | 9/1990 | Iino et al. ...................... 106/85 |
| 5,007,930 A | 4/1991 | Dorman et al. |
| 5,019,379 A | 5/1991 | Domb et al. |
| 5,034,059 A | 7/1991 | Constantz ................... 106/161 |
| 5,037,639 A | 8/1991 | Tung .......................... 424/57 |
| 5,047,031 A | 9/1991 | Constantz ................... 606/77 |
| 5,049,157 A | 9/1991 | Mittelmeier et al. |
| 5,053,212 A | 10/1991 | Constantz et al. .......... 423/305 |
| 5,085,861 A | 2/1992 | Gerhart et al. ........... 424/78.17 |
| 5,129,905 A | 7/1992 | Constantz ................... 606/76 |
| 5,149,368 A | 9/1992 | Liu et al. ..................... 424/602 |
| 5,152,836 A | 10/1992 | Hirano |
| 5,164,187 A | 11/1992 | Constantz et al. .......... 424/423 |
| 5,178,845 A | 1/1993 | Constantz et al. .......... 423/305 |
| 5,262,166 A | 11/1993 | Liu et al. ..................... 424/423 |
| 5,264,215 A | 11/1993 | Nakabayashi et al. |
| 5,279,831 A | 1/1994 | Constantz et al. .......... 424/423 |
| 5,281,265 A | 1/1994 | Liu ............................. 106/35 |
| 5,286,763 A | 2/1994 | Gerhart et al. ........... 514/772.4 |
| 5,336,264 A | 8/1994 | Constanz et al. ............. 623/16 |
| 5,342,441 A | 8/1994 | Mandai et al. |
| 5,352,715 A | 10/1994 | Wallace et al. |
| 5,427,754 A | 6/1995 | Nagata et al. ............... 423/308 |
| 5,470,803 A | 11/1995 | Bonfield et al. ................ 501/1 |
| 5,496,399 A | 3/1996 | Ison et al. ..................... 106/35 |
| 5,516,532 A | 5/1996 | Atala et al. ................. 424/548 |
| 5,522,893 A | 6/1996 | Chow et al. ................... 623/11 |
| 5,525,148 A | 6/1996 | Chow et al. ................... 106/35 |
| 5,542,973 A | 8/1996 | Chow et al. ................... 106/35 |
| 5,545,254 A | 8/1996 | Chow et al. ................... 106/35 |
| 5,565,502 A | 10/1996 | Glimcher et al. ........... 523/115 |
| 5,605,713 A | 2/1997 | Boltong |
| 5,650,176 A | 7/1997 | Lee et al. ................... 424/602 |
| 5,665,120 A | 9/1997 | Ohtsuka et al. ............... 623/16 |
| 5,676,976 A | 10/1997 | Lee et al. ................... 424/602 |
| 5,683,461 A | 11/1997 | Lee et al. ..................... 623/16 |
| 5,691,397 A | 11/1997 | Glimcher et al. ........... 523/115 |
| 5,700,289 A | 12/1997 | Breitbart et al. ............... 623/16 |
| 5,782,971 A | 7/1998 | Constantz et al. .......... 106/690 |
| 6,027,742 A | 2/2000 | Lee et al. ................... 424/602 |
| 6,117,456 A | 9/2000 | Lee et al. ................... 424/602 |
| 6,132,463 A | 10/2000 | Lee et al. ..................... 623/16 |
| 6,139,578 A | 10/2000 | Lee et al. ................ 623/16.11 |
| 6,201,039 B1 | 3/2001 | Brown et al. |
| 6,214,368 B1 | 4/2001 | Lee et al. ................... 424/423 |
| 6,277,151 B1 | 8/2001 | Lee et al. ................ 623/23.61 |
| 6,287,341 B1 | 9/2001 | Lee et al. ................ 623/16.11 |
| 6,331,312 B1 | 12/2001 | Lee et al. ................... 424/426 |

FOREIGN PATENT DOCUMENTS

| | | |
|---|---|---|
| EP | 0 520 690 | 12/1992 |
| EP | 0664133 | 2/1994 |
| JP | 63111875 | 5/1988 |
| JP | 63170205 | 7/1988 |
| JP | 2-182261 | 7/1990 |
| JP | 5-305134 | 7/1993 |
| JP | 06228011 | 12/1994 |
| JP | 7277712 | 10/1995 |
| WO | WO 92/02453 | 7/1991 |
| WO | WO 92/001009 | 1/1992 |
| WO | WO 94/04657 | 8/1993 |
| WO | WO 94/02412 | 2/1994 |
| WO | WO 94/08458 | 4/1994 |
| WO | WO 94/20064 | 9/1994 |
| WO | WO 95/08319 | 9/1994 |
| WO | WO 94/25080 | 11/1994 |
| WO | WO 96/36562 | 5/1996 |
| WO | WO 97/17285 | 11/1996 |

OTHER PUBLICATIONS

Athanasou et al., "Current Concepts Review Cellular Biology of Bone–Resorbing Cells" *J. Bone and Joint Surg.* 78A:1096–1112 (1996).

Hayes et al., "Augmentation of Cementless Femoral Stems to Improve Initial Stability Using a Remodelable Calcium–Phosphate Bone Material Substitute" *61st Annual American Academy of Orthopedic Surgeons Meeting*, New Orleans (Feb. 1994).

Jang "Advanced Polymer Composites" Chapter 1, Introduction, *The Materials Information Society* 1995.

Norian Corporation, Product Information Sheet, "The Material Science of Norian SRS™, Skeletal Repair System™" 1995.

Rey et al., "Chemical Properties of Poorly Crystalline Apatites" *Phosphorus Res. Bull.* 6:67–70 (1996) abstract only.

Barton, et al., "Surface and Bulk Properties of Amorphous Calcium Phosphate", Colloid Interface Sci., 50th Proceeding Int'l Conf. 3:71(1976) CA:87:73954v.

Besic, et al., "Electron Probe Microanalysis of Noncarious Enamel and Dentin and Calcified Tissues in Mottled Teeth", J. Dent. Res, 48: 131, Jan.–Feb., 1969.

Constanz, et al., "Skeletal Repair by in Situ Formation of the Mineral Phase of Bone", Science, 267:1976, (Mar., 1995).

Driessens, et al., "Calcium Phosphate Bone Cements", Encyclopedic Handbook of Biomaterials and Bioengineering, Wise (Eds) New York, Marcel Dekker, pp 855–877, 1995.

Ducheyne, et al., "Introduction to Bioceramic Composites", Bioceramics, Advanced Series in Ceramics, vol. I.

Eanes, "Thermochemical Studies on Amorphous Calcium Phosphate", Calc. Tiss. Res. 5:133 (1979).

Eanes, et al., "Intermediate Phases in the Basic Solution Preparation of Akaline Earth Phosphates", Calcified Tissue Res. 2(1): 38 (1968).

Eanes, et al., "Intermediate States in the Precipitation of Hydroxyapatite", Nature, 208: 365, (Oct. 1965).

Fukase, et al., "Setting Reactions and Compressive Strengths of Calcium Phosphate Cements", J. Dent. Res 69(12): 1852, (Dec., 1990).

Gao, et al., Established Competence of Bioactive Composite Bone Substitute on the Healing of Diaphyseal Segmental Defects in Sheep, Fifth World Biomaterials Congress, May 29–Jun. 2, 1996, Toronto, Canada.

Glimcher, "Recent Studies of the Mineral Phase in Bone and its Possible Linkage to the Organic Matrix by Protein–Bound Phosphate Bonds", Phil. Trans. R. Soc. Land. B 304: 479 (1984).

Glimcher, et al. "Recent Studies of Bone Mineral is the Amorphous Calcium Phosphate Theory Valid", Journal of Crystal Growth 53:100 (1981).

Graves, et al., "Resorbable Ceramic Implants", J. Biomed, Mater. Res. Symposium 2:91, (1971).

Greenfield, et al., "Formation Chemistry of Amorphous Calcium Phosphates Prepared from Carbonate Containing Solutions", Calc. Tiss. Res. 9: 152 (1972).

Hollinger, et al., "Role of Bone Substitutes", Clinical Orthopaedics and Related Research, 324: 55, (1996).

Horioglu, et al., "Long Term Follow–up of Hydroxyapatte Cement (HAC) Implants for Craniofacial Reconstruction", 21st Annual Meeting of the Society for Biomaterials, Mar. 18–22, 1995, San Francisco, CA.

Ishikawa, et al., "Effects of Preparation Conditions in Aqueous Solution on Properties of Hydroxyapatites",9 (1):58 (1990) [CA 113:21868j].

Kinoshita, et al., Reconstruction of Mandibular Discontinuity Defects in Dogs Using Autogenic Particulate Cancellous Bone and Marrow and Poly (L–lactide) Mesh, Fifth World Biomaterials Congress, May 29–Jun. 2, 1996. Toronto, CA.

Labarthe, et al., "Sur La Structure Et Les Proprietes Des Apatites Carbonatees De Type B Phospho–Calciques," Ann Chem. 8:289, 1973.

Nylen, et al., "Molecular and Ultrastructural Studies of Non–Crystalline Calcium Phosphates", Calc. Tiss. Res. 9:95, 1972.

Otsuka, et al., "Effect of Particle Size of Metastable Calcium Phosphates on Mechanical Strength of a Novel Self–Setting Bioactive Calcium Phosphate Cement", Journal of Biomedical Materials Research, 29:25 (1995).

Pool, "Coral Chemistry Leads to Human Bone Repair", Science 269:1772 (Mar., 1995).

Posner, et al., "Synthetic Amorphous Calcium Phosphate and its Relation to Bone Mineral Structure", Bone Mineral Structure,8:273 (1975).

Rey, et al., "Preparation of Microporous Ceramic at Low Temperature From Poorly Crystalline Apatite", Symposium Abstract, 1993.

Rey, et al., "Structural Studies of the Mineral Phase of Calcifying Cartilage", J. Bone Min. Res. 6:515, 1991.

Rey, et al., The Carbonate Environment in Bone Mineral: A Resolution–Enhanced Fourier Transform Infrared Spectroscopy Study, Cal. Tissue Int. 45:157–164, 1989.

Termine, et al., "Amorphous/Crystalline Interrelationships in Bone Mineral", Calc. Tissue. Res.1:8 1995.

Tung, et al., "An Intermediate State in Hydrolysis of Amorphous Calcium Phosphate", Calc. Tissue Int. 35:784, 1983.

Yasue, et al., Effect of Adsorption of Succine Acid on the Formation of Amorphous Calcium Phosphate, International Edition, 102(12):1122(1994).

Gao, T.J. "Established competence of Bioactive Composite Bone Substitute on the Healing of Diaphyseal Segmental Defects in Sheep," Fifth World Biomaterials Congress, May 29–Jun. 2, Toronto, Canada. 1995.

Glimcher et al., "Recent studies of the mineral phase in bone and its possible linkage to the organic matrix by protein–bound phosphate bonds", Phil. Trans. R. Soc. Lond., B 304:479–508, 1984.

Glimcher et al., "Recent Studies of Bone Mineral: Is the Amorphous Calcium Phosphate Theory Valid?" J. Crystal Growth, 53: 100–119 (1981).

Graves et al., "Resorbable Ceramic Implants", J. Biomed. Mater. Res. Symposium, No. 2 (Part 1), pp. 91–115 (1971).

Greenfield et al., "Formation chemistry of amorphous calcium phosphates prepared from carbonate containing solutions", Calc. Tiss. Res., 9:152 (1972).

Hirasawa et al., "Manufacture of high purity hydroxyapatite," Chemical Abstracts, 108 (10), p. 166, No. 78193h (Mar. 7, 1988).

Holmes et al., "Surface areas by gas adsorption on amorphous calcium phosphate and crystalline hydroxyapatite", Calc. Tiss. Res., 7:163 (1971).

Ishikawa et al., "Effects of preparation in aqueous solution on properties of hydroxyapatites", Dent. Mater. J. 9(1):58 (1990) [CA 113:218168j] (Abstract).

Jones et al., "Poly [L–Lactide] and Poly [L–Lactide] Ceramic Filled Composites: A Long Term in vivo/in vitro Degradation Study," Fifth World Biomaterials Congress, May 29–Jun. 2, 1996, Toronto, Canada.

Kamei et al., "Implantation of hydroxyapatite–bonded polymer," Fifth World Biomaterials Congress, May 29–Jun. 2, 1996, Toronto, Canada.

Kim et al., "Hyaluronan Based Biodegradable Scaffolds for Skeletal Tissue Reconstruction," Fifth World Biomaterials Congress, May 29–Jun. 2, 1996, Toronto, Canada.

Kinoshita et al., "Reconstruction of Mandibular Discontinuity Defects in Dogs using Autogenic Particulate Cancellous Bone and Marrow and Poly(L–lactide) mesh," Fifth World Biomaterials Congress, May 29–Jun. 2, 1996, Toronto, Canada.

Labarthe et al., "Sur la structure et les properiétés des apatites carbonatées de type B phospho–calciques", Ann. Chem., 8:289 (1973).

Ladizesky et al., "Hydrostatic Extrusion of Hydroxyapatite Polyethylene Composite", Fifth World Biomaterials Congress, May 29–Jun. 2, 1996, Toronto, Canada.

Liu et al., "Nano–Apatite/Polymer Composites II. Surface Modification of Nano–Apatite by Grafting of Polyethylene Glycol," Fifth World Biomaterials Congress, May 29–Jun. 2, 1996, Toronto, Canada.

Nylen et al., "Molecular and ultrastructural studies of non–crystalline calcium phosphates" Calc. Tiss. Res., 9:95 (1972).

Oka et al., "Development of Artificial Osteo–Chondral Composite Material," Fifth World Biomaterials Congress, May 29–Jun. 2, 1996, Toronto, Canada.

Otsuka et al., "Effect of particle size of metastable calcium phosphates on mechanical strength of a novel self–setting bioactive calcium phosphate", J. Biomed Mat. Res., 29:25 (1995).

Pool, "Coral chemistry leads to human bone repair", Science, 269:1772 (Mar., 1995).

Posner et al., "Synthetic amorphous calcium phsophate and its relation to bone mineral structure", Bone Mineral Structure, 8:273–281 (1975).

Rey et al., "The carbonate environment in bone mineral: a resolution–enhanced fourier transform infared spectroscopy study", Calcif. Tissue Int., 45:157 (1989).

Rey et al., "Structural studies of the mineral phase of calcifying cartilage", J. Bone Min. Res., 6:515 (1991).

Rey et al., "Preparation of Microporous Ceramic at Low Temperature from Poorly Crystalline Apatite", Symposium Abstract, 1993.

Rizkalla et al., "Effect of Composition on Strength of Bioactive Composites," Fifth World Biomaterials Congress, May 29–Jun. 2, 1996, Toronto, Canada.

Saifullin, R.S., "Physical Chemistry of Inorganic Polymeric and Composite Materials", Chapter 1: Introduction, Ellis Horwood, New York.

Selmani et al., "Bioerodible Polyester Foams for Orthopaedic Tissue Culture," Fifth World Biomaterials Congress, May 29–Jun. 2, 1996, Toronto, Canada.

Termine et al., "Amorphous/Crystalline Interrelationships in Bone Mineral", Calc. Tiss. Res. 1, 8–23 (1967).

Törmälä, P., "Biodegradable Self–Reinforced Composite Materials; Manufacturing Structure and Mechanical Properties", Clinical Materials 10:29–34 (1992).

Tung et al., "An intermediate state in hydrolysis of amorphous calcium phosphate", Calcif. Tissue Int., 35:783 (1983).

Boskey, Adele I., "Matrix Proteins and Mineralization: An Overview", *Connect. Tiss. Res.*, 35, (1–4):357–363 (1997).

Butterman, et al., "The use of bone allografts in the spine", *Clinic, Orthoped. Rel. Res.*, 324: 75 (1996).

Crowley, et al., "Prosthesis for primary total hip replacement", *Int'l. J. Technol. Assess. Health Care*, 11(4): 770 (1995).

Denissen et al., "Net–shaped hydroxyapatite implants for release of agents modulating periodontal–like tissues", *J. Periodontal Res.*, 32:40–46 (1997).

Ducheyne, et al., "Adavanced Series in Ceramics, vol. 1,;Introduction to Bioceramic Composites", *L. Hench and J. Wilson, Eds World Scientific* New Jersey.

Friis, et al., "Fracture Toughness of Surface–Treated Carbon Fiber Reinforced Composite Bone Cement", *Fifth World Biomaterials Congress*, Toronto, Canada May 29–Jun. 2, 1996.

Hubbell, "Biomaterials in tissue engineering", Bio/technology, 13:56, (1995).

Thissen et al., "Surface modification of bioresorbable polymers by plasma induced graft polymerization", *Fifth World Biomaterials Congress*, Toronto, Canada May 29–Jun. 2, 1996.

* cited by examiner

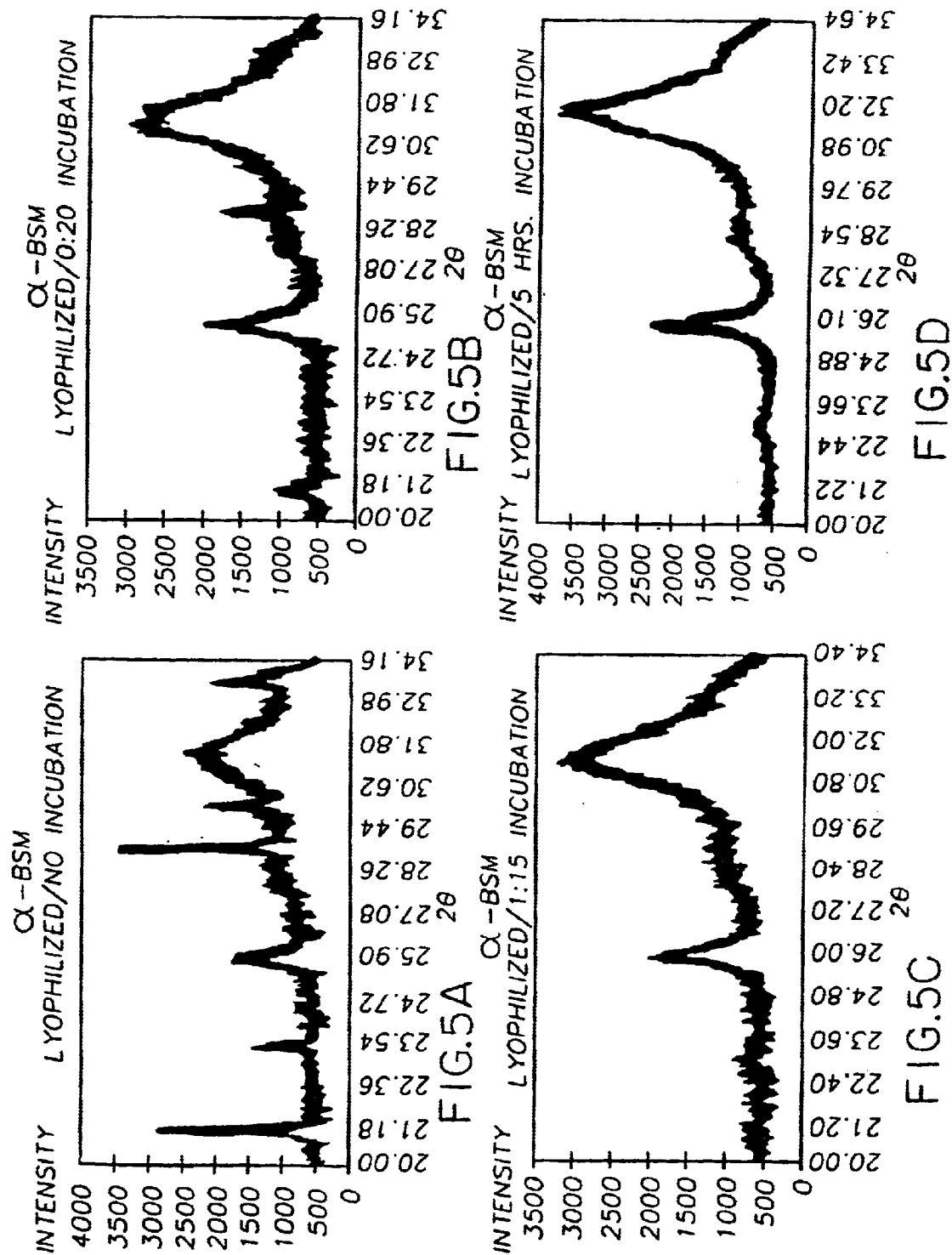

FIG.19A
FIG.19B
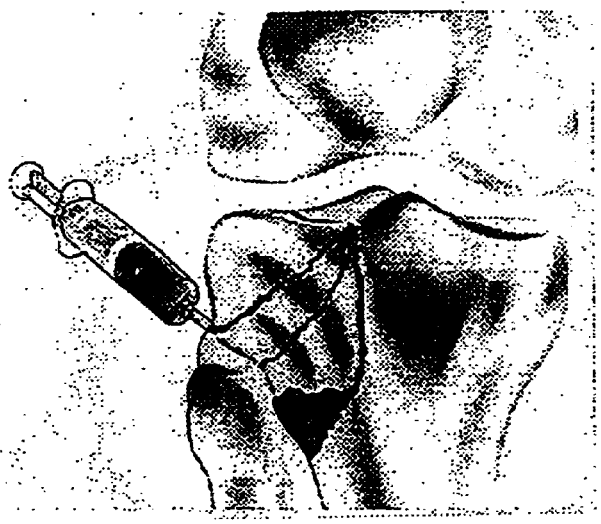
FIG. 20
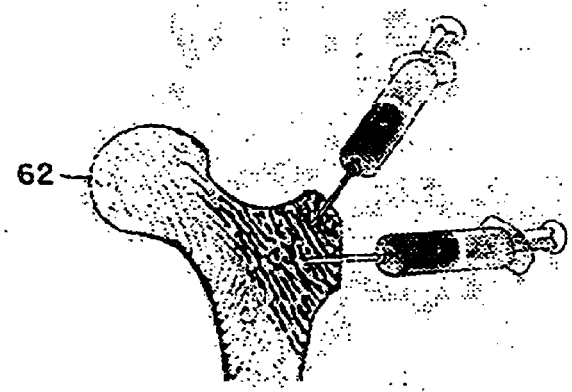
FIG.21A
FIG.21B
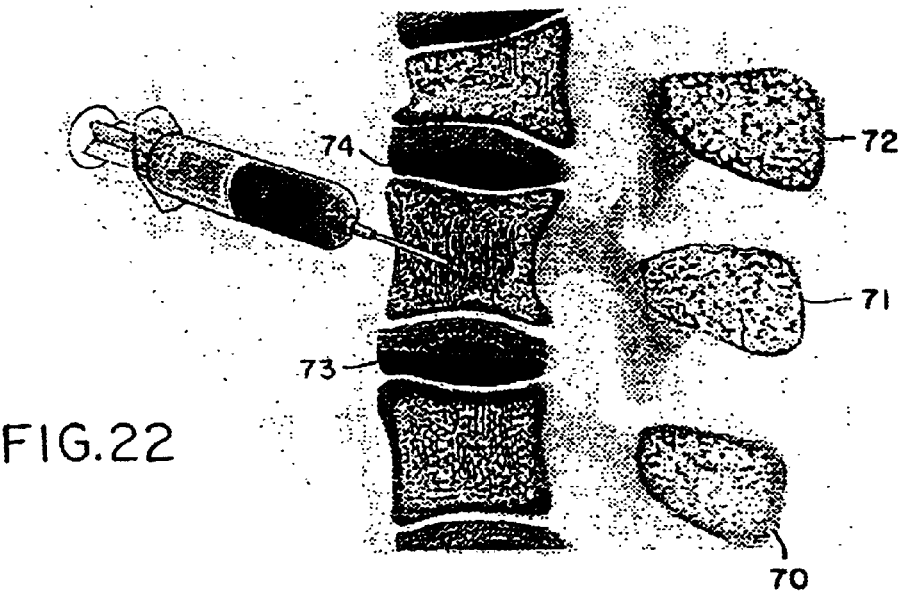
FIG.22

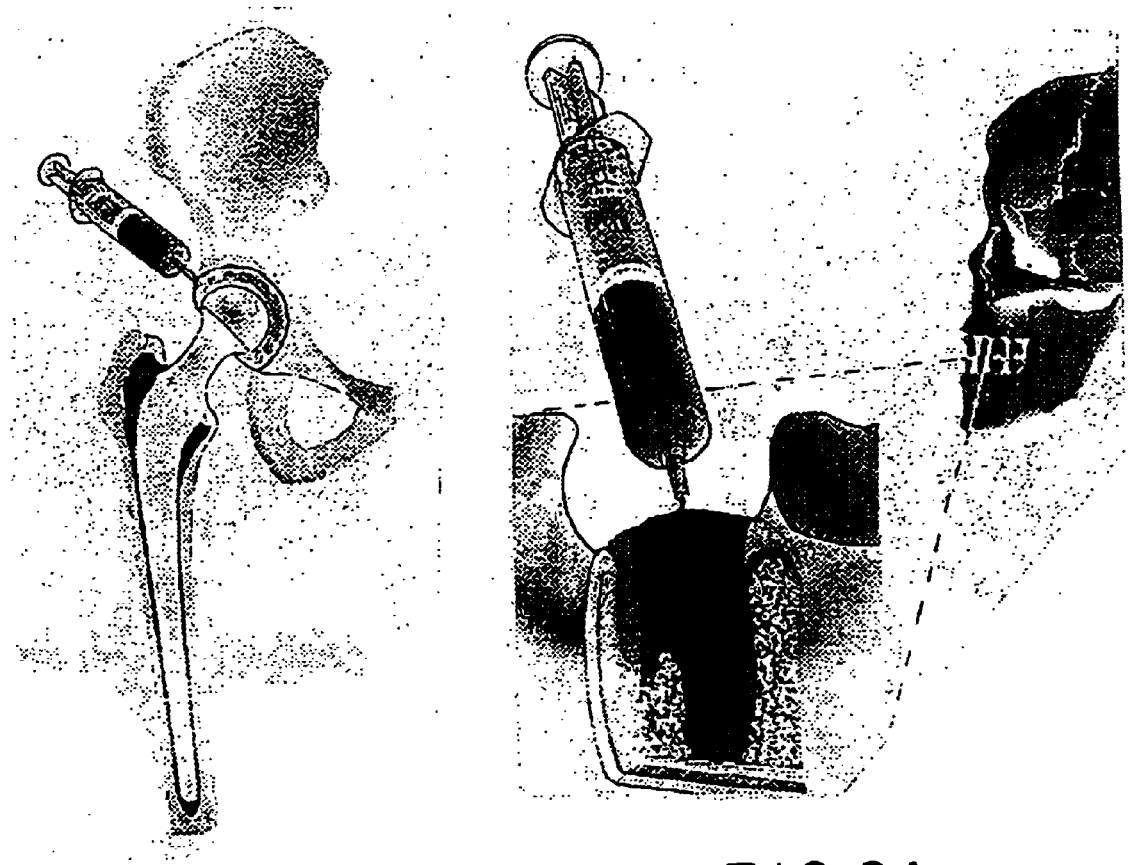
FIG. 23
FIG. 24
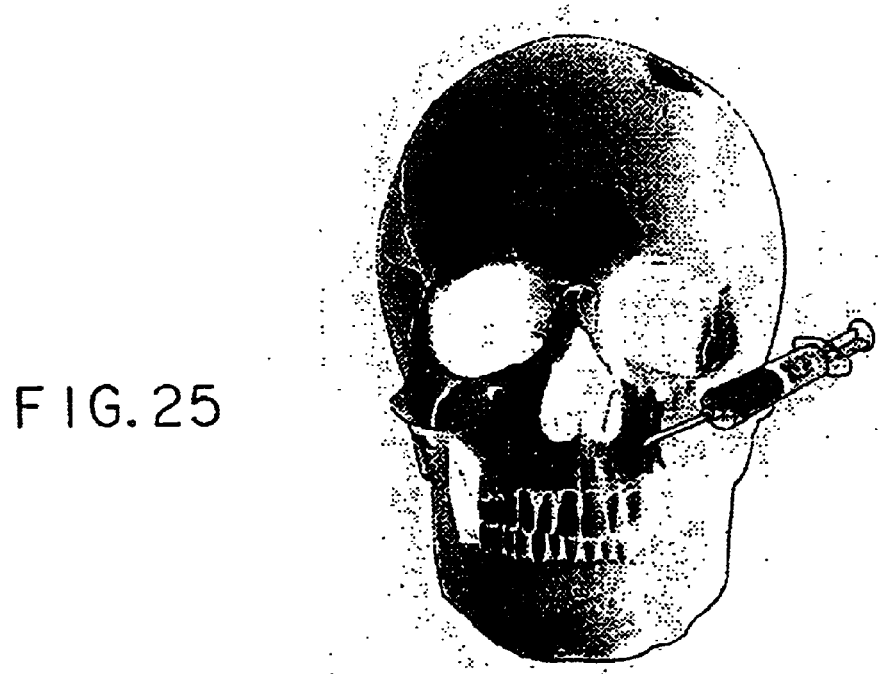
FIG. 25

METHOD OF PREPARING A POORLY CRYSTALLINE CALCIUM PHOSPHATE AND METHODS OF ITS USE

RELATED APPLICATIONS

This application is a continuation application of co-pending application U.S. application Ser. No. 09/284,297, filed Jul. 5, 2000, which is a §371 application of International Application No. PCT/US97/18631, filed Oct. 16, 1997 which claims priority to U.S. application Ser. Nos. 08/729,016, abandoned 08/729,344 now U.S. Pat. No. 6,117,456 and 08/729,343 pending and all filed on Oct. 16, 1996.

FIELD OF THE INVENTION

This invention relates to hard tissue implant materials containing poorly crystalline apatitic calcium phosphate useful as human or animal implantable bioceramics for use in orthopedic and dental applications and for other purposes. The invention further relates to bioresorbable composites, cell therapy and therapeutic substance delivery devices useful in human and animal therapeutics.

BACKGROUND OF THE INVENTION

Calcium phosphates are the principal constituent of hard tissues (bone, cartilage, tooth enamel and dentine). Calcium phosphates generally occur in apatitic form when found in biological tissues. For instance, the composition of bone mineral may be represented by the following formula:

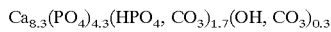

$$Ca_{8.3}(PO_4)_{4.3}(HPO_4, CO_3)_{1.7}(OH, CO_3)_{0.3}$$

Unlike the ideal stoichiometric crystalline hydroxyapatite $(Ca_{10}(PO_4)_6(OH)_2)$, or stoichiometric apatites in general $(Ca_5(PO_4)_3X)$, which have a calcium to phosphate ratio (Ca/P) of 1.67, bone mineral is a non-stiochiometric apatite. Its non-stoichiometry is primarily due to the presence of divalent ions, such as $CO_3^{2-}$ and $HPO_4^{2-}$, which are substituted for the trivalent $PO_4^{3-}$ ions. Substitution by $HPO_4^{2-}$ and $CO_3^{2-}$ ions produces a change of the Ca/P ratio, resulting in Ca/P ratio which may vary between 1.50 to 1.70, depending on the age and bony site. Generally, the Ca/P ratio increases during aging of bone, suggesting that the amount of carbonate species increases for older bones. Naturally-occurring bone mineral is made of nanometer-sized, poorly-crystalline calcium phosphate with apatitic structure. The poorly crystalline apatitic calcium phosphate of bone is distinguished from the more crystalline hydroxyapatites and non-stoichiometric hydroxyapatites by its distinctive XRD pattern as shown in FIG. 7. It is the Ca/P ratio in conjunction with nanocrystalline size and the poorly-crystalline nature that yields the specific solubility properties of the bone minerals. And because bone tissues undergo constant tissue repair regulated by mineral-resorbing cells (Osteoclasts) and mineral-producing cells (Osteoblasts), solubility behavior of minerals is important in maintaining a delicate metabolic balance between these cell activities.

Synthetic bone graft material made to closely resemble natural bone minerals can be a useful replacement for natural bone. Acceptable synthetic bone can avoid the problem of availability and harvesting of autologous bone (patient's own bone) and the risks and complications associated with allograft bone (bone from a cadaver), such as risks of viral transmission. An ideal synthetic bone graft should possess a minimum of the following four properties: (1) it should be chemically biocompatible; (2) it should provide some degree of structural integrity in order to keep the graft in place and intact until the patient's own bone heals around it; (3) it should be resorbable so that the patient's own bone ultimately replaces the graft; and, (4) because it may be necessary to incorporate cells and/or biomolecules into the synthetic bone material, it is desirable that the process used to form the material employ low temperatures and chemically mild conditions. Similar criteria are also important for other hard tissue grafts (e.g. cartilage).

These criteria may be met by a material in which parameters, such as Ca/P ratios, crystal size, crystallinity, porosity, density, thermal stability and material purity are controlled. While there have been considerable efforts to synthesize a ceramic material for use as implants, synthetic hydroxyapatites have most often been used because their chemical formulae are very similar to the naturally occurring mineral in bone. LeGeros R. Z., in Calcium Phosphates in Oral Biology and Medicine, Karger Pub. Co., New York, 1991 teaches highly crystalline forms of hydroxyapatite produced by solution precipitation followed by sintering at high temperatures (800–1200° C.). High temperature treatment yields highly stoichiometric hydroxyapatite with crystal sizes on the order of several microns with a Ca/P of 1.67. Such highly crystalline hydroxyapatite is essentially non-resorbable in vivo. It is not replaced by living bone tissue and remains intact in the patient for an undesirably extended period of time.

A number of other approaches to the production of bone substitute material have employed hydroxyapatite produced by a solid-state acid-base reaction of primarily crystalline calcium phosphate reactants. These hydroxyapatite bone substitute materials are sometimes poorly-reacted, inhomogeneous, and have significant crystalline hydroxyapatite content.

Constantz in U.S. Pat. No. 4,880,610 reports on the preparation of calcium phosphate minerals by the reaction of a highly concentrated phosphoric acid with a calcium source in the presence of a base and hydroxyapatite crystals. The resultant product is a polycrystalline material containing a crystalline form of hydroxyapatite minerals. Likewise, U.S. Pat. No. 5,053,212 to Constantz et al. discloses the use of a powdered acid source to improve the workability and mixability of the acid/base mixture; however, a mixed-phase calcium phosphate material similar to that of U.S. Pat. No. 4,880,610 is reported. Recently, Constantz et al. reported in Science (Vol. 267, pp. 1796–9 (Mar. 24, 1995)) the formation of a carbonated apatite from the reaction of monocalcium phosphate monohydrate, β-tricalcium phosphate, α-tricalcium phosphate, and calcium carbonate in a sodium phosphate solution, to provide a calcium phosphate material which is still substantially more crystalline in character than naturally occurring bone minerals.

Similarly, Brown et al. in U.S. Pat. Reissue No. 33,221 report on the reaction of crystalline tetracalcium phosphate (Ca/P of 2.0) with acidic calcium phosphates. Liu et al. in U.S. Pat. No. 5,149,368 disclose the reaction of crystalline calcium phosphate salts with an acidic citrate.

A number of calcium phosphate bone fillers and cements have been described as "resorbable." Generally, these are compounds comprising or derived from tricalcium phosphate, tetracalcium phosphate or hydroxyapatite. At best these materials may be considered only weakly resorbable. Of these, the tricalcium phosphate compounds have been demonstrated to be the most resorbable and after many years of study they are still not widely used in clinical settings. The tricalcium phosphates are known to have lengthy and somewhat unpredictable resorption profiles, generally requiring in excess of one year for resorption. Furthermore, unless steps are taken to produce extremely porous or channeled samples, the tricalcium phosphates are not replaced by bone. Recently it has been concluded that the "biodegradation of TCP, which is higher than that of Hap [hydroxyapatite] is not sufficient" (Berger et al., Biomaterials, 16:1241 (1995)). Tetracalcium phosphate and hydroxyapatite derived compounds are also only weakly resorbable. Tetracalcium phosphate fillers generally exhibit partial resorption over long periods of time such as 80% resorption after 30 months (Horioglu et al., Soc. for Biomaterials, March 18–22, pg 198 (1995)). Approximately 30% of microcrystalline hydroxyapatite implanted into the frontal sinus remained after 18 months in cats.

All of these references disclose a chemical reaction resulting in crystalline form of hydroxyapatite solids that has been obtained by reacting crystalline solids of calcium phosphate. There has been little reported on the use of amorphous calcium phosphates (Ca/P of approximately 1.5) as one of the reactants because the amorphous calcium phosphates are the least understood solids among the calcium phosphates and amorphous calcium phosphate has traditionally been considered to be a relatively inert and non-reactive solid.

Amorphous calcium phosphate material has been used as a direct precursor to the formation of a highly crystalline hydroxyapatite compounds under generally high temperature treatments. Such a highly crystalline material is inappropriate for synthetic bone because it is highly insoluble under physiological conditions. Chow et al. in U.S. Pat. No. 5,525,148 report the testing of ACP precursors in a number of reaction schemes but states that slurries of a variety of crystalline calcium phosphates including ACP either alone or in mixtures do not produce a setting cement or act as an effective remineralizing agent.

Brown et al. in U.S. Pat. Reissue No. 33,221 report on the formation of crystalline hydroxyapatite for dental cement by reacting an amorphous phase specifically restricted to tetracalcium phosphate (Ca/P of 2.0) with at least one of the more acidic calcium phosphates. Further, Brown et al., does not disclose the preparation or the properties of such a tetracalcium phosphate in amorphous state. Tung in U.S. Pat. No. 5,037,639 discloses the use and application of standard amorphous calcium phosphate paste for the remineralization of teeth. Tung proposes the use of standard inert amorphous calcium phosphate mixed with and delivered through a chewing gum, mouth rinse or toothpaste, which upon entering oral fluids converts to crystalline fluoride containing hydroxyapatite which is useful to remineralize tooth enamel. Simkiss in PCT/GB93/01519 describes the use of inhibitors, such as Mg ions or pyrophosphate, mixed with amorphous calcium phosphate and implanted into living tissues. Upon leaching of, for example Mg ions, into surrounding bodily fluids, the amorphous calcium-magnesium phosphate converts into a more crystalline form.

There remains a need to develop new synthetic materials that more closely mimic the properties of naturally-occurring minerals in hard tissue. In particular, there remains a need to provide synthetic bone materials which are completely bioresorbable, which can be formed at low temperatures and are poorly-crystalline, with nanometer-sized crystals.

SUMMARY OF THE INVENTION

The present invention provides a bioactive ceramic material that is biocompatible, bioresorbable and workable for long period of time at room temperature. The bioactive ceramic material may be formed at low temperatures, is readily formable and/or injectable, and yet can harden to high strength upon further reaction. The bioactive ceramic material contains poorly crystalline apatitic calcium phosphate solids with Ca/P ratios comparable to naturally occurring bone minerals and having stiffness and fracture toughness similar to natural bone. The bioactive ceramic composite material is strongly bioresorbable and its biosorbability and reactivity can be adjusted to meet the demands of the particular therapy and/or implant site. The material may be prepared as bone plates, bone screws and other fixtures and medical devices, including veterinarian applications, which are strongly bioresorbable and/or ossifying.

These and other features of the invention are accomplished by a self-hardening bioceramic composition, including a hydrated precursor of a calcium phosphate and an aqueous-based liquid in an amount sufficient to hydrate the calcium phosphate to form a paste or putty, characterized in that hardening of the hydrated precursor is associated with an endothermic setting reaction. Alternatively, a self-hardening bioceramic composition, includes a hydrated precursor of an amorphous calcium phosphate and an aqueous-based liquid in an amount sufficient to hydrate the calcium phosphate to form a paste or putty, characterized in that hardening of the hydrated precursor occurs in more than ten minutes.

In another aspect of the invention, a bioceramic composition is provided including a poorly crystalline calcium phosphate prepared by promoting the hardening of a hydrated precursor comprising an amorphous calcium phosphate and an aqueous-based liquid in an amount sufficient to hydrate the amorphous calcium phosphate to form a paste or putty, whereby hardening is associated with an endothermic reaction and the conversion of the amorphous calcium phosphate into the poorly crystalline calcium phosphate.

The bioceramic composition of the invention may be prepared by mixing in any order, (a) an amorphous calcium phosphate, (b) a promoter, and (c) an aqueous-based liquid in an amount sufficient to form a paste or putty, whereby the paste or putty is converted into a poorly crystalline apatitic calcium phosphate and said conversion is associated with hardening of the paste in an endothermic reaction.

Definitions

"Amorphous"—By "amorphous" as that term is used here, it is meant a material with significant amorphous character. Significant amorphous character contemplates greater than 75% amorphous content, preferably greater than 90% amorphous content, and is characterized by a broad, featureless X-ray diffraction pattern. It is recognized that a small degree of crystallinity may exist in the material. However, for the amorphous precursor materials of the present invention, it is preferable that the degree of crystallinity be less than that desired in the product material.

"Bioactive"—"Bioactive" refers to a material that induces hard tissue formation in and about the implant. When implanted in soft tissue, the bioactivity may also require the presence of a growth or trophic factor, or the seeding of the implant with a hard tissue forming cell type.

"Biocompatible"—The term "biocompatible", as used herein, means that the material does not elicit a substantial detrimental response in the host. There is always concern, when a foreign object is introduced into a living body, that the object will induce an immune reaction, such as an inflammatory response that will have negative effects on the host. For example, although hydroxyapatite is generally considered to be "biocompatible", significant inflammation and tissue necrosis have been observed when crystalline hydroxyapatite microcarriers are inserted intramuscularly in animals (see, for example, Ijntema et al., *Int. J. Pharm* 112:215 (1994)).

"Bioresorbable"—"Bioresorbable" refers to the ability of a material to be resorbed in vivo. "Full" resorption means that no significant extracellular fragments remain. The resorption process involves elimination of the original implant materials through the action of body fluids, enzymes or cells. Resorbed calcium phosphate may, for example, be redeposited as bone mineral, or by being otherwise reutilized within the body, or excreted. "Strongly bioresorbable", as that term is used herein, means that at least 80%, preferably 95–99% and most preferably >99%, of the total mass of material implanted intramuscularly or subcutaneously is resorbed within one year. In preferred embodiments of the invention, the strongly resorbing poorly crystalline apatitic (PCA) calcium phosphate is characterized in that, when at least 1 g (preferably 1–5 g) of PCA material is implanted at a subcutaneous or intramuscular site, at least 80% of the material is resorbed w/in one year. In more preferred embodiments, the material will be resorbed within nine months, six months, three months, and ideally one month. Furthermore, particularly preferred materials are characterized in that they can be fully resorbed in the stated time periods. For the purpose of this disclosure, "weakly" resorbable means that less than 80% of the starting material is resorbed after one year.

"Effective amount"—An effective amount of a supplemental material is an amount sufficient to impart the desired mechanical or chemical property to the composite.

"Hardening"—"Hardening" refers to the process by which the hydrated precursor is transformed into a hardened PCA material. The PCA material is considered to be "hardened" when it is a substantially non-formable solid. Such a hardened PCA material has minimal compressibility and tends to undergo plastic as opposed to elastic deformation.

"Hydrated precursor"—The term "hydrated precursor", as used herein, refers to the paste or putty formed by hydration of the dry precursors in the presence of a limited amount of aqueous solution (i.e., less than approximately 1 mL aqueous solution/1 g precursor powder). The hydrated precursor may comprise both reactants and products, in various combinations, depending on the extent to which the conversion has progressed. Both the "injectable" and "formable" precursor pastes described herein are hydrated precursors. Preferred "injectable" hydrated precursors have a consistency appropriate for delivery through an 18 gauge needle.

"Poorly crystalline apatitic calcium phosphate", "PCA calcium phosphate" and "PCA material", as those terms are used herein, describe a synthetic poorly crystalline apatitic calcium phosphate. The PCA material is not necessarily restricted to a single calcium phosphate phase provided it has the characteristic XRD and FTIR pattern. A PCA calcium phosphate has substantially the same X-ray diffraction spectrum as bone. The spectrum is generally characterized by only two broad peaks in the region of 20–35° with one centered at 26° and the other centered at 32°. It is further characterized by FTIR peaks at 563 $cm^{31\ 1}$, 1034 $cm^{-1}$, 1638 $cm^{-1}$ and 3432 $cm^{-1}$ (±2 $cm^{-1}$). Sharp shoulders are observed at 603 $cm^{-1}$ and 875 $cm^{-1}$, with a doublet having maxima at 1422 $cm^{-1}$ and 1457 $cm^{-1}$.

"Promoter"—The term "promoter", as used herein, describes a material or treatment that promotes hardening of a hydrated precursor and may enhance the ACP to PCA calcium phosphate conversion. Some promoters participate in the conversion and are incorporated into the product PCA material; others, known as "passive" promoters, do not participate.

"Reactive"—"Reactive" is used herein to refer to the ability of an amorphous calcium phosphate when mixed with liquid to form a hydrated precursor to undergo conversion to the PCA material of the present invention in the presence of a promoter in association with hardening of the precursor materials. Preferred ACPs are characterized by an ability to convert completely, an ability to convert quickly with hardening, an ability to undergo conversion with otherwise inert compounds and/or an ability to convert into a substantially homogeneous PCA material. Where the ACP is reacted with a second calcium phosphate, the "conversion" can encompass conversion of both the ACP and the second calcium phosphate. The degree of hardening and the kinetics of the hardening process are also important elements of reactivity. Some ACPs are more reactive than others. An ACP is considered "highly reactive" if it undergoes conversion and hardening to a PCA material in the presence of a weak promoter, such as dicalcium phosphate dihydrate ("DCPD") with a grain size distribution containing a significant fraction of grains greater than 100 $\mu$m. Preferred highly reactive ACPs produce a hardened PCA material in the presence of weakly promoting DCPD and water at 37° C. in less than twelve hours, with hardening being substantially complete in about one to five hours, and ideally 10–30 minutes.

BRIEF DESCRIPTION OF THE DRAWING

FIGS. 5a–d are X-ray diffraction patterns tracking the progress of the reaction of a mixture of reactive amorphous calcium phosphate and dicalcium diphosphate to form a PCA material of the present invention;

FIG. 9 presents photomicrographs of tibial defects either untreated (9a) or treated (9b) with a delivery vehicle of the present invention.

FIG. 19 is a pictorial illustration of an implant of the invention introduced into a non-union bone site;

FIG. 20 is a pictorial illustration of an implant of the invention introduced into a fragmented bone site;

FIG. 21 is a pictorial illustration of an implant introduced by syringe into a osteoporotic bone site;

FIG. 22 is a pictorial illustration of an implant introduced by syringe into a osteoporotic vertebrae;

FIG. 23 is a pictorial illustration of an implant of the invention used as a bone cement to secure a hip prosthesis;

FIG. 24 is a pictorial illustration of an implant of the invention introduced into a tooth socket;

FIG. 25 is a pictorial illustration of an implant of the invention introduced into an alveolar ridge;

DETAILED DESCRIPTION OF THE INVENTION

Figure 1:
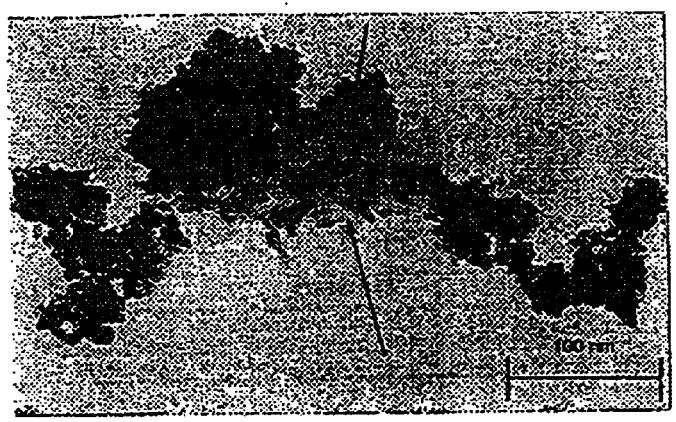
FIG. 1 is a high-resolution transmission electron micrograph of the reactive amorphous calcium phosphate illustrating the nanometer-sized grains in clusters with relatively unclear boundaries and partially immersed in shapeless form (arrows)

The present invention is directed to biocompatible ceramic compositions adapted for use in the repair and growth promotion of hard tissue including the fabrication of resorbable orthopedic and dental fixtures. The compositions comprise a biocompatible and highly bioresorbable poorly crystalline apatitic calcium phosphate (PCA calcium phosphate) sometimes combined with a suitable biocompatible matrix or additive. The PCA calcium phosphate has utility in dental, orthopedic, drug delivery, cell therapy and other therapeutic applications.

The inventive composition may be applied as a bone cement to the bone-contacting surfaces of prosthetic devices. It may be applied directly to bone defects as a filler, where it is capable of promoting the growth of new bone tissue. The composition may similarly be applied for repair, growth or production of cartilaginous tissue. Alternatively, the composition may be used to fabricate fixtures or devices such as screws and plates, which under appropriate circumstances will be resorbed and replaced by bone or cartilage. The composition may also be used free standing in soft tissue. When a pharmaceutically active agent is added to the composition, it serves as a drug delivery device, and release of the agent may occur over an extended time period after implantation as the composition slowly biodegrades.

The invention also provides methods for promoting the conversion of ACP to PCA calcium phosphate, in a controlled fashion, in the form of a paste or putty which hardens predictably.

The PCA calcium phosphate bioceramic of the invention is generally calcium deficient with a calcium to phosphate ratio of less than 1.5 as compared to the ideal stoichiometric value of approximately 1.67 for hydroxyapatite. They are further characterized by their biological bioresorbability and minimal crystallinity. They may be rapidly bioresorbable and possess high porosity and/or low density or slowly bioresorbable and possess decreased porosity and/or high density. Their crystalline character is substantially the same as natural bone without the higher degree of crystallinity seen in the bone substitute materials known to the art. The inventive PCA calcium phosphate also is biocompatible, that is, there is no significant detrimental reaction (e.g., inflammation or fibrosis) induced in the host by the implanted material. Materials which induce a medically acceptable level of inflammation or fibrosis are considered biocompatible. The PCA calcium phosphate may be used in a moist precursor form (i.e., hydrated precursor) and applied as a cement directly to a surgical site such as a fracture, or it may be hardened ex vivo and subsequently implanted.

The resorbability of the inventive PCA calcium phosphate is attributable to a combination of density, porosity, chemical composition and crystalline structure. Low crystallinity in apatites is associated with somewhat increased solubility in aqueous systems compared to other more crystalline species, and thus the low crystallinity and/or presence of stable amorphous apatitic domains in the inventive PCA calcium phosphate is believed to be associated with its resorbability in biological systems. Porosity facilitates both the penetration of cells and cell processes into the bioceramic matrix and the diffusion of substances to and from the matrix interior. Accordingly, PCA calcium phosphate compositions of lower porosity resorb more slowly in vivo than those of high porosity. In one embodiment, the use of controlled particle size reactants leads to a PCA calcium phosphate material of controlled porosity. Other methods of promoting porosity may be employed, such as chemical or physical etching and leaching.

The inventive PCA calcium phosphates may be manufactured with a variety of resorption rates ranging from slow resorption times of greater than one year (typical of weakly resorbing hydroxyapatites bone fillers and bone substitutes known to the art) to resorption rates as fast as several grams, e.g., 1–5 g, in 1 to 2 months. Thus depending upon the density, porosity, reactants used, final crystallinity of the reaction product, and the amount of crystallization inhibitors used, formulations can be prepared in which a one gram device will fully resorb in any desired time period—from 2 weeks to 1, 3 or 6 months to 1, 2 or three years. A strongly resorbable PCA calcium phosphate of the instant invention possesses an in vivo resorption rate in which 80% (preferably 95–99% and more preferably >99%) or more of at least one gram (preferably 1–5 g) of starting material is resorbed within one year, preferably within 6 months, more preferably in less than 3 months, and most preferable within 1–2 months.

For the production of new bone in load bearing situations it has been found that preparations which are fully resorbed and replaced by bone in about six to eight weeks lead to histologically normal bone by 12 weeks. In some load bearing situations it may be desirable to have resorption occur more slowly. Additionally, when hard tissue is being prepared ectopically or the shape of an existing hard tissue is to be augmented, it may be desirable to employ more slowly resorbing PCA calcium phosphate.

Adjustment of the density or porosity of the resultant PCA calcium phosphate or the use of reaction parameters which affect the speed and hardness of setting are all useful approaches to varying the in vivo resorption time of the inventive PCA calcium phosphate. These parameters may be adjusted alone or in combination as required by specific applications.

Slow resorption (greater than three months) is favored by the use of high density, low porosity PCA calcium phosphate and/or rapid reaction and hardening times. Fast resorption (three or less months) is favored by the use of low density, high porosity PCA calcium phosphate, and/or slow reaction and setting times. Guidance for adjustment of rate and completeness of reaction to form the PCA calcium phosphate are given elsewhere herein. The following describes the production of preferred PCA calcium phosphate precursors which lead to a hardened PCA calcium phosphate cements of differing resorbability kinetics in vivo.

A rapidly resorbing PCA calcium phosphate is obtained by conversion of the highly reactive ACP of Example 5 using a DCPD with a grain size distribution having a considerable content of grain sizes greater that 100 $\mu$m (e.g. corresponding to distribution B1 in Table 3) as a promoter. The powders are prepared as a hydrated precursor as described in Example 8.

A slowly resorbing PCA calcium phosphate is obtained by conversion of the highly reactive ACP of Example 5 using DCPD with a grain size distribution having a minimal content of grain sizes greater than 100 $\mu$m (e.g. corresponding to distribution B3 in Table 3) as a promoter. The powders are prepared as a hydrated precursor as described in Example 9.

The inventive PCA calcium phosphate undergoes ossification. Ossification refers to the replacement of the implanted synthetic calcium phosphate with bone which histologically is similar or identical to natural bone. Ossification of the inventive PCA calcium phosphate tends to occur in stages with more unorganized bone appearing prior to the establishment of more natural appearing tissue. The inventive PCA calcium phosphate is different from previous bone fillers and cements because bone formation does not occur only at the outer edge of the implant, but initiates simultaneously throughout the implant, presumably in association with the resorptive process. Within two to three weeks following implantation of the PCA material into a load bearing region, such as the tibia or radius, preliminary ossification is observed by the formation of small foci of mineralized osteoid formation (spicules). By four weeks, the spicules have given way to lacy appearing thin cancellous trabecular bone and thin cortical bone. At six weeks, ordered normal or thicker than normal compact cortical bone with lacunae-containing osteocytes is observed. At time points after six weeks, final remodeling occurs so that by twelve weeks the newly ossified bone is indistinguishable from native bone.

Thus, ossification in the presence of PCA calcium phosphate generally reaches completion and appears to occur more rapidly than normal bone growth. This rapid rate of ossification suggests the inventive PCA calcium phosphate enhances bone healing. New bone is observed as early as two weeks and may reach the fully histologically organized state within six weeks, but in any case by 3–6 months. In sheep segmental defect fracture models employing implants of up to 3 gms of hydrated precursor, bone having 100% of the strength of non-fractured bone was found within three months. In the presence of trophic or growth factors such as bone morphogenic proteins this process may be accelerated.

In preferred embodiments, in order to optimize ossification, devices, pastes and putties of the invention may be seeded with bone forming cells. This is most easily accomplished by placing the device (containing PCA calcium phosphate or a hydrated precursor thereto) in contact with a source of the patient's own bone forming cells. Such cells may be found in bone-associated blood or fluids, including exogenous fluids which have been in contact with bone or bone materials or regions, including the periosteum, cortical bone, cancellous bone or marrow. They are also present in tissue including cortical or cancellous bone, bone marrow or periosteum. In the case of devices such as screws and pins, the introduction of which into bone is accompanied by bleeding, no further seeding is required. For plates, which oppose only cortical bone, induction of a periosteal lesion which will contact the device is recommended. In yet other embodiments, it will be useful to surgically prepare a seating within the bone by removing a portion of cortical bone at the implant site. Other steps may also be taken to augment ossification, including introduction of bone forming cells harvested from the patient into the graft, or incorporation of trophic factors or bone growth inducing proteins into, or onto the device. Non-autologous bone cells are also within the scope of the invention if the desired amount of bone regeneration occurs prior to host rejection of the bone forming cells. Thus, cells or tissues obtained from primary sources, cell lines or cell banks may all be useful in certain embodiments. Similar considerations apply for cartilage formation and healing and the seeding of the inventive PCA calcium phosphate with chondrocytes and/or other cartilage forming cells.

Due to the nature of the reaction used to produce preferred formulations of the inventive PCA calcium phosphate, the ease of use as an implant material in a surgical setting is significantly improved over other bone substitute materials known to the art. Specifically, the reaction is initiated outside the body and proceeds slowly at room temperature thereby minimizing the possibility that the material will "set up" and become unusable prior to application to the surgical site. The reaction accelerates significantly at body temperature and the material hardens in place. Furthermore, the consistency and formability of the inventive PCA calcium phosphate as well as the reaction speed may be varied according to the therapeutic need, by modifying a few simple parameters.

Preparation of a PCA Calcium Phosphate. Many amorphous calcium phosphates tend to spontaneously convert to a more crystalline form over time. Hydroxyapatite is a thermodynamically favored form of calcium phosphate and is often the product of such conversion. The instant invention has recognized the value of a controlled conversion of an ACP to a more crystalline form (e.g. PCA calcium phosphate) without significant further crystallization, particularly when the conversion is performed in the presence of a limited amount of water and is accompanied by a hardening reaction. The instant invention provides reactions which lead to the formation of PCA calcium phosphate. These reactions advantageously may be initiated outside of the body, using a precursor having a paste or putty consistency and may be significantly accelerated at 37° C. leading to a hardened calcium phosphate product. In some embodiments, the hardened PCA calcium phosphate alone has a durometer and bulk modulus similar to traditional blackboard chalk. In some instances, hardened PCA material will be associated with the presence of unreacted precursors, promoters, and/or supplemental materials, side products and by-products.

According to the method of the invention, a paste- or putty-like hydrated precursor is formed by addition of water to a calcium phosphate precursor. The hydrated precursor is then heated to about 37° C., thereby initiating a substantially net endothermic reaction which is characterized by hardening of the paste or putty, as indicated by the differential scanning calorimeter (DSC) data shown in FIG. 16. In preferred embodiments, the PCA calcium phosphate material is produced from a hydrated precursor by conversion of a reactive amorphous calcium phosphate to PCA calcium phosphate in the presence of a promoter. Promoting the conversion of ACP in a paste form to well crystallized hydroxyapatite, accompanied by hardening of the paste via an endothermic reaction is also considered to be within the scope of the invention An endothermically setting bone cement provides several important advantages over calcium phosphate bone cements and fillers known in the art. Because the reaction does not give off heat there is no danger of heat related damage to cells and tissues in the implant area. Additionally, the endothermic nature of the reaction means reaction progress can be controlled by regulating the amount of heat available to support the reaction. The hydrated precursor reacts minimally at room temperature and below. This means that many of the handling problems associated with surgical cements and fillers known to the art are avoided.

In preferred embodiments, the reactants are mixed outside of the body, yielding a hydrated PCA calcium phosphate precursor material suitable for application to a surgical site. The reaction generally is completed after application to the surgical site, although in some embodiments the reaction is completed ex vivo. The PCA calcium phosphate reactions of the invention generally lead to hardening of the hydrated precursor in less than five hours, substantially hardening in about one to five hours under physiological conditions, and preferably in about 10–30 minutes. In a preferred embodiment, the reaction is initiated by adding physiological saline to a mixture of two dry components to form a thick paste which hardens in association with an endothermic reaction at 37° C. in about a half an hour. Other aqueous agents such as but not limited to, water, buffer solutions, serum or tissue culture medium may be used in place of saline.

Under any reaction scheme it is important that the ACP retains significant amorphous character prior to conversion. Specifically, the overall crystallinity within the starting ACP cannot exceed that desired in the end product. Thus certain reaction schemes may require stabilization of the amorphous nature of the ACP throughout the reaction period. Examples of suitable inhibitors of crystal formation known to the art include carbonate, pyrophosphate, and magnesium. Additional guidance for the use of inhibitors of crystallization may be found in Elliot, *Structure and Chemistry of the Apatites and Other Calcium Orthophosphates*, Elsevier, The Netherlands, 1994, herein incorporated by reference.

Types of Promoters, The purpose of the promoter is to promote the hardening of the hydrated precursor and preferably to accelerate the conversion of ACP to a PCA calcium phosphate. Any material or method which serves this purpose is considered to be within the scope of the reaction. This includes the limited case where hardening occurs in the absence of conversion, that is when a PCA calcium phosphate precursor is used as the starting material.

With respect to the conversion of ACP, a promoter may promote the overall reaction or any intermediate reactions involved in the conversion or hardening process. In this regard preferred promoters will reduce the activation energy for one or more specific steps in the conversion or hardening process.

The promoter used to convert a reactive ACP to the inventive PCA calcium phosphate may itself be converted to PCA calcium phosphate calcium phosphate or otherwise participate in a chemical or physical reaction during the conversion process. Such promoters are referred to herein as "participating" promoters.

Alternatively a promoter may remain substantially unchanged during the reactive ACP conversion serving essentially to catalyze or to initiate or enhance PCA nucleation and hardening. These promoters are referred to as "passive" promoters.

Promotion of the hardening and conversion of a reactive ACP to PCA calcium phosphate through the use of other means such as the use of heat, pressure, reactive gases, solvents, ionic solutions, or radiochemistry is also considered within the scope of the invention. Such promoting means are termed reaction enhancing or "enhancing" promoters.

Promoters may have different abilities or strengths in the promotion of the production of a hardened PCA calcium phosphate from ACP. Likewise, not all ACPs are equally reactive. Thus weak promoters will not always be effective in reacting with ACPs with low reactivity. In such circumstances stronger promoters will be preferred. Promoter strength may conveniently be tested by comparing the reactivity of a given promoter with the preferred carbonated ACP of the invention in both its heat activated highly reactive form as well as its non heat activated form using the method described in Example 8. The use of hand mixing of reactants is particularly suited for identification of highly reactive promoters. Less reactive promoters may benefit from mixing in an automated mill as described in Example 9. By use of these methods DCPD with the grain size distribution of B1 in example 10 was demonstrated to be a weak promoter, where as grain sizes in the range of <100 $\mu$m were found to be strongly reaction promoting.

In addition to the guidance given above for the matching of a particular promoter to a given ACP, such matching may be done empirically by mixing a given ACP with a selected promoter in the presence of about 1.0 mL water/g powder and heating the mixture at 37° C. in a moist environment. A suitable promoter exhibits PCA calcium phosphate formation and paste hardening under these conditions.

The method of preparation of the promoter and/or the ACP will affect the ease by which the hydrated precursor is converted into the PCA material. As noted above, the method of mixing the powdered reactants prior to addition of liquid affects the reactivity of the system. Thus, hand mixing using a mortar and pestle does not result in as reactive a system as a prolonged machine grinding of the reactant powders. Therefore when comparing promoters, it is important to used standardized preparation conditions.

It is hypothesized that the hardening with the associated conversion of ACP to the reactive PCA calcium phosphate is a surface catalyzed phenomenon. If so, it may be desirable to produce a particular promoter with a reproducible surface area. Specific surface area of the ACP and promoter powders can be controlled to control the reaction condition and final PCA material properties. Thus, to control reaction reproducibility it is advantageous to provide a promoter with a known grain size distribution. Standard sieving techniques are suitable for selection of specific grain sizes. Specific surface area has been shown to be correlated to the compressive strength, and possibly the porosity and resorbability, of the PCA material.

Many calcium- or phosphate-containing compounds may be used as participating promoters in the hardening reaction. A calcium phosphate promoter, may be of any crystalline structure and should be chosen so as to be reactive with ACP either directly or through the use of enhancing promoters. Preferred participating promoters are those which tend themselves to undergo conversion to hydroxyapatite through an intermediate PCA calcium phosphate phase.

Appropriate participating calcium phosphate promoters include neutral, basic and acidic calcium phosphates, preferably apatitic phosphates, which provide the appropriate stoichiometry for reaction to obtain an apatitic calcium phosphate. Suitable calcium phosphate promoters include, but are in no way limited to, calcium metaphosphate, dicalcium phosphate dihydrate, monetite, heptacalcium phosphate, tricalcium phosphates, calcium pyrophosphate dihydrate, hydroxyapatite, poorly crystalline apatitic calcium phosphate, tetracalcium phosphate, calcium pyrophosphate, octacalcium phosphate, and a second ACP. Other sources of phosphate or calcium, such as by way of example only, CaO, $CaCO_3$, calcium acetate, and $H_3PO_4$, may be mixed to form a final product to yield a desired Ca/P ratio close to natural bone. It may be desirable to provide the second component in the amorphous or poorly crystalline state, as well.

In a preferred embodiment, DCPD is used as a participating promoter with a grain size less than 200 μm, in more preferred embodiments with an average grain size of <95 μm, and in most preferred embodiments with an average grain size of about 35–45 μm and a grain size maximum of less than about 110 μm.

In those cases where amorphous calcium phosphate is used as the sole precursor to produce the inventive PCA calcium phosphate it is important to control the natural tendency of the ACP to convert to highly crystalline hydroxyapatite. On the other hand, the rate of conversion and hardening should be fast enough to have surgical utility. One approach is to combine a precursor ACP containing an inhibitor of crystal formation (e.g. the ACP of Example 5) with an ACP that does not contain an inhibitor of crystal formation (e.g., a promoter). The reactants may be mixed in a dry state, with the appropriate particulate size and an excess of the inhibitor-containing ACP. The reactants can then be exposed to crystal-forming conditions such as the addition of water, followed by an elevation in temperature, such as that which follows introduction into the body, to convert the reactants to the PCA calcium phosphate of the invention. Unless steps are taken to further promote this reaction, the use of ACP as a promoter alone leads to a PCA calcium phosphate that does not tend to harden exceptionally well.

It is an interesting and unexpected feature of the inventive reaction that along with ACP, a participating promoter may likewise be converted to PCA calcium phosphate. This has been demonstrated experimentally for both DCPD and stoichiometric hydroxyapatite. Thus the conversion of a crystalline calcium phosphate to a less crystalline state in a substantially endothermic reaction has been shown for the first time.

While the conversion of ACP to PCA calcium phosphate has been demonstrated herein above, it is recognized that alternative materials may also be converted to a PCA calcium phosphate. Thus the production of a hydrated precursor paste from a crystalline calcium phosphate (including PCA calcium phosphate) in the presence of a limited amount of water in association with a net endothermic reaction at 37° C. and accompanied by paste hardening is considered within the scope of the invention. A preferred embodiment of this approach features a PCA calcium phosphate and a DCPD as reactants to produce a PCA calcium phosphate bioceramic Hydroxyapatite is a thermodynamically favored form of calcium phosphate. It is therefore also within the scope of the invention to promote the conversion of the reactive ACP into a PCA calcium phosphate in association with hardening of a hydrated precursor, through the use of promoters which themselves do not convert to PCA calcium phosphate (or hydroxyapatite). Suitable such promoters are termed "passive" and include, but are not limited to nucleation causing substances and catalysts. Particularly suitable in this regard are substances which provide reactive surfaces which weakly promote apatitic crystallization to produce a poorly crystalline apatitic calcium phosphate.

In one aspect, the invention features the use of passive promoters which are of limited solubility or insoluble in the aqueous liquid used to hydrate the ACP. Suitable promoters include, but are not limited to, metals, metal oxides, ceramics, silicates, sugars, salts, or polymeric particulate. For many applications preferred promoters will be themselves biodegradable. In general these substances are provided in granular form with a grain size in the range of 1 to 500 μm, preferably 1 to 300 μm, and most preferably 1 to 200 μm. The actual grain size used may be varied to improve the reaction promoting characteristics of the particular substance.

Table 2 of Example 3 reports the effect of a variety of passive promoters in the conversion of ACP to PCA calcium phosphate in the presence of a limited volume of water. Generally the promoter is present in an amount less than or equal to the ACP, and specifically in the range of about 1:1 to about 5:1 ACP:promoter. An amount of water (here, weight=volume, since density of water is one) approximately equal to the total weight of the two dry components is used to prepare a paste. Actual proportions of ACP, promoter and water can be conveniently determined by mixing the components in varying amounts and selecting the formulation which leads to a hardened PCA calcium phosphate at 37° C. in the desired amount of time. Preferred passive promoters include but are not limited to granular forms of $SiO_2$, mica, $Al_2O_3$, poly(L-lactide) (PLLA), polyglycolide (PGA), and poly(lactide-co-glycolide) (PLGA) copolymers.

Lastly, suitable enhancing promoters include, but are not limited to, water, heat, salts and additional calcium phosphate sources. In general these substances act to enhance the reactivity of ACP with a second calcium phosphate thereby promoting the conversion of ACP to PCA calcium phosphate. Conversion reactions may include acid/base, displacement, substitution, and hydrolysis reactions.

The inventive reaction permits one to design and modify the chemical composition of the resultant product, thereby providing a further mode of controlling bioactivity of the final product. Because the amorphous calcium phosphate tends to react completely with the other solids, the Ca/P of the resultant solid will be determined by the total calcium and phosphates present as starting materials. This permits reliable manufacture of PCA calcium phosphate products simply by selection of the relative proportions of the starting amorphous and secondary calcium phosphates. It is generally desirable to maintain a calcium to phosphate ratio of about 1.1–1.9, preferably less than 1.5, and most preferably about 1.4.

A particularly useful approach is to form the precursor paste into the approximate shape or size and then harden the material in vitro in a moist environment at 37° C. If desired, the hardened material may then be precisely milled or machined to the desired shape prior to use in the surgical setting. In those cases where storage of the hardened material is desired, it may be useful to enhance the stability of the inventive PCA calcium phosphate. In such cases, exposure of the pre-formed object to inhibitors of hydroxyapatite crystallization may be useful. Inhibitors may be added to the aqueous medium used to prepare the inventive PCA calcium phosphate calcium phosphate. Alternatively, the finished material or objects made from it may be exposed to an inhibitory substance. Suitable such inhibitors include but are not limited to magnesium, carbonate, pyrophosphate, poly L-glutamate, polyacrylate, phosvitin, casein, and protein-polysaccharides. Guidance for the use of such compounds can be found in Termine et al. Arch. Biochem. Biophys. 140:318–325 (1970) incorporated herein by reference. Storage at 4° C. or preferably colder temperatures such as –20° C. or –75° C. will also retard crystallization.

In the embodiments described above, the paste or putty is hardened at 37° C. Hardening at 37° C. is important for in vivo application of the hydrated precursor; however, the reaction proceeds at both higher and lower temperatures. This reactivity range may be taken advantage of when the paste or putty is to be hardened outside the body. In such cases, higher temperatures may be employed to further accelerate the hardening process. In this regard temperatures less than about 48° C. are preferred.

For in vitro hardening the use of a moist environment is useful (although not critical) because the reaction tends to consume water. In addition it is desirable to avoid evaporative water loss of the sample while it is hardening. Thus, use of a reaction chamber with a high ambient humidity is preferred (>80%, preferably 100% humidity). Alternatively the reaction and hardening process can often be performed under water.

The PCA calcium phosphate materials and composites of the invention are porous. Air dried samples can generally absorb water to an extent of 20% or more of their total volume. In many embodiments amounts of water greater than 30% of the total sample volume may be absorbed and in some preferred embodiments, water in amounts of greater than 40% preferably greater than 50% of the sample volume may be absorbed.

Any approach affecting the porosity of the hardened sample may be employed, although preferred approaches include the use of controlled compression molding for ex vivo fabrication and the use of specific promoter grain sizes for either ex vivo or in vivo hardening. The reaction may be performed in a chamber or mold to any pressure up to at least five tons.

In establishing new formulations of the inventive material it will be useful to know the nature and extent of the reaction. A number of tests for the identification of reaction products and reaction completeness may be used.

Hardness may be determined by simple inspection or manually probing the reaction product. The use of quantitative measures employing load cells and force transducers is however preferred. Hardness alone does not necessarily confirm conversion, although the inventive reactions have been designed so that hardening is accompanied by conversion.

Figure 18:
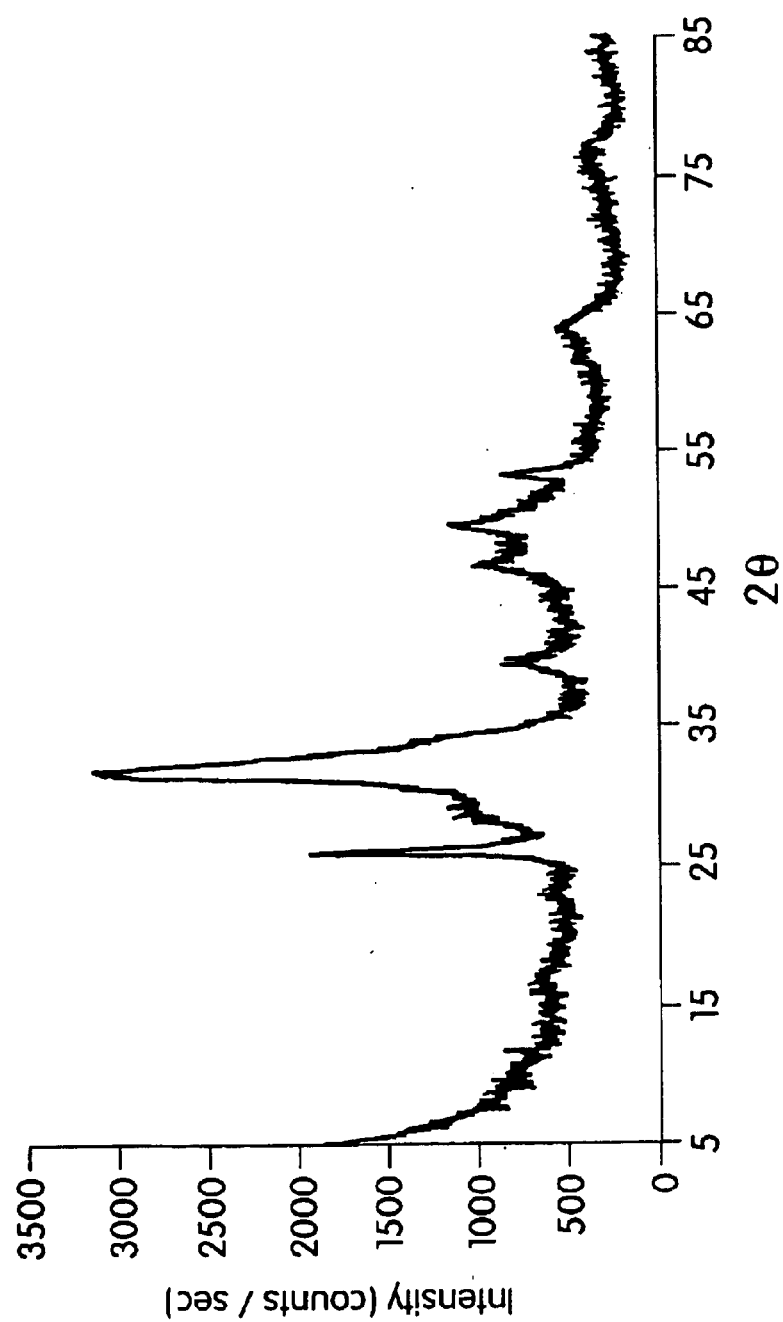
FIG. 18 is a full width XRD of the PCA calcium phosphate of the invention.

The X-ray spectra of the inventive PCA calcium phosphate is presented in FIG. 18. As can be seen from the figure the spectrum is characterized by broad peaks at approximately $2\theta=26$ and 32. An additional broad shoulder occurs at approximately $2\theta=29$ and another may be present at approximately $20\theta=33.6$. Absent from the spectra are any additional sharp peaks or sharp shoulders characteristic of more crystalline apatites occurring in the range of $2\theta=27$–34. In particular there are no sharp peaks or shoulders corresponding to Miller's Indices of 210, 112, or 300 for hydroxyapatite.

FTIR spectrum is characterized by peaks at 563 cm$^{-1}$, 1034 cm$^{-1}$, 1638 cm$^{-1}$ and 3432 cm$^{-1}$ (±2 cm$^{-1}$). Sharp shoulders are observed at 603 cm$^{-1}$ and 875 cm$^{-1}$, with a doublet having maxima at 1422 cm$^{-1}$ and 1457 cm$^{-1}$ (see, FIG. 6c).

For some embodiments it may be desirable to actually to have the presence of some unreacted crystalline calcium phosphate present following conversion (e.g. DCPD or hydroxyapatite). In such circumstances, the quantities of second calcium phosphate may be adjusted relative to the quantity of ACP present. Alternatively, reactions using a weaker promoter or less reactive ACP may also result in some unreacted starting materials. Mixtures of PCA calcium phosphate and DCPD, or PCA calcium phosphate and hydroxyapatite or PCA calcium phosphate and other reactants are within the scope of the invention. In some limited cases, the use of PCA calcium phosphate itself (provided it has a significant amorphous character) in place of ACP is possible.

An implantable bioceramic material may be prepared in precursor form as a paste or putty by addition of a fluid to the precursor materials and mixing, The precursor materials may include an ACP, a promoter and additional supplementary materials if required (in some cases some or all of these constituents may be partially pre-hydrated). The mixing of the components may occur in any convenient order. The components may be mixed and/or physically ground prior to the addition of fluid. Alternatively fluid may be added to a single dry component, and then additional dry components added to complete the paste.

A wide variety of proportions of reactants may be used, in most cases the absolute ratio of constituents will depend on the circumstances of the intended use. For systems employing only an ACP and a participating promoter the reactants will generally be used in equal amounts by weight. Water will also be added in a weight approximately equal to the combined weight of the other dry reactants.

In a preferred embodiment, a DCPD with grain size distribution similar to distribution B3 from Example 10 and a highly reactive carbonated ACP from Example 5 with an ACP:DCPD ratio of 0.5 g:0.5 g may be combined with water in amounts ranging from 0.7 to 1.3 mL.

In the case of reactions involving passive promoters and ACP alone, it has been found that ACP:promoter proportions in the range of about 5:1 to 1:1 work well. For a total weight of reactants of 1 gram, 0.5 to 1.5 mL water may be used.

Empirical determination of appropriate amounts of reactants and water may be made by (a) establishing ratios of dry components and water that lead to the formation of a workable paste or putty; (b) selecting those formulations which lead to hardening in a suitable amount of time (most often 20 to 60 minutes) at 37° C.; and/or (c) testing the performance of the selected formulations in a suitable model system (e.g. in vivo subcutaneous resorption or in vitro tissue culture resorption models).

In some preferred embodiments (e.g., Examples 8–10), the reaction occurs slowly at room temperature and is almost undetectable below 18 or 19° C. (see DSC example). The reaction is accelerated at higher temperatures, and particularly at body temperature. This property is particularly useful in a surgical situation, since the hydrated precursor paste formed by mixing reactants with a limited volume of water remains injectable and/or formable for a considerable period of time (up to several hours) while held at room temperature, provided care is taken to prevent evaporative moisture loss. Thus, at room temperature in air (ca. 22° C.) the paste hardens after a time greater than one hour and remains formable and/or injectable for longer than 10 minutes, and preferably longer than one hour and most preferably longer than three hours. Following injection at the implant site (ca. 37° C.), the paste hardens in less than about an hour, preferably in about 10–30 minutes. When held at 4° C. the paste is not hard even after several days, provided care has been taken to prevent evaporative moisture loss. Alternatively, once the material has been implanted, hardening can be accelerated by application of heat to the implant. Heat may be applied through the use of lasers, ultrasound, and the like, or by other means including the use of pharmaceuticals to locally raise or lower the body temperature.

Depending upon the amount of fluid added, the mixture of an ACP and a promoter results in a hydrated precursor mixture with varying consistency. By selecting the appropriate amount of liquid to be added to the reactants, the viscosity of the precursor paste may be adjusted according to need. The paste may be prepared either with an injectable or a formable consistency or it may be prepared with just enough liquid to be both injectable and formable.

Injectable paste is generally prepared by mixture of the reactants in an amount of water or buffer sufficient to produce the desired consistency for injection. Most often this will be as thick as possible while still being able to be passed through a 16–18 gauge syringe. For some formulations requiring injection directly into solid tissue (e.g. into cortical bone of an osteoporosis patient) thinner consistencies (e.g., 1.5 mL $H_2O$/g dry precursors) may be desired. Because of the low crystallinity of the component solids in the paste, the material has markedly improved flow characteristics over prior art compositions. Flow characteristics of the resultant paste are toothpaste-like while prior art materials inherit a granular or oat meal-like consistency. The paste may be prepared before use, up to a period of several hours if held at room temperature and evaporative water loss is minimized. Even when steps are taken to minimize evaporation, holding at room temperature is sometimes accompanied by drying out of the hydrated materials. In such instances, a small amount of water may be added and mixed to restore the desired consistency. The storage time may be extended by maintaining the paste at reduced temperatures in the range of 1–10° C. in the refrigerator provided steps are taken to minimize evaporative water loss.

In another preferred embodiment, a formable paste or putty may be prepared, which can be introduced into the implant site. The formable precursor is generally prepared by mixture of the dry reactants in an amount of water or buffer sufficient to produce the desired consistency for forming. Most often this will be as thick as possible while still being formable by hand, although thinner more flowable consistencies may be desirable for many applications. In many embodiments the preferred consistency will be similar to that of clay or glazing compound. The hydrated material may be prepared before use, up to a period of several hours if held at room temperature or below and evaporative water loss is minimized. The storage time may be extended by maintaining the hydrated material at reduced temperatures in the range of 1–10° C. in the refrigerator provided steps are taken to minimize evaporative water loss.

Application to the implant site will be performed according to the nature of the specific indication and the preferences of the surgeon. Similar considerations apply for cartilaginous implants as for bone. Injection techniques will be employed to deliver the inventive PCA calcium phosphate precursors directly into hard tissue (e.g. for osteoporosis patients) or into small fractures. For larger fractures putty-like consistencies will be preferred and will be implanted by hand or with a spatula or the like. Reconstruction will often use putty like forms but in some instances it will be more advantageous to pre-form, harden, and shape the material ex-vivo and implant a hardened form. Exposure or mixing of the material with blood or body fluids is acceptable and in many cases will be preferred as a method to promote osteo- or chondrogenesis. Implantation into soft tissues may employ any of the above approaches.

Formation of the reactive amorphous calcium phosphate. In preferred embodiments an ACP is converted in the presence of a promoter and water to PCA calcium phosphate. The use of an amorphous calcium phosphate, which can react quickly and completely to a product PCA calcium phosphate without significant further crystallization, provides a novel route to a highly resorbable calcium phosphate, with a variety of medical uses. The promoters of the instant invention promote conversion and hardening either by direct participation as a reactant along with ACP, or passively by serving as catalysts, nucleators or reaction enhancing agents, or in a combination of modes.

Not all ACPs have the same reactivity with a given promoter, and their reactivity is generally compared relative to their reactivity with a DCPD of grain distribution similar to B1 in Table 3. Examples 10 and 11 describe a variety of ACPs which have been tested for reactivity with such a DCPD. Use of a stronger DCPD promoter with a smaller grain size facilitates the reaction with weakly-reactive or otherwise un reactive ACPs. Generally less reactive ACPs will require the use of stronger promoters and in some cases combinations of promoters.

In a preferred embodiment, a highly reactive ACP is employed. Hydrated precursors comprising this ACP are capable of undergoing hardening and conversion either in the presence of a strong promoter such as a DCPD with small grain size (e.g. <63 μm) or in the presence of a relatively weak promoter such as a DCPD sample comprising a substantial amount of grains greater than 100 μm (e.g. distribution B1). One highly reactive ACP is a carbonated ACP which has been activated by heat treatment for approximately one hour at 460° C.

The invention also provides a test for identifying suitable reactive precursors for the inventive PCA calcium phosphate. The test comprises combining an amorphous calcium phosphate, DCPD, and water, producing a hydrated PCA calcium phosphate precursor substance and demonstrating its ability to harden in about 10 to 60 minutes at or around body temperature. Reactants found to produce hardened PCA calcium phosphate in this test may then be placed intramuscularly in a test animal and checked for biological resorbability. One hundred milligrams (100 mg), and preferably three hundred milligrams (300 mg), of PCA calcium phosphate thus prepared will resorb in less than 12 months, preferably less than 6 months and most preferably in less than 2 months in a rat muscle. Further 80% of one gram placed intramuscularly will be resorbed in the same time frame. Alternatively, at least 2 g placed subcutaneously will be fully resorbed in rat in less than 12 months, preferably less than 6 months and most preferably in less than 2 months. For the identification of less reactive forms of ACP it is preferred to use a weak DCPD promoter. Similar tests may also be established using other participant or passive promoters.

The method of the present invention permits initial formation of amorphous calcium phosphate particles of less than 1000 Å, preferably 200–500 Å, and most preferably 300 Å, the further growth of which are curtailed by rapid precipitation of the product from solution. In FIG. 1, a high-resolution transmission electron micrograph is shown to illustrate the morphological characteristics and the angstrom-scale nature of the preferred reactive amorphous calcium phosphate of the invention. Note the unclear boundaries separating the globule-like clusters, lacking clear edges and surfaces, in contrast to crystalline material.

During reaction of calcium and phosphate ion sources to form an amorphous calcium phosphate, a third ion may be introduced in the solution so that these ions are incorporated in the amorphous precipitate structure instead of trivalent $PO_4^{3-}$ group(s). Because some $PO_4^{3-}$ is replaced by the third ion, the overall $PO_4^{3-}$-decreases, thus increasing the Ca/P ratio of the amorphous precipitate (as compared to standard amorphous calcium phosphate) and modifying the valence or charge state of the calcium phosphate. The amorphous solids then may be rapidly freeze-dried to preserve the chemical and physical properties of the material. The amorphous solids then may be treated under specific conditions selected to promote removal of at least some of the third ion. In the case of carbonate, specific temperature and pressure conditions lead to the reduction of total carbon, presumably as gaseous carbon dioxide from the amorphous solid, while maintaining the amorphicity.

The source of the enhanced reactivity is not completely understood; however, it is believed to be associated with the degree of amorphicity (lack of crystallinity) and, in some embodiments, site vacancies in the material, as created by the process of the present invention. Site vacancies as envisioned herein refer to the lack of one pair of an ion pair (e.g. $CO_3^{2-}$) missing from $CaCO_3$ in a material containing many ion pairs. The presence of site vacancies may provide reactive sites for subsequent reaction. This stoichiometric imbalance may be responsible for the increased reactivity of the amorphous calcium phosphate The reactive ACP is a substantially amorphous solid with a higher Ca/P ratio than is typically found in amorphous calcium phosphates, which has generally been reported in the past to be about 1.50.

The amorphous state is induced by controlling the rate and duration of the precipitation process. The amorphous hydroxyapatite of the present invention is precipitated from solution under conditions where initial precipitation is rapid. Rapid crystal or grain growth enhances the number of defects within each grain, thereby increasing solubility. At the extreme end of the spectrum, crystal or grain growth is so rapid and defect density is so significant that an amorphous calcium phosphate results. Amorphous calcium phosphate is gel-like and includes solid solutions with variable compositions. These gels have no long range structure, but are homogeneous when measured on an Angstrom scale. Under physiological conditions, these amorphous compounds have high solubilities, high formation rates and high rates of conversion to PCA calcium phosphate.

The amorphous calcium phosphate solids produced by this method retain their amorphous nature sufficiently long enough to be introduced into the final reaction as substantially amorphous solids.

In one embodiment of the present invention, a solution is prepared which contains calcium and phosphate ions and a third ion in a concentration, at a pH and at a temperature which will promote the rapid nucleation and precipitation of calcium phosphate. When precipitation is sufficiently rapid, an amorphous gel-like calcium phosphate is formed. Because the thermodynamically favored crystalline form of hydroxyapatite is enhanced by reducing the rate of reaction, certain processing steps of increasing the rate of reaction may be taken to ensure that an amorphous compound is obtained. The following factors, among others, are to be considered when designing a solution for the rapid precipitation of the amorphous calcium phosphate of the present invention.

Preferred conditions: Rapid mixture of calcium and phosphate sources to increase the rate of reaction. The rate of reaction is increased to favor non-stable phases as a product. Allowing more reaction time for each of the ions to juxtapose correctly to form a solid will result in a more thermodynamically favorable crystalline and stable structure.

Preferred calcium and phosphate sources: The use of highly concentrated or near supersaturation solutions ensures that a more rapid reaction will occur.

Preferred temperature: Although the reaction can be carried out at room temperature, temperatures of near boiling point to increase the concentration of one reactant is a possible means of increasing the rate of reaction.

In one embodiment, an aqueous solution of calcium ions, phosphate ions and carbonate ions are mixed together rapidly to obtain a carbonate containing amorphous calcium phosphate solid. The relative concentrations of the ions are selected to give a precipitate having the desired Ca/P ratio. The carbonate ion substitutes for a phosphate ion in the amorphous calcium phosphate. The carbonated amorphous calcium phosphate may be obtained by precipitation from an aqueous carbonate solution. Suitable aqueous carbonate solutions include, by way of example only, bicarbonate solution, sodium carbonate solution, potassium carbonate solution. It is further contemplated as within the scope of the invention to use non-aqueous solutions.

Use of a carbonated material is desirable because it permits manipulation of the Ca/P ratio by substitution of $PO_4^{3-}$ by $CO_3^{2-}$. Additionally, the presence of $CO_3^{2-}$ is known to retard the development of crystallinity in amorphous calcium phosphate. It is recognized, however, that other ions or a mixture of ions may be suitable in place of or in addition to carbonate ion in modifying the Ca/P ratio and in introduction of reactive site vacancies into the amorphous calcium phosphate, such as by way of example only, nitrate, nitrite, acetate, $Mg^{+2}$ and $P_2O_7^{4-}$ ions.

The amorphous calcium phosphate precipitate may be collected and filtered prior to activation. It is preferred to perform this step in a cold room or at sub-ambient temperatures so as to preserve the amorphous state of the precipitate collected. Collection may typically may be carried out by any conventional means, including, but in no way limited to gravity filtration, vacuum filtration or centrifugation. The collected precipitate is gelatinous and is washed more than once with distilled water.

The washed precipitate is then dried under any conditions which maintain the amorphous character of the material. Lyophilization is a suitable, but not exclusive, technique. Upon freezing, the precipitate while kept frozen, is dried to remove the bulk of the entrained liquid. This procedure may be accomplished by placing the frozen precipitate into a vacuum chamber for a given period of time. Freeze-drying typically occurs at liquid nitrogen temperatures for a time in the range of 12–78 hrs, preferably about 24 hours, and under a vacuum in the range of $10^{-1}$–$10^{-4}$, preferably $10^{-2}$, torr. A preferred method includes lyophilization because the cryogenic temperatures typically used in lyophilization inhibit further crystallization of the material. As a result, the amorphous calcium phosphate obtained thereby is an extremely fine free flowing powder.

The dried ACP may then be activated to a highly reactive ACP. In a preferred embodiment, where carbonate is present in the ACP, the ACP powder is heated to drive off remaining free water, water of hydration, and to remove carbon, presumably through the decomposition of $CO_3^{2-}$ into $CO_2$ and oxygen. The heating step is carried out at a temperature of less than 500° C. but more than 425° C., so as to prevent conversion of the amorphous calcium phosphate into crystalline hydroxyapatite. Heating is preferably carried out at a temperature in the range of 450–460° C. for 1 to 6 hours preferably for 50 to 90 minutes.

Atmospheric pressure is used for convenience in most of the embodiments for production of ACP described herein. However, the use of vacuum with appropriate temperatures is considered to be within the scope of the invention.

To produce a highly reactive ACP it is desirable to maintain the amorphous property of the material throughout the entire ACP synthesis. If significant crystallinity in its entirety (single crystalline regions) or even in local domains (microcrystalline regions) is introduced during the process or in the final product, the solid has been found to become less reactive. The resultant highly reactive calcium phosphate is amorphous in nature and has a calcium to phosphorous ratio in the range of 1.55 to 1.65. In a preferred embodiment, the amorphous calcium phosphate has a Ca/P ratio of about 1.58.

Low crystallinity and site vacancies (porosity and/or stoichiometric changes) may account for the observed higher reactivity of the amorphous calcium phosphate of the present invention. This is supported by the following observations: a.) A carbonate-containing amorphous calcium phosphate which has been heated to 525° C. is observed to have an increased crystalline content and to have a corresponding decrease in reactivity. b.) Amorphous calcium phosphate that is heated to only 400° C. retains its amorphous characteristic, but exhibits a decreased reactivity. c.) Non-carbonated ACPs heated to 460° C. have been studied using the DCPD reaction (as described in example 8) and while reactive with a strong DCPD promoter were not reactive with a weak DCPD promoter.

These observations suggest that both amorphicity and decreased carbon content (vacant reactive sites) are a factor in reactivity. This is not intended to be in any way an exclusive explanation for the basis of reactivity. Other basis for the observed reactivity are considered to be within the scope of the invention.

Figure 4A:
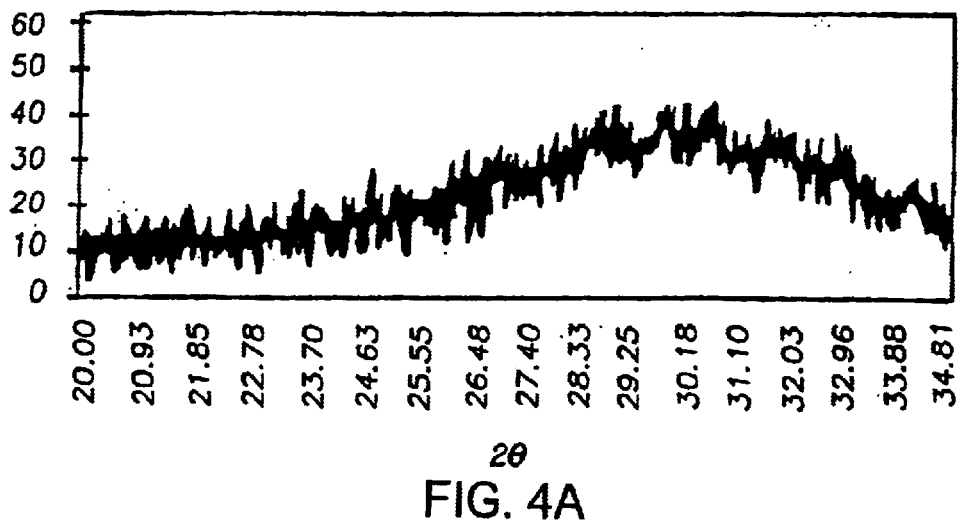
FIG. 4 are X-ray diffraction patterns of (a) reactive amorphous calcium phosphate; and (b) dicalcium diphosphate used in a reaction to form a bone substitute material of the invention.
Figure 17A:
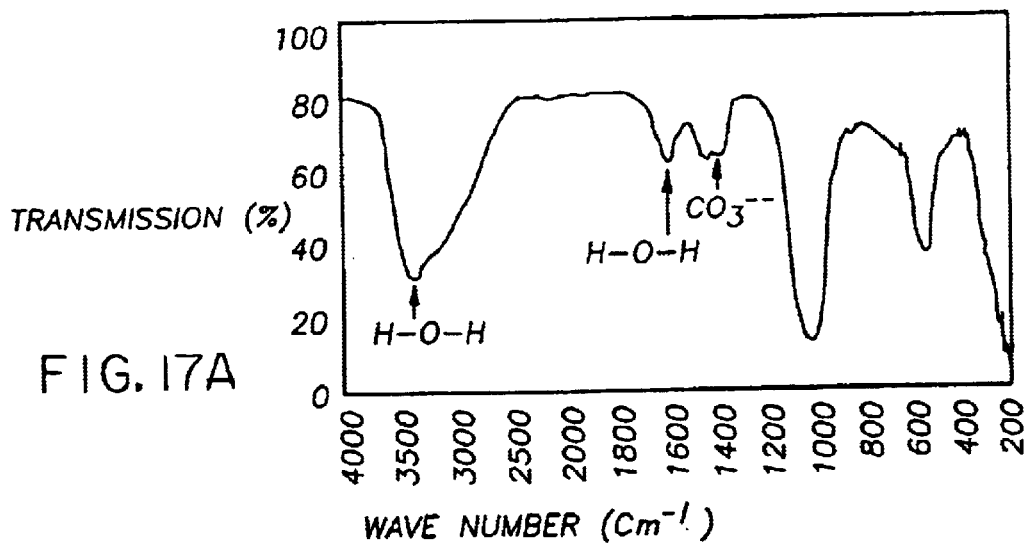
FIG. 17 is infrared spectra of the amorphous calcium phosphate material before heat treatment (FIG. 17a) and after heat treatment (FIG. 17b)
Figure 17B:
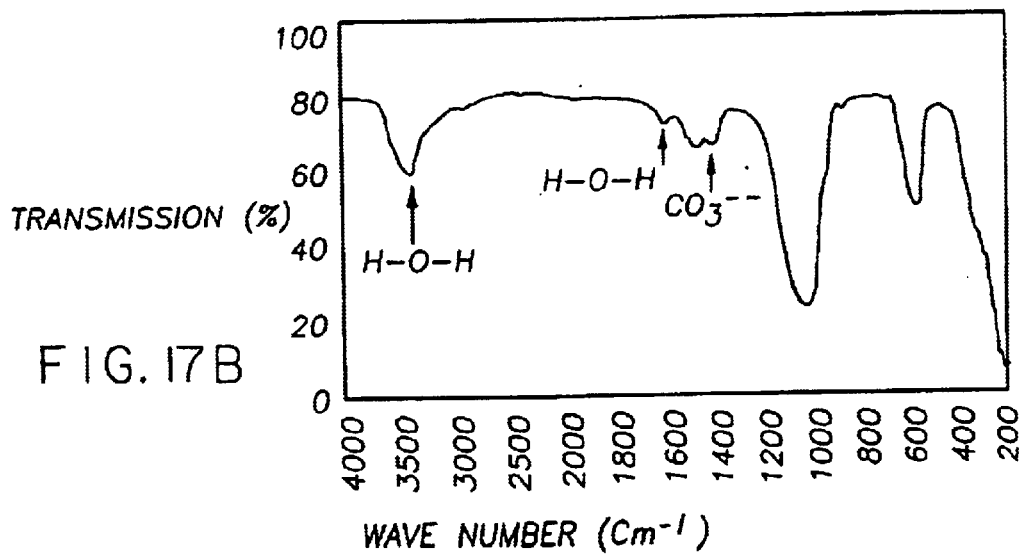

The resulting amorphous calcium phosphate powder is a highly reactive amorphous calcium phosphate material with a Ca/P ratio of between 1.1–1.9, preferably about 1.55 to 1.65, and most preferably about 1.58. FIGS. 17a and 17b illustrate the infrared spectra of the amorphous calcium phosphate after lyophilization process (FIG. 17a) and after the subsequent heat treatment at 450° C. for 1 hr (FIG. 17b). Infrared peaks illustrating presence of local chemical groups in the material show that the presence of H—O—H (at approximately 3,400 cm−1 and 1640 cm−1) and $CO_3^{2-}$ group (at 1420–1450 cm−1) are significantly reduced after heat treatment. However, the x-ray diffraction patterns in FIG. 4a of heat activated ACP demonstrate that the amorphous state is retained after heating and lyophilization. The XRD pattern is characterized by broad peaks and undefined background with absence of sharp peaks between $2\theta=20$ to 35 or at any diffraction angles that correspond to known crystalline calcium phosphates.

Figure 2:
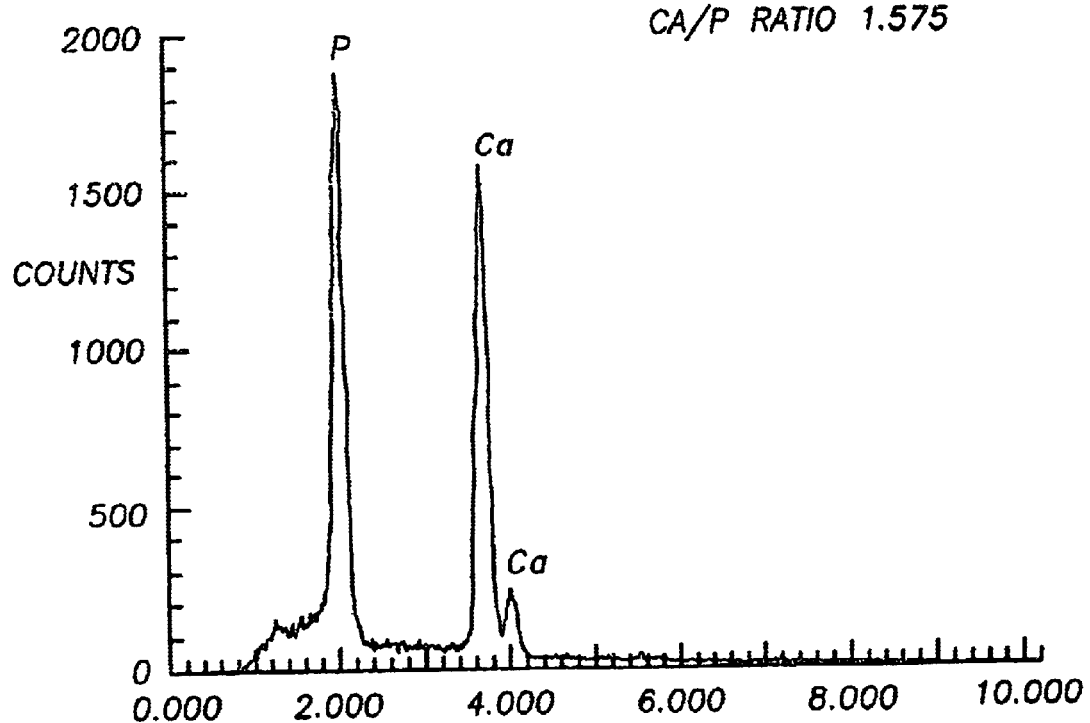
FIG. 2 is an energy-dispersive electron microprobe spectrum of the reactive amorphous calcium phosphate of the present invention after the vacuum heating procedure which yielded Ca/P to be 1.58.

The Ca/P measurement performed using wave length-dispersive X-ray analysis on an electron micro-probe of the same material after heat treatment yields Ca/P to be 1.58 (FIG. 2).

These characterizations demonstrate that although there is a change in the local moiety of certain groups in the amorphous calcium phosphate solids, the overall amorphicity is maintained throughout the process.

The PCA calcium phosphate of the invention may be used in a variety of formulations and in a variety of applications, some of which are described hereinbelow.

Composite Materials.

A strongly bioresorbable ceramic composition may be used in the repair and growth promotion of bone tissue (a bone substitute composite). The composition comprises a biocompatible and strongly bioresorbable poorly crystalline apatitic (PCA) calcium phosphate combined with a suitable biocompatible matrix or additive.

In one aspect, the invention provides for a strongly bioresorbable composite comprising a bioresorbable, PCA calcium phosphate and additional bioresorbable supplementary materials which can be prepared under mild conditions at room or body temperature (e.g., 20–40° C.). The composite may be applied to bone-contacting surfaces of prosthetic devices, for use as a bone cement. It may be applied directly to bone defects as a filler, where it is capable of promoting the growth of new bone tissue. Alternatively, the composite may be used to fabricate fixtures or devices such as screws and plates, which under appropriate circumstances will be resorbed and replaced by bone. The composite may also be used free standing in non-osseous tissue. When a pharmaceutically active component is added to the composite, it serves as a drug delivery device. Release of the agent may occur over a long period of time after implantation as the composite slowly biodegrades. See, related co-pending application U.S. Ser. No. 08/729,342 entitled "Delivery Vehicle", herein incorporated by reference.

The current invention employs a strongly bioresorbable and ossifying PCA calcium phosphate useful as an implantable bioceramic for the treatment of bone disorders and injuries and other biological applications requiring resorbable calcium phosphate. "Full" resorption means that no significant extracellular fragments remain. The resorption process involves elimination of the original implant materials through the action of body fluids, enzymes or cells. Resorbed calcium phosphate may, for example, be redeposited as bone mineral, or by being otherwise reutilized within the body, or excreted. The composites disclosed herein may undergo resorption (i.e., at least 80%, preferably 95–99% and most preferably >99%) of the total mass (at least 1 g and preferably 1–5 grams) of the implanted PCA material preferably within one year, more preferably within 9 months or 6 months, more preferably in less than 3 months, and most preferable within 1 month.

The PCA calcium phosphate of the invention is characterized by its biological resorbability and substantial absence of crystallinity, as is discussed hereinabove. Its crystalline character is substantially the same as natural bone, as compared to the higher degree of crystallinity seen in the bone substitute materials known to the art. The inventive PCA calcium phosphate also is biocompatible, that is, no significant detrimental reaction (e.g., inflammation or fibrosis) is induced in the host by the implanted composite material. Materials which induce a medically acceptable level of inflammation or fibrosis are considered biocompatible. In addition, the material is also bioactive, in that apposition of new bone at the host/composite interface occurs.

In an important aspect of the invention, the ease of use of the inventive implantable bioceramic material in a surgical or manufacturing setting is significantly improved over other bone substitute composite materials known in the art. Specifically, the setting reaction associated with the formation of PCA calcium phosphate may be initiated outside the body and proceeds slowly at room temperature thereby minimizing any possibility that the material will "set up" prior to heating (e.g. prior to application to the surgical site or in the manufacturing incubation). Setting accelerates significantly at about 37° C. causing the material to harden. The hardened PCA calcium phosphate alone has a durometer and bulk modulus similar to traditional blackboard chalk. In some instances, hardened PCA material will be associated with the presence of unreacted precursors, promoters, and/or supplemental materials, side products and by-products.

By formulating the PCA material as a composite, mechanical properties of the material may be improved. In some formulations, the hardened PCA calcium phosphate alone is brittle and has a durometer and bulk modulus similar to traditional blackboard chalk. The preparation of PCA calcium phosphate as a composite material is desirable in order to alter the mechanical properties for some medical uses. Furthermore, the consistency, formability and hardness of the PCA calcium phosphate, as well as the reaction speed, may be varied according to the therapeutic need by selection of the appropriate supplementary materials from which to prepare the implantable bioceramic composite material of the invention.

Preparation of the implantable bioceramic composite. The composite material of the present invention is prepared by combining the PCA calcium phosphate of the invention with a selected supplementary material. The PCA calcium phosphate may serve as the reinforcing material, the matrix or both. The PCA calcium phosphate of the invention in it's initial paste form (i.e., as a hydrated precursor) typically maintains a pH of about 6–7 and is therefore compatible with a wide range of additives without deleterious effect. The supplementary material is selected based upon its compatibility with calcium phosphate and its ability to impart properties (biological, chemical or mechanical) to the composite, which are desirable for a particular therapeutic purpose. For example, the supplementary material may be selected to improve tensile strength and hardness, increase fracture toughness, alter elasticity, provide imaging capability, and/or alter flow properties and setting times of the PCA calcium phosphate.

The supplementary material may be added to the PCA calcium phosphate in varying amounts and in a variety of physical forms, dependent upon the anticipated therapeutic use. By way of example only, the supplementary material may be in the form of sponges (porous structure), meshes, films, fibers, gels, filaments or particles, including micro- and nanoparticles. The supplementary material itself may be a composite. The supplementary material may be used as a particulate or liquid additive or doping agent which is intimately mixed with the resorbable PCA calcium phosphate. The supplementary material may serve as a matrix for the PCA calcium phosphate, which is embedded or dispersed within the matrix. Alternatively, the PCA calcium phosphate may serve as a matrix for the supplementary material, which is dispersed therein. The supplementary material may be applied as a coating onto a PCA calcium phosphate body, for example, as a post-fabrication coating to retard resorption time or otherwise affect the bioceramic material properties. Lastly, the supplementary material may be coated with PCA calcium phosphate.

The supplementary materials are desirably biocompatible, that is, there is no detrimental reaction induced by the material when introduced into the host. In many instances, it is desirable that the supplementary material also be bioresorbable. In many preferred embodiments, the supplementary material will have an affinity for calcium, phosphate or calcium phosphates which will enhance the strength of the PCA calcium phosphate/supplementary material interface. The affinity may be specific or mediated through non-specific ionic interactions. By way of example only, suitable bioerodible polymers for use as a matrix in the composite include, but are not limited to, collagen, glycogen, chitin, celluloses, starch, keratins, silk, nucleic acids, demineralized bone matrix, derivativized hyaluronic acid, polyanhydrides, polyorthoesters, polyglycolic acid, polylactic acid, and copolymers thereof. In particular, polyesters of α-hydroxycaboxylic acids, such as poly(L-lactide) (PLLA), polyp,L-lactide) (PDLLA), polyglycolide (PGA), poly(oactide-co-glycolide) (PLGA), poly(D,L-lactide-co-trimethylene carbonate), and polyhydroxybutyrate (PHB), and polyanhydrides, such as poly(anhydride-co-imide) and co-polymers thereof are known to bioerode and are suitable for use in the present invention. In addition, bioactive glass compositions, such as compositions including $SiO_2$, $Na_2O$, $CaO$, $P_2O_5$, $Al_2O_3$ and/or $CaF_2$, may be used in combination with the PCA calcium phosphate of the invention. Other useful bioerodible polymers may include polysaccharides, peptides and fatty acids.

Bioerodible polymers are advantageously used in the preparation of bioresorbable hardware, such as but not limited to intermedulary nails, pins, screws, plates and anchors for implantation at a bone site. In preferred bioresorbable hardware embodiments, the supplementary material itself is bioresorbable and is added to the PCA calcium phosphate in particulate or fiber form at volume fractions of 1–50% and preferably, 1–20 wt %. In some preferred embodiments, the bioresorbable fiber is in the form of whiskers which interact with calcium phosphates according to the principles of composite design and fabrication known in the art. Such hardware may be formed by pressing a powder particulate mixture of the PCA calcium phosphate and polymer. In one embodiment, a PCA calcium phosphate matrix is reinforced with PLLA fibers, using PLLA fibers similar to those described by Törmälä et al., which is incorporated herein by reference, for the fabrication of biodegradable self-reinforcing composites (*Clin. Mater.* 10:29–34 (1992)).

The implantable bioceramic composite may be prepared as a paste by addition of a fluid, such as water or a physiological fluid, to a mixture of a PCA calcium phosphate and a supplemental material. Alternatively, a mixture of the supplementary material with hydrated precursor powders to the PCA calcium phosphate can be prepared as a paste or putty. In cases where the supplementary material is to be dispersed within or reacted with a PCA calcium phosphate matrix, water may be added to one of the precursor calcium phosphates to form a hydrated precursor paste, the resulting paste is mixed with the supplementary material, and the second calcium phosphate source is then added. Alternatively, the calcium phosphate sources which make up the PCA calcium phosphate precursor powder may be premixed, water may then be added and then the supplementary material is added. In those cases where it is desirable to have the supplementary material serve as the matrix, the fully hardened PCA calcium phosphate will be prepared in the desired form which will most often be of controlled particle size, and added directly to the matrix forming reaction (e.g., to gelling collagen). These materials may then be introduced into molds or be otherwise formed into the desired shapes and hardened at temperatures ranging from about 35–100° C. A particularly useful approach is to form the composite precursor paste into the approximate shape or size and then harden the material in a moist environment at 37° C. The hardened composite may then be precisely milled or machined to the desired shape for use in the surgical setting. The amount of particular PCA calcium phosphate to be incorporated into the supplemental material matrix will most often be determined empirically by testing the physical properties of the hardened composite according to the standards known to the art.

In preferred embodiments, the reactants are mixed outside of the body, yielding a formable composite material comprising a hydrated precursor material having a physical integrity suitable for application to a surgical site. Conversion to the PCA material generally is complete after application to the surgical site. The supplemental materials will generally be in final form when added to the PCA calcium phosphate or hydrated precursor paste, although the use of polymer monomers and precursors, added to the paste is considered within the scope of the invention. In a preferred embodiment, the conversion reaction is initiated by adding distilled water to a mixture of the dry precursor components to form a thick hydrated precursor in the form of a paste or putty. Other aqueous agents such as buffers, saline, serum or tissue culture medium may be used in place of distilled water. In other preferred embodiments, sufficient water may be added to the precursor powders to form a paste which is readily injectable with an 18 gauge needle. Bioceramic composite materials of the invention generally harden in less than five hours and substantially harden in about one to five hours under physiological conditions, and preferably in about 10–30 minutes. Most often the resulting bioresorbable PCA calcium phosphate will be calcium deficient with a calcium to phosphate ratio of less than 1.5 as compared to the ideal stoichiometric value of approximately 1.67 for hydroxyapatite.

The invention also provides a test for identifying suitable reactive PCA calcium phosphate and reactive precursors for use in the composites of the invention. Specifically, precursors are combined, are hydrated with a limited amount of water (so that a paste or putty is formed), and are allowed to harden into a PCA material. Desirable precursors are capable of hardening in a moist environment, at or around body temperature in less than 5 hours and preferably within 10–30 minutes. Components which harden in this way may then be placed intramuscularly or subcutaneously in a test animal and checked for biological resorbability. Desirable materials are those that, when implanted as a 1–5 g pellet, are at least 80% (preferably 95–99% and most preferably >99%) resorbed within one year. Generally, it is easier to test resorption of gram quantities of material in subcutaneous sites.

Medical devices prepared from the inventive composites using all bioresorbable supplementary materials will themselves be resorbable and in preferred embodiments, strongly bioresorbable. The composites used in these devices may be designed to impart the desired mechanical properties to the devices making them useful in the surgical setting (e.g., orthopedic pins and screws). Following placement in the host, the devices will gradually be replaced by bone i.e., ossification of the bone site occurs. This is in contrast to merely biocompatible materials where the device promotes apposition of bone at its surface, but does not resorb so as to ossify the implant site. While resorption time in vivo will generally depend upon the actual identity of the supplementary material, as well as the graft size and location, for those composites with less than 20% vol/vol supplementary material, resorption of the PCA calcium phosphate and ossification at the implant site will be generally complete in less than six months and most often in about one month. In some cases, the resorbable supplemental material will still be present embedded in the newly formed bone, thus being resorbed over a longer time course than the PCA calcium phosphate. The use of resorbable hardware obviates the need for a subsequent surgical procedure to remove the device.

The resorbability of the implantable bioceramic composite material of the instant invention is attributable in part to the porosity, crystallinity and chemical composition of its component materials. The bioceramic composite material of the invention comprises a poorly crystalline apatitic calcium phosphate, substantially similar to that found in natural bone. Lack of crystallinity in apatites is associated with somewhat increased solubility in aqueous systems compared to other more crystalline species, and thus the low crystallinity and/or presence of stable amorphous apatitic domains is believed to promote its resorbability in biological systems, Porosity facilitates both the penetration of cells and cell processes into the bone substitute material matrix and the diffusion of substances to and from the matrix interior. Accordingly, low porosity composite materials resorb more slowly in vivo than those of high porosity.

In preferred embodiments, in order to optimize ossification, the devices and objects may be seeded with bone forming cells. This is most easily accomplished by placing the device in contact with a source of the patient's own bone forming cells. Such cells may be found in bone-associated tissue, blood or fluids, including exogenous fluids which have been in contact with bone or bone materials or regions, including the periosteum, cancellous bone or marrow. In the case of devices such as screws and pins, the introduction of which into bone is accompanied by breach of the periosteum and/or bleeding, no further seeding is required. For plates, which oppose only cortical bone, induction of a periosteal lesion which will contact the device is recommended. In yet other embodiments, it will be useful to surgically prepare a seating within the bone by removing a portion of cortical bone at the implant site. Other steps may also be taken to augment ossification, including introduction of bone forming cells harvested from the patient into the graft, or incorporation of trophic factors or bone growth inducing proteins into, or onto, the device. Use of non-autologous bone cells is also within the scope of the invention if the desired amount of bone regeneration occurs prior to host rejection of the bone forming cells. Thus, cells or tissues obtained from primary sources, cell lines or cell banks may all be useful in certain embodiments. See, U.S. application Ser. No. 08/729,354 entitled, "Cell Seeding in Ceramic Compositions" incorporated herein by reference.

Bioresorbable polymers may also be used in the preparation of bone glues or putties for use in load bearing situations. Supplementary materials may be added to the composite to increase compressibility and load-bearing properties of the bone glue. In particular, carbon fibers or other reinforcing fibers may be added to the composite. In the production of fiber-reinforced bone substitute glues, it may be advantageous to plasma etch the fibers to improve the quality and strength of the calcium phosphate/fiber interface. PCA calcium phosphate may also be hardened at 37° C., pulverized or otherwise fragmented, and mixed with known binders such as bone glues cements, fillers, plasters, epoxies, other calcium phosphates, or gels such as, but not limited to, calcium sulfate, tricalcium phosphate, tetracalcium phosphate, alginate, collagen, or commercially available products such as Endobone (Merck), Hapset (Lifecore Biomedical), SRS (Norian), Bonesource (Leibinger), Collograft (Zimmer), Osteograf (CereMed), and Simplex (Howmedica). For applications where hardened PCA calcium phosphate will be dispersed within the binder substance, most often the binder will be prepared by methods known to the art and mixed with the particulate PCA calcium phosphate in approximately equal volumes, although actual proportions will be varied in ways known to the art to produce compositions of desired consistency, workability and adherence.

In yet another embodiment, braided sutures, typically prepared from polyester, may be coated with the PCA calcium phosphate of the invention, to improve their biocompatibility. Coated sutures may be prepared by dipping the suture into a slurry containing finely divided particulate PCA calcium phosphate. The affinity of the suture for the PCA calcium phosphate coating may be improved by surface treating either the suture, the PCA calcium phosphate particle or both. Surface treatments include plasma etching and/or chemical grafting.

In other embodiments, a composite is provided comprising PCA calcium phosphate and a non-resorbable or poorly resorbable material. Suitable non-erodible or poorly erodible materials include dextrans, polyethylene, polymethylmethacrylate (PMMA), carbon fibers, polyvinyl alcohol (PVA), poly(ethylene terephthalate)polyamide, bioglasses, and those compounds listed previously for use in bone glues or putties. In one embodiment, carbon fibers may be used to reinforce the PCA calcium phosphate. In such applications, fibers lengths of 0.05 $\mu$m –20 cm and fiber content typically in the range of 0.01–50 vol % are used depending upon the intended use.

Another use is to permanently imbed useful objects, such as a pin or reinforcing mesh, into bone itself. The object serves as an anchor for the stable attachment to natural bone. This is particularly useful in the attachment of ligaments and tendons to bone. Objects comprising bioresorbable and ossifying or dental prosthesis seating PCA calcium phosphate and a suitable non-resorbable hardware may be placed into a bone and further secured with additional PCA calcium phosphate material or composite material in a bone glue formulation. The hardware then becomes embedded into the bone following reossification of the PCA calcium phosphate.

Calcium phosphates, including hydroxyapatites, tricalcium phosphate and tetracalcium phosphate, may be used as the non-resorbable supplementary materials of the inventive composites, in particular to maintain biocompatibility of the composite. In these embodiments, the calcium phosphates are most likely to be non-resorbable and to be pre-hardened in a particulate, fiber-like or other pre-formed shape. These solid calcium phosphate additives may further be compressed, sintered or otherwise modified prior to mixture with the PCA calcium phosphate.

In yet another embodiment of the invention, a composition is prepared by intimately mixing the PCA calcium phosphate with an additive which alters the resorption properties, setting time and/or flow characteristics of the composite. For example, silicone oil or other lubricating polymers or liquids may be added to the composite to improve the flow characteristics of the composite for delivery to the host by syringe. The lubricant is preferably biocompatible and capable of rapid leaching from the bone substitute material composite following solidification of the PCA calcium phosphate in vivo. Suitable lubricants include, by way of example only, polymer waxes, lipids, surfactants and fatty acids. Lubricants may be used in a concentration of about 0.1 to about 30 wt %.

In yet another embodiment of the invention, the composite contains a PCA calcium phosphate and a radiographic supplemental material for imaging the implant in vivo. Suitable electron dense materials include materials known in the art, such as titanium and barium oxide, in clinically relevant concentrations.

In a preferred embodiment, a bioceramic material may be prepared with a Young's Modulus similar to bone by preparing a polyethylene composite containing the resorbable PCA calcium phosphate of the invention. In other preferred embodiments, a resorbable polymer such as poly(L-lactide) or collagen may be used to prepare a composite with similar properties as normal bone. In another preferred embodiment, the particulate PCA calcium phosphate is pressed into a desired shaped and the pressed body is impregnated with the supplementary material. In yet another preferred embodiment, hydrated precursor materials of the PCA calcium phosphate are mixed with the supplementary material and the conversion to the bioceramic material is initiated in the presence of the supplementary material. Generally, the inventive PCA calcium phosphate will be present in the composite at a volume fraction of less than 0.7 and preferably less than 0.5.

The composition of the invention may be prepared in any conventional manner useful in the preparation of composite materials, including but not limited to blending, mixing, alloying, laminating, filament winding and pultruding. A variety of strategies for the design and fabrication of polymer/inorganic composites, fibers and matrix resins and other reinforcement technologies are useful and will be known in the art. Guidance regarding the preparation of HA/polyethylene composites can be found in Bonfield in *Introduction of Bioceramics* at pp. 299–303 and the references therein, all incorporated by reference. Additional guidance may be obtained from the following sources, incorporated herein by reference: Jang, *Advanced Polymer Composites: Principles and Applications*, ASTM Int'l, Materials Park, Ohio (1994); Opila et al. Eds., *Polymer/Inorganic Interfaces*, Materials Research Soc., Pittsburgh, Pa. (1993); Saifullin, *Physical Chemistry on Inorganic, Polymeric and Composite Materials*, Ellis Horwood, N.Y. (1992); Ducheyne et al. in *Introduction to Bioceramics*, Hench and Wilson, Eds. World Scientific Publishing, N.J. pp 281–298 (1993); and Törmälä, *Clin. Materials* 10:29–34 (1992).

The bioceramic composite material may also be prepared with varying degrees of porosity. In one embodiment, the use of a dry mixture of controlled particle size reactants leads to a porous composite material. Other methods of promoting porosity, such as chemical or physical etching and leaching, may be employed.

In yet another embodiment, a mixture of the PCA calcium phosphate and a polymeric supplemental material may be extruded by conventional polymer extrusion techniques to form tubes, fibers and other shapes. For extrusion purposes, the supplemental material is preferably an organic polymer. In some situations, where increased tensile strength and modulus and stiffness are desired, the composite may be extruded or otherwise mechanically deformed to align polymer chains to increase composite strength. The composite may also be hardened under pressure and/or heat to provide a composite that is more dense, tougher and resorbs at a slower rate in vivo. In general, conditions which cause rapid conversion of the PCA calcium phosphate to the more crystalline HA should be avoided.

In some embodiments, it may be desirable to modify the surface of the PCA calcium phosphate and/or the supplemental material in order to improve the interface between the two materials and/or to improve the affinity of pharmaceutically active agents, e.g., proteins, to the composite. For example, the inventive calcium phosphate may be grafted with moieties which show affinity for proteins and other organic molecules. Alternatively, the composite may be subjected to surface treatments, such as plasma etching to improve interfaces between the two phases as is known in the art.

For some embodiments in which the composite material is prepared and hardened in advance of its surgical use, and where storage is desired, it may be desirable to enhance the stability of the poorly crystalline state of the composite. In such cases, exposure of the pre-formed composite to crystallization inhibitors may be useful. Inhibitors may be added to the aqueous medium used to prepare the inventive PCA calcium phosphate, or the finished composite or objects made from it may be exposed to inhibitory substance subsequent to fabrication. Suitable such inhibitors include, but are not limited to, magnesium ion, carbonate ion, poly (L-glutamate), polyacrylate, phosvitin, casein, and protein-polysaccharides. Guidance for the use of such compounds can be found in LeGeros in *Monographs in Oral Science* Vol. 15 pp 84–107; LeGeros *Prog. Crystal Growth Charact.* 4:1–45 (19810; and Termine et al. *Arch. Biochem. Biophys.* 140:318–325 (1970), incorporated herein by reference.

The inventive composite may also be used as a drug delivery system by incorporation of a biologically active material into the composite. Further details are found in co-pending application U.S. Ser. No. 08/72,342 entitled "Drug Delivery Device", which is herein incorporated by reference.

Orthopedic and Dental Devices.

The strongly bioresorbable ceramic material may be used in the repair and growth promotion of bony tissue, i.e., as a bone substitute material. In one aspect, an orthopedic or dental implant is introduced into an implant site and is demonstrated to exhibit strong bioresorbability, excellent reossification and bone ingrowth of both cortical and trabecular bone at the implant site. The orthopedic or dental implant of the present invention is comprised of a synthetic, strongly bioresorbable poorly crystalline apatitic calcium phosphate material. In preferred embodiments, it is the material described in co-pending applications U.S. Ser. No. 08/650,764 and/or U.S. Ser. No. 08/446,182, now issued as U.S. Pat. No. 5,650,176, and/or the application entitled "Method and Products Related to the Physical Conversion of Reactive Amorphous Calcium Phosphate", U.S. Ser. No. 08/729,344, each of which is incorporated herein by reference.

The current invention employs a strongly bioresorbable and reossifying PCA calcium phosphate as an implantable bioceramic for the treatment of bone and dental disorders and injuries and other biological applications. The implant is useful in a variety of treatments. By way of example and in no way limiting of the invention, the ceramic material may be applied to bone-contacting surfaces of prosthetic devices, for use as a bone cement. It may be applied directly to bone defects as a filler, where it is capable of promoting the growth of new bone tissue. It may be applied to a tooth socket to avoid problems associated with tooth extraction such as dry socket and/or to provide a fixed substrate on which to anchor a replacement tooth. Alternatively, the PCA material may be used to fabricate fixtures or devices such as screws and plates, which will be resorbed and replaced by bone. When a pharmaceutically active component is added to the composite, such as growth factors or antibiotic, it serves as a drug delivery device. Release of the agent may occur over a long period of time after implantation as the PCA material slowly biodegrades. See, related co-pending application U.S. Ser. No. 08/729,342 entitled "Delivery Vehicle" which is hereby incorporated by reference.

An implant prepared using the inventive PCA material is strongly bioresorbable, that is, at least 80% (preferably 95–99% and most preferably >99%) of the mass of the implanted PCA material is resorbed within one year of implantation. By modifying the characteristics of the PCA material, i.e., porosity, composition, crystallinity, etc., the resorption profile may be modified so that at least one gram (preferably 1–5 grams) of the PCA material is at least 80% resorbed within 12 months, 9 months, 6 months, 3 months or ideally, 1 month, from implantation.

In addition the implant prepared from the inventive PCA calcium phosphate strongly promotes ingrowth of new bone into the implant site. Many current bone implant materials, e.g., bioresorbable organic polymer, merely promote bone apposition at the implant surface. In contrast, the implant of the present invention promotes the growth of new bone within the implant itself. Growth of both trabecular bone and cortical bone (outer bone layer) has been demonstrated to occur. Significant ingrowth occurs within days of implantation. Substantially the entire implant site has been subsumed by new bone within six months, and ideally within one month, of implantation. Weight-bearing bones tend to regenerate bone more rapidly than non-load bearing bones. Thus, ingrowth for the latter may occur somewhat more slowly.

The inventive PCA calcium phosphate undergoes ossification. Ossification refers to the replacement of the implanted synthetic calcium phosphate with bone which histologically is similar or identical to natural bone. Ossification of the inventive PCA calcium phosphate tends to occur in stages with more unorganized bone appearing prior to the establishment of more natural appearing tissue. The inventive PCA calcium phosphate is different from previous bone fillers and cements because bone formation does not occur only at the outer edge of the implant, but initiates simultaneously throughout the implant, presumably in association with the resorptive process. Within two to three weeks following implantation of the PCA material into a load bearing region, such as the tibia or radius, preliminary ossification is observed by the formation of small foci of mineralized osteoid formation (spicules). By four weeks, the spicules have given way to lacy appearing thin cancellous trabecular bone and thin cortical bone. At six weeks, ordered normal or thicker than normal compact cortical bone with lacunae-containing osteocytes is observed. At time points after six weeks, final remodeling occurs so that by twelve weeks the newly ossified bone is indistinguishable from native bone.

Thus, ossification in the presence of PCA calcium phosphate generally reaches completion and appears to occur more rapidly than normal bone growth. This rapid rate of ossification suggests the inventive PCA calcium phosphate enhances bone healing. New bone is observed as early as two weeks and may reach the fully histologically organized state within six weeks, but in any case by 3–6 months. In sheep segmental defect fracture models employing implants of up to 3 gms of hydrated precursor, bone having 100% of the strength of non-fractured bone was found within three months. In the presence of trophic or growth factors such as bone morphogenic proteins this process may be accelerated.

In preferred embodiments, in order to optimize ossification, devices, pastes and putties of the invention may be seeded with bone forming cells. This is most easily accomplished by placing the device (containing PCA calcium phosphate or a hydrated precursor thereto) in contact with a source of the patient's own bone forming cells. Such cells may be found in bone-associated blood or fluids, including exogenous fluids which have been in contact with bone or bone materials or regions, including the periosteum, cortical bone, cancellous bone or marrow. They are also present in tissue including cortical or cancellous bone, bone marrow, endosteum or periosteum. In the case of devices such as screws and pins, the introduction of which into bone is accompanied by bleeding, no further seeding is required. For plates, which oppose only cortical bone, induction of a periosteal lesion which will contact the device is recommended. In yet other embodiments, it will be useful to surgically prepare a seating within the bone by removing a portion of cortical bone at the implant site. Other steps may also be taken to augment ossification, including introduction of bone forming cells harvested from the patient into the graft, or incorporation of trophic factors or bone growth inducing proteins into, or onto the device. Non-autologous bone cells are also within the scope of the invention if the desired amount of bone regeneration occurs prior to host rejection of the bone forming cells. Thus, cells or tissues obtained from primary sources, cell lines or cell banks may all be useful in certain embodiments. Similar considerations apply for cartilage formation and healing and the seeding of the inventive PCA calcium phosphate with chondrocytes and/or other cartilage forming cells.

The implant also prevents deleterious reactions from occurring within the bone gap. For example, fibrous tissue often forms at bone defect sites, which impairs the ingrowth of bone. The implant of the invention is biocompatible and has been demonstrated to reduce the incidence of fibrotic growth at bone defects.

The orthopedic or dental implant of the present invention may be implanted in a patient in a paste or putty form (i.e., as a hydrated precursor). Since the inventive reaction that produces the PCA material can be initiated outside the body, and proceeds slowly at room temperature, the possibility that the material will "set up" prior to application to the surgical site and become unusable is minimized. The reaction accelerates significantly at body temperature and the material hardens in place. This feature is particularly useful in the surgical setting, where custom fitting of the device to the implant location is typically required. Alternatively, the inventive orthopedic or dental implant may be pre-hardened outside the body and implanted at a later time. This approach is useful in those situations where custom shapes are not essential, and where production of large numbers of implants is desired.

Method of application of the implant to bony sites. The implant of the invention may be prepared outside the body in a variety of forms and introduced into the patient at the implant site using methods appropriate to the form of the implant and nature of the malady.

In one embodiment, the implant may be prepared as an injectable paste. A liquid is added to precursor powders to form an injectable hydrated precursor which is capable of in vivo conversion into a bioresorbable PCA calcium phosphate, as described hereinabove. The precise amount of liquid will vary dependent upon the desired consistency of the paste and the nature of the precursor powders used to prepare the PCA material. Typically, about 0.75–1.1 ml liquid per gram powder is used. The paste is desirably injected into the implant site by syringe, preferably using a sixteen or an eighteen gauge syringe. In some embodiments, it may be desirable to prepare the paste ahead of time and to store the paste in the syringe at sub-ambient temperatures until needed. In some embodiments, injection by syringe into a body cavity or intermedullary space may be aided by the use of vacuum to aid in displacing fluids or gases. Most often a vacuum may be applied by insertion of a second needle in the vicinity of the intended injection site. A gentle vacuum may then be applied through the second needle. Application of the implant by injection is particularly desirable for situations in which the material is used as a bone cement to join and hold bone fragments in place or to improve adhesion of, for example, a hip prosthesis. Implantation in a non-open surgical setting is also desirable.

In another embodiment, the implant may be prepared as a formable putty. A liquid is added to precursor powders to form a putty-like hydrated precursor which is capable of in vivo conversion into a bioresorbable PCA calcium phosphate. The precise amount of liquid will vary dependent upon the desired consistency of the putty and the nature of the precursor powders used to prepare the PCA material. Typically, less than about 1.0 ml liquid per gram powder is used. The hydrated precursor putty may be prepared and molded to approximate the implant shape. The putty may then be pressed into place to fill a gap in the bone, tooth socket or other site. Use of a bone putty may be particularly desirable in repair of bone defects in non-union bone or other situations where the gap to be filled is large and requires a degree of mechanical integrity in the implant material to both fill the gap and retain its shape.

In yet another embodiment, dry precursor powders may be applied directly to a bone defect. Hydration and conversion of the precursor into the PCA material occurs at the bone defect site by direct exposure to blood or other physiological fluids. Such application may be particularly desirably where the bone defect is accompanied by excessive bleeding. The hydroscopic nature of the precursor powders serves to absorb body fluids, provide a physical barrier to protect the wound site and to provide a bone substitute material which promotes bone in growth at the defect site.

In still yet another embodiment of the invention, the implant may be prepared from a prehardened PCA calcium phosphate which has been shaped into the desired form. This may be accomplished by preparing a hydrated precursor as a putty or paste as described above, injecting or pressing the hydrated precursor into a mold, and allowing the precursor material to convert and harden into the PCA calcium phosphate. Alternatively, the PCA calcium phosphate may be prepared as a solid block or other such geometry and shaped into the desired object using drills or other such shaping tools known in the art. This method is particularly desirable for production of resorbable objects such as anchors for tooth implants, spacers for cervical fusion, resorbable screws and plates, and slowly resorbable shapes for augmentation.

Orthopedic and dental implants. The implants described hereinabove may be useful in the treatment of a variety of orthopedic and dental disorders. The materials used in the preparation of the implant are desirably sterile and may be sterilized using conventional techniques, including by not limited to gamma irradiation, filtration, and ethylene oxide.

Healing of bone fractures and defects. PCA calcium phosphate may be used to join two or more bone pieces together and/or to improve healing of bone fractures by filling the gap left by the fracture, or space caused by compressive damage as a result of the fracture.

In the situation involving non-union bone fractures, the implant can be used to stabilize the bone defect because the implant hardens in place in vivo. The implant of the invention is especially advantageous in that the bone gap can be filled without open surgery. To this end, the bone defect site may be observed by x-ray to ensure proper positioning of the injection needle. The implant may then be directly injected into the defect site. X-ray or MRI visualization may be used, if desired, to confirm placement. FIG. 19 is a pictorial illustration of application of the implant to a tibial defect in which the implant material is injected into the bone defect. When the gap is particularly large, it may be desirable to first immobilize or "fix" the defect and then fill the gap with implant material. The defect may be fixed using conventional fixation devices, such as titanium screws, pins and plates. In preferred embodiments, the defect is fixed with screws or plates prepared from hardened PCA material and/or composites thereof, which are themselves bioresorbable and hence allow complete bone ingrowth at the defect site and require no post surgical treatment to remove the hardware.

In the situation where the bone has been crushed or fragmented, the bone fragments may be reassembled and the implant material may be used to hold them in place while a bone matrix regrows at the fracture site. FIG. 20 is a pictorial illustration of a fragmented bone which has been reassembled. Hydrated precursor paste is injected around the bone fragments which are held rigid once the paste converts into PCA calcium phosphate. Bone regrowth occurs to regenerate bone tissue and imbed original bone fragments in new bone matrix.

The implant may also be used to heal compression fractions, such as compression of the tibia. The cortical bone surface can be re-aligned and fixed in place using mechanical fixation and the implant can be used to fill the void created by the compressive destruction of the bone.

In yet another embodiment of the invention, the PCA calcium phosphate implant may be used to secure pins, screws and other more complicated prosthesis devices which are used to hold bone in place. By immobilizing the fracture using hardware and embedding the hardware in PCA paste, potential voids are filled, thereby expediting new bone formation around the screw. In addition, the implant acts to distribute the force of the screw across a greater surface area, thereby reducing the likelihood of pull out or early bone resorption. This approach is used most often in repair of broken hip bones, where a hip prosthesis is used to reinforce the weight-bearing femoral neck of the femur.

Where it is desired to minimize surgical intervention, it is preferred to use the PCA material as a paste and to introduce the implant by syringe into the bone defect. Of course, where minimal intervention is not an issue, i.e., during open surgery, the implant may be used as a putty. Indeed, this may be preferred in some circumstances as the added formability of the PCA putty gives the physician increased control over the final shape of the implant device and improves implant conformity with neighboring bone surfaces.

Treatment of osteoporosis. As bones age, they lose mass, thereby becoming more porous and brittle. PCA implant material may be used to promote bone growth and to densify the bone. FIG. 21 includes a pictorial illustration of a normal bone 60 having a regular and dense network of trabecular bone. FIG. 21 also illustrates osteoporotic bone 62 in which significant bone mass has been lost. Osteoporotic bone may be treated with reossifying PCA material of the invention to densify the bone and protect against bone fracture and failure. Bone strength density may be improved by injecting hydrated precursor paste into the bone interior. The precursor serves to improve bone in several ways. Firstly, the hydrated precursor hardens into PCA calcium phosphate which is strong and serves to reinforce the already brittle bone. Secondly, the PCA calcium phosphate is a biocompatible matrix accommodating and stimulating new bone growth, so that as it bioerodes, new bone is formed to replace it. Thirdly, the eroding PCA calcium phosphate is a source of bioavailable calcium for osteoblasts to use in the formation of new bone.

The implant may be particularly effective in preventing the collapse of vertebrae. FIG. 22 is a pictorial illustration of a portion of a spinal column including vertebrae 70, 71, 72 and discs 73, 74. Vertebra 70 is healthy, and exhibits dense trabecular bone matrix. Vertebra 72 is an osteoporotic vertebra which has been crushed due to increased porosity and reduced bone density. Vertebra 71 is an osteoporotic vertebra undergoing implantation of PCA calcium phosphate to strengthen bone and regenerate bone mass.

Spinal and cervical fusion. As a general rule, when discs and vertebral bodies are removed for the treatment of degenerative disease, trauma or tumor, they need to be replaced with a structural graft to maintain the patient's cervical alignment. Bone graft is usually placed as a spacer between vertebrae to facilitate fusion of vertebral bodies and to restore height. Conventional spacers, some of which are known as "cages" are made from titanium or autologous or allograft bone. However each of these prior art devices have disadvantages. Autologous bone may not always be available, allograft bone carries the risk of infection and pathogen exposure, and titanium is not resorbed by the body and either remains or must be surgically removed.

To overcome these disadvantages of the prior art implants, PCA calcium phosphate may be used as a spacer in cervical fusion procedures. The PCA calcium phosphate is prepared as a disk or shim. The PCA calcium phosphate disk may be used as a hardened, slowly resorbing spacer for the fusion of adjacent vertebrae. In preferred embodiments, the spacer is in the form of a hollow ring. The center of the ring may be filled with a PCA calcium phosphate formulated for rapid bioresorbability and bone ingrowth.

Spinal fusion is also done across lateral processes. See, for example, *Sandhu* et al, Spine, vol 20: 2669–2682, 1995.

Prostheses. Prostheses for joint replacement, particularly hip replacement are widely used and can substantially improve the quality of life for the patients receiving them. However, current cementing techniques are unable to prevent all "micromotion" and gaps between the prosthesis and the natural bone receiving the implant, resulting in increased incidence of loosening and failure of the joint replacement over time with concomitant pain or discomfort to the patient.

FIG. 23 is a pictorial illustration of a hip prosthesis being secured firmly into natural bone using PCA calcium phosphate as a bone cement. Thus, the hip ball and socket may be positioned in the natural bone in spaces prepared to received them. Once positioned, the hydrated precursor paste may be injected around the prosthesis to fill gaps between the bone wall and the prosthesis and to firmly cement the prosthesis to the patient's own bone. Alternatively, the bone surface may be coated with the hydrated precursor and the prosthesis may be inserted into position in the PCA material-coated bone. The hydrated precursor hardens and sets to thereby firmly anchor the prosthesis into place. In both scenarios, the PCA material slowly bioresorbs and is replaced by natural bone; thus, gaps and micromotion associated with the prosthetic device are minimalized.

In another embodiment, the prosthesis may be coated with the PCA material. Thus, a hydrated precursor may be applied to the surface of the prosthesis outside the body and is allowed to harden and convert to PCA calcium phosphate. The coating facilitates acceptance by the host of the prosthesis and promotes bone growth on the prosthesis surface.

The present implant material may also be used as an in vivo treatment of previously implanted prosthesis devices which have formed cysts at the prosthesis-bone interface. The cyst may be removed by conventional techniques, but this procedure often leaves large gaps adjacent to the prosthesis. These gaps may be filled by injection of the implant material of the invention into the gap.

Replacement material for autologous bone implants. For various reasons, the PCA material may not be preferred for use as an implant and the patient's own bone is preferred (e.g. autologous bone harvested from the patients own iliac crest). This is often the case in the treatment of bone cancer. However, the PCA material may be used at the bone removal site to rapidly promote bone regrowth at the bone harvesting site to prevent cosmetic deficiencies or create new bone for future use.

Reconstructive plastic surgery. Prehardened PCA calcium phosphate in the desired shape may be attached using hydrated precursor paste. Alternatively, a hydrated precursor paste may be formed and shaped in vivo and secured in place using hydrated precursor paste. Where synthetic bone graft is medically inappropriate, the patient's own bone may be harvested and secured at the implant site using a hydrated precursor paste or putty. As described previously, the precursor is converted into PCA calcium phosphate which is gradually resorbed and which promotes new bone growth within the implant site in preferred embodiment existing periosteum is drawn over the implant surface prior to closure.

Periodontal defects. PCA calcium phosphate may be used as an implant in teeth sockets to avoid the problems associated with teeth extraction, such as dry socket, infection and fibrous growth. FIG. 24 is a pictorial illustration of a tooth socket receiving an implant by injection. The implant converts into PCA calcium phosphate and is replaced with new bone within six months, preferably within six weeks and ideally as fast as three weeks. The new bone provides an enhanced surface in which to implant dental prosthesis (replacement teeth).

Alveolar ridge defects. When, through trauma, congenital abnormalities or illness, bone loss occurs to the jaw section containing the teeth sockets (alveolar ridge), rebuilding of the ridge may be needed before dental prosthetic implantation can occur. The management of alveolar ridge deficiencies poses a challenge because the magnitude of the osseous defects are often greater than that resulting from tooth extraction and may require replacement (or regrowth) of a significant amount of bony tissue.

The conventional procedure may call for nasal floor elevation, bone grafting and bone regeneration. Bone generation prior to dental prosthesis implantation has the advantage of providing a greater bone mass for implantation and hence improved implant alignment and strength. However, the process typically occurs in staged intervals because of the length of time conventional bone regeneration requires in order to develop bone of sufficient strength to handle the bone implant. Thus, a two step technique has the disadvantage of long healing time before implant placement (ca. nine months) and poor bone quality of the regenerated tissue. See, C. M. Misch and C. E. Misch *Implant Dentistry* 4(4): 261 (1995).

The implant of the present invention allows the build-up of the alveolar ridge and dental implantation to occur over a much shorter time and often in a single step. The implant is introduced as a paste or putty to the ridge site, where it sets up and hardens in situ. Within hours or even minutes, the implant is sufficiently hard to accept the dental implant. Within six months, the implant will gradually regenerate natural bone, thereby bonding the dental implant into a hard bony site. Thus, ridge augmentation and dental prosthesis implantation may occur at the same time or within days of one another. The dental implant may also be introduced into the hydrated precursor prior to hardening. The inventive PCA calcium phosphate may also be injected into the implant in conjunction with traditional methods to increase bone ingrowth to and around the dental implant.

Likewise, the implant of the present invention may be used to augment the ridge alongside the nasal cavity, where natural bone may be too thin to accept the prosthesis. Thus, as pictorially illustrated in FIG. 25, a hole may be drilled into the alveolar ridge adjacent to the sinus cavity, the sinus sac may be raised and implant material is introduced into the site by injection and allowed to harden. With hardening and ossification, the ridge is ready for dental prosthetic implantation.

Use as a hemostatic agent. The dry precursor powder may also be applied dry as a hemostatic or absorptive agent. Once in contact with body fluids the material hydrates and then hardens in place similarly to the hydrated precursors prepared ex vivo. This property is particularly useful to control bleeding in both hard and soft tissues alike. In one application the material is applied to the opening following spinal taps or spinal surgery to form a patch and prevent CSF leaks.

Cranial repair. Cranial repair has presented a particular problem due to the slow healing of bone involved in reconstructive surgery of the cranium. The inventive PCA material may be used both to repair and to stimulate the growth of cranial bone. Additionally, growth factors or osteogenic cells may be included in the implant to further stimulate healing.

Cartilage growth. PCA calcium phosphate implants may be used to promote new cartilage growth. Cartilage forming cells (e.g. primary chondrocytes, or chondrocytic cell lines) may be used with the implant. The implant provides a matrix for cell growth and proliferation as well as a connecting means to other tissue surfaces (e.g. bone or cartilage).

To this end, the cartilage sac is ruptured and PCA calcium phosphate is injected into the cartilage site. The PCA material desirably contains chondrocytes which promote cartilage growth. For further information of cell seeding of tissue matrices, see "Cell Seeding of Ceramic Compositions", U.S. Ser. No. 08/729,354, which is hereby incorporated by reference.

Bone distraction. The PCA calcium phosphate of the invention is useful in a procedure known as bone distraction. Bone distraction is an orthopedic operation that ultimately lengthens the bone. In this procedure, the bone is cut and gradually parted using orthopedic clamps. PCA material may be transdermally injected or surgically implanted to fill the bone gap produced by expansion of the bone. When used in this application, PCA calcium phosphate promotes bone growth and repair. Because the PCA material serves as both scaffold and calcium source, the distraction rate may be significantly accelerated over previous methods. The maximum distraction rate using current practices is limited to approximately 1 mm/day. Using PCA calcium phosphate, the distraction rate can be increased to greater than that, in some instances up to 2–5 mm/day.

Temporary bony structures. The implant of the invention may be used in other than bony sites in the body. For example, an implant may be prepared from PCA calcium phosphate to be used as a protective structure for various organs of the body. According to the invention, the PCA material may be used to support, shield or frame sensitive organs. By way of example, the PCA material could be prepared outside the body as a hardened vascular stent in the treatment of heart disease or as a gastrointestinal stent in the treatment of Krone's disease. Alternatively, the implant can be used to provide temporary support for sutured or stapled repairs, bypasses, or organ or tissue transplants and implants. The hydrated precursor may be placed around the structure in need of support, where it hardens in place providing support or mechanical protection until resorption occurs.

The resorbable nature of the inventive PCA calcium phosphate as well as its ability to benignly interact with and adsorb proteins, nucleic acids, and other substances make it an ideal substance for use as an implantable depot for use in the delivery of therapeutic substances to the body. In general, the main requirement is that the agent to be delivered remains active in the presence of the vehicle during fabrication and/or loading, or be capable of subsequently being activated or reactivated. The stability and/or compatibility of a particular agent with the inventive material, as well as fabrication strategies, may be tested empirically in vitro. Some representative classes of useful biological agents include organic molecules, proteins, peptides, nucleic acids, nucleoproteins polysaccharides, glycoproteins, lipoproteins, and synthetic and biologically engineered analogs thereof.

In one aspect of the invention, bone regenerative proteins (BRP) are incorporated into the inventive PCA calcium phosphate. BRPs have been demonstrated to increase the rate of bone growth and accelerate bone healing. A bone graft including the inventive PCA calcium phosphate and BRP is expected to promote bone healing even more rapidly than a bone graft using the PCA calcium phosphate of the present invention alone. The efficacy of BRP is further enhanced by controlling PCA calcium phosphate resorption such that it dissolves at a rate that delivers BRP, calcium, and phosphorus at the optimum dosage for bone growth. Such a method of incorporating BRP would include, but not limited to, mixing a buffer solution containing BRP with its optimum pH that would maintain protein activity, instead of distilled water. Exemplary BRPs include, but are in no way limited to, Transforming Growth Factor-Beta, Cell-Attachment Factors, Endothelial Growth Factors, and Bone Morphogenetic Proteins. Such BRPs are currently being developed by Genetics Institute, Cambridge, Mass.; Genentech, Palo Alto, Calif.; and Creative Biomolecules, Hopkinton, Mass.

In another embodiment of the invention, it is contemplated to incorporate antibiotics or other agents into the amorphous calcium phosphate and its mixture. From a clinical sense, one of the major implication arising from a bone-graft surgery is a need to control the post-operative inflammation or infection. A bone graft including the inventive PCA calcium phosphate and antibiotic(s) is expected to reduce the chances of local infection at the surgery site, contributing to infection-free, thus faster bone healing process. The efficacy of antibiotics is further enhanced by controlling their release from the PCA calcium phosphate delivery vehicle by regulating the resorption rate such that it dissolves at a rate that delivers antibiotic peptides or its active component at the most effective dosage to the tissue repair site. Exemplary antibiotics include, but are in no way limited to, Penicillin, Chlortetracycline hydrochloride (Aureomycine), Chloramphenicol and Oxytetracycline (Terramycine). Both antibiotics, mostly polypeptides, and bone regenerating proteins may be intermixed with the PCA calcium phosphate material of the present invention, to locally deliver all or most of the necessary components in facilitating optimum condition for bone tissue repair.

Non resorbable apatitic bone fillers and cements may also be prepared by the methods of the current invention by promoting the conversion of ACP to a more crystalline state than PCA calcium phosphate. In general use of more hydroxyapatite stoichiometric Ca/P ratios decrease use of crystallization inhibitors, and crystallization piomoting conditions such as elevated temperatures will tend to drive the conversion to a more crystalline product.

Solid PCA Calcium Phosphate Devices.

In another application of the invention, solid PCA calcium phosphate compositions are prepared, either in vivo or ex vivo. The first method of making a solid is to compress the unreacted precursors of the PCA material. ACP converts to PCA calcium phosphate once the pellet has been exposed to an aqueous environment (e.g. in vivo implantation). The second method of production involves compressing already converted PCA granules into a desired shape. The material can also be formed by any other pellet fabrication method known in the pharmaceutical industry. Once the shape has been fabricated, it can be modified in the following ways: A coating can be added to the shaped material. Therapeutic substances are absorbed to the solid material. There can also be further modification of the shape and texture of the pellet. Sterile pellets may be prepared through the use of presterile components or by terminally sterilizing the pellet. All variations to the solid PCA calcium phosphate are considered within the scope of the present invention.

Methods of Pellet Production. In one embodiment, compressing the unreacted precursors of the PCA material produces the prehardened pellet. The first component is an amorphous calcium phosphate. The second component is the promoter. The preferred promoter is dicalcium phosphate dihydrate (DCPD). In other cases, the promoter may be other calcium phosphates such as crystalline HA. The two components are compressed and molded into the desired shape by any suitable method. Preferred embodiments of compression and molding include hand-held presses and hydraulic presses as described in examples 32 and 33. The pressure of the compression is dependent on what characteristics are desirable for the pellet. For instance, lower pressures are favorable for a pellet that is quickly resorbable. Other methods of pellet fabrication known in the pharmaceutical industry are also acceptable. The compressed object of desired shape most preferably reacts endothermically at 37° C. in vivo to form PCA calcium phosphate. A conversion of ACP in the presence of a promoter occurs under these conditions during this reaction to form PCA calcium phosphate.

In another embodiment, PCA calcium phosphate is formed in vitro. An amorphous calcium phosphate in the presence of a promoter and a limited volume of aqueous medium is converted to poorly crystalline apatitic calcium phosphate. In the most preferred embodiment, the PCA material is hardened at 37° C. Once the PCA material is a solid, it is lyopholized. The dry material is then ground for a specified amount of time in a grinding chamber. Other methods of grinding, such as a mortar and pestle, are also acceptable. The powder is then formed into a pellet or other desired shape by the methods described above.

PCA material may also be prepared by combining an amorphous calcium phosphate with a promoter and a biologically suitable aqueous medium. At this time, the PCA material, as a paste or putty consistency, is molded by any suitable method into the desired form. Once the material is molded, it is then hardened most preferably at 37° C. A range of temperatures below and above 37° C. is also acceptable. Once the molded object is a solid, it is then lyopholized. The object is lyophilized because the presence of water in the pellet may cause the material to be more unstable and have a tendency to become more crystalline.

Once the PCA material is produced, it is formed and hardened, and then lyopholized as described previously. In some instances, it may be unstable and tend to become more crystalline and eventually converts to hydroxyapatite. The prepared solid PCA calcium phosphate can then be stored either wet or dry. Stability issues surrounding the storage of PCA material include temperature, lyopholization, the use of inhibitors, and whether the material is wet or dry. Lyophilization improves the stability of the PCA material because the presence of water is cause for the conversion reaction. Lower temperatures will enable the PCA material to be more stable when compared to the stability at room temperature or in vivo. Ideal conditions include dry storage of pellets at room temperature with no exposure to moisture. The PCA material can also be stored in an aqueous medium for up to 30 days, at room temperature, and pH=7. FTIR and XRD analysis may be conducted on the PCA material to monitor the stability of the PCA material during the storage period. The presence of peaks at 563 cm-1, 1034 cm-1, 1638 cm-1, and 3432 cm-1 (FTIR) should remain unchanged.

Medical Uses of Pellets. The solid PCA calcium phosphate material can be used in many different applications, depending on the details of the situation. The first application applies to orthopedic implants. Pellets, plates, screws, granules, bone void fillers and other forms are appropriate for orthopedic applications. The pellets, plates, and screws can be of various shapes and sizes.

Bone void fillers are gently packed into voids in the bone, which are—surgically created defects or defects created from traumatic injury, tumors or other diseases. Sand grain granules (1–2 mm) of PCA calcium phosphate can also be used in additional hard tissue sites. The granules are particularly useful in alveolar ridge repair and hairline fractures. However, other applications include, but are not limited to tibial fractures, maxillo and cranial indications, extraction socket voids, and later spinal fusion. A significant advantage to granules is that they can be arranged to fit into small areas where bone regeneration is needed. Also, the sand size granules are used to anchor prosthetics since they can shift and settle into the areas where implanted and serve to hold the various medical devices in their proper locations. In addition, the pellets can be mixed with PCA paste for implantation purposes. The use of these solid resorbable implants also eliminates the need for metal implants in the body.

A second application for solid PCA calcium phosphate is to provide support matrices for living tissues. These matrices can be used to promote cell growth, cell transplant and cell therapy. By supplying the appropriate cells onto the support matrix of prehardened PCA material, the cells are effectively delivered to the desired implait site. Cells may be seeded into the PCA in vitro or in vivo depending on what is appropriate for the given indication. The use of living cells in the body promotes self-healing through tissue regeneration.

The porosity of the solid PCA material implants is an important aspect for the ingrowth of cells to regenerate bony tissues. Since the support matrices are comprised of PCA material they are also fully resorbable in the body, therefore the implanted matrix initiates cell growth while it is being resorbed.

Yet, another, third application for the solid PCA material is as a delivery vehicle. Solid PCA calcium phosphate can be used in association with antibiotics, vaccines, bone morphogenetic proteins or other medicinally useful substances. Each biologically active agent can be added in the precursor stage of fabrication, or after the conversion reaction has taken place. The pellet may also be dipped or otherwise coated with the factor to be delivered.

Variations of Use. Prehardened PCA calcium phosphate can be altered to accommodate other variations for a bone substitute material. The first alternative is to use PCA material in a composite. Substances such as binders, polymers, fillers, and coatings as well as others are added to the PCA material to change the physical and/or mechanical properties of the material. Binders and polymers added to PCA to alter its mechanical and resorptive characteristics. Fillers will allow the PCA calcium phosphate to be shaped into pellet form with lower compressive forces. Binders and fillers also add strength, bulk, and adhesion to the PCA material. After the addition of a filler or binder, it may not be necessary to compress the material into a pellet form since the filler or binder may provide enough scaffolds to form a solid matrix. Coatings on the PCA material provide a buffer to the material and protect the inner surface from moisture exposure, which would eventually cause a conversion from ACP to PCA.

In the preferred embodiment, the PCA materials are replaced by bone following implantation. Replacement of the solid PCA by tissues other than bone may be induced through the seeding of the PCA with stem cells or committed stem cells or precursors to other tissues such as cartilage. In addition, characteristics of the implant site will also dictate the replacement tissue (e.g., reduced oxygen leads to chondrogenesis).

Additionally, a third alternative variation of the production method of PCA calcium phosphate is to vary the promoter. The promoter takes on different roles depending on th desired result.

The invention is further exemplified with reference to the following examples, which are presented for the purpose of illustration only and are not to be considered as limiting of the invention.

EXAMPLE 1

Production of PCA calcium phosphate using an ACP and participating promoters. This example demonstrates the hardening properties and PCA calcium phosphate formation from ACP using a number of different participating promoters. Highly reactive ACP was prepared according to Example 5.

The nanocrystalline hydroxyapatite of samples 1-1, 1-2 and 1-3 were prepared without inhibitors of crystallization as follows: 218 g of disodium hydrogen orthophosphate ($Na_2HPO_4 \cdot 12H_2O$) were dissolved in 1200 mL of solution of distilled water. For carbonated PCA calcium phosphate of samples 1-1 and 1-2, 80 g of $NaHCO_3$ were also added to this solution. 70 g of calcium nitrate [$Ca(NO_3)_2 \cdot 4H_2O$] were dissolved in 500 mL of distilled water. The calcium solution was quickly poured into the phosphate solution at room temperature with constant stirring. Precipitation was immediate and substantially complete. The pH of the precipitate was adjusted to 7.4 by the addition of sodium hydroxide solution in order to avoid the formation of acidic calcium phosphates. The precipitate was immediately separated from the solution by filtration through a Buchner filter (with a total surface about 0.1 sq.m), and was washed by about 3 liters of distilled water. A gel cake of low crystallinity calcium phosphate was obtained on the filter paper. A portion of the gel cake was immediately lyophilized for samples 1-2 and 1-3.

For sample 1-1 the gel cake was treated as follows: After filtration and washing, an appropriate amount of distilled water (5 to 80 weight %) was added to the gel precipitate. The gel was homogenized by whipping energetically for a few minutes. It was then cast into polytetrafluoroethylene (PTFE) molds (diameter 60 mm; height 2 mm), and sonicated for a few minutes in order to release the air bubbles trapped in the gel.

The molds were dried in a chamber at controlled temperature (5 to 37° C.) and humidity (10 to 95% RH). The samples shrank slowly on drying and released most of their water. The rate of drying and the shrinkage of the samples depended on the initial water content. The material hardened on drying and became glassy. It contained about 10% of residual water.

The remaining hydroxyapatites and calcium sources were used as is from commercial sources.

TABLE 1

ACP Conversion Using Participating Promoters

| sample | participating promoter | incubation at 37° C. | extent of hardening | PCA* by FTIR | PCA* by XRD |
|---|---|---|---|---|---|
| 1-1 | carbonated nanocrystalline hydroxyapatite, air dried | 30 min<br>2 hrs | starting to set<br>hard | yes | ND |
| 1-2 | carbonated nanocrystalline hydroxyapatite, lyophilized | 30 min<br>2 hrs | hard<br>hard | yes | yes |
| 1-3 | non-carbonated nanocrystalline hydroxyapatite, lyophilized | 30 min<br>2 hrs | starting to set<br>hard | yes | ND |
| 1-4 | Aldrich hydroxyapatite grain size <15–30 μm | 30 min | hard | yes | yes |
| 1-5 | Clarkson hydroxyapatite grain size >250 μm | 30 min | starting to set | yes | ND |
| 1-6 | Monetite - non calcinated grain size | 30 min<br>15 hrs | soft<br>starting to set | yes | ND |
| 1-7 | $CaCO_3$ | 30 min<br>15 hrs | starting to set | yes | ND |
| 1-8 | $Ca(OH)_2$ | 30 min<br>15 hrs | soft<br>starting to set | yes and $Ca(OH)_2$ | ND |
| 1-9 | $Ca(CH_3COO)_2$ | 30 min<br>15 hrs | soft<br>soft | yes | ND |

*PCA = poorly crystalline apatitic calcium phosphate
ND = analysis not done

Figure 14:
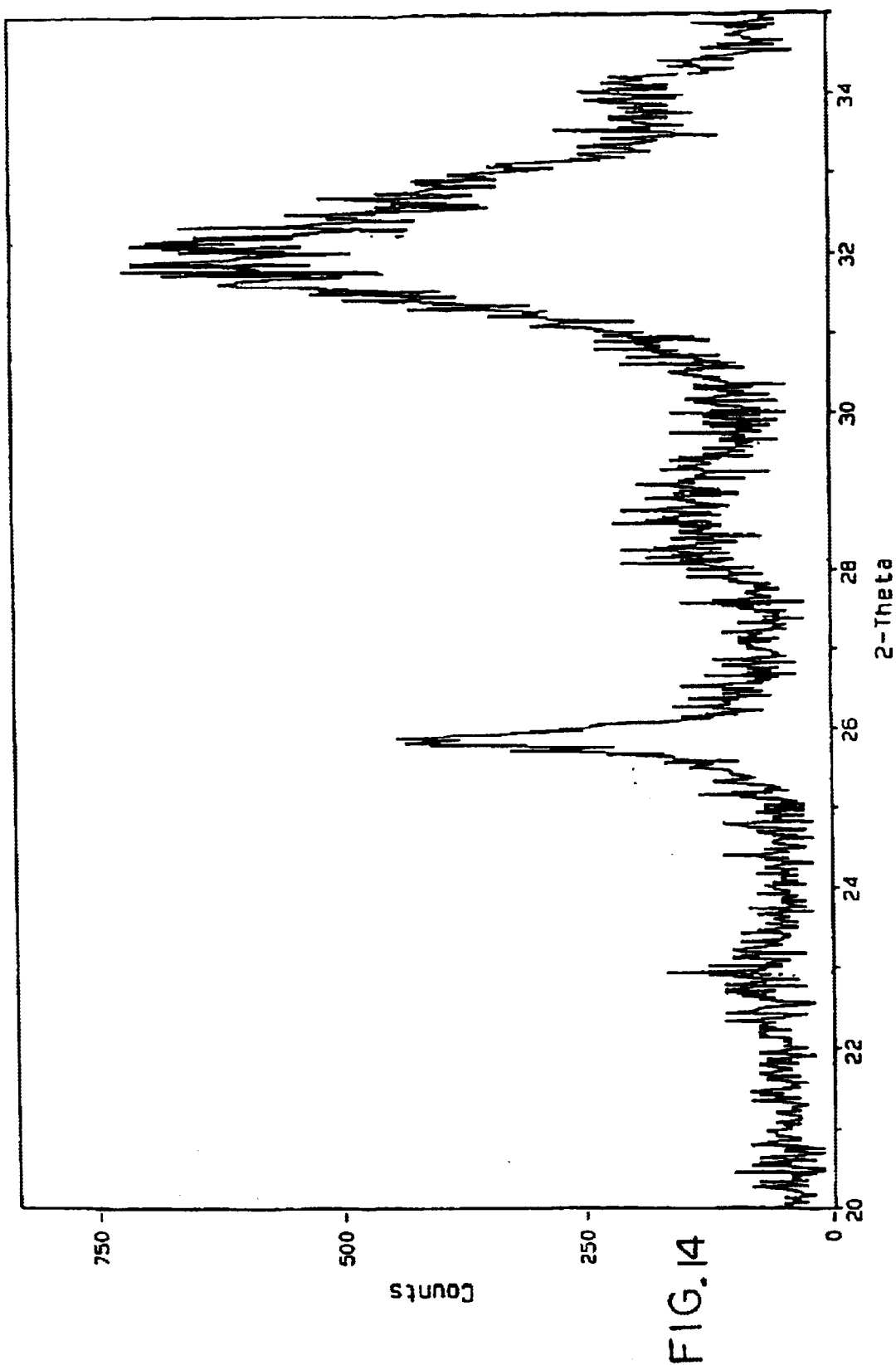
FIG. 14 is an X-ray diffraction pattern of PCA calcium phosphate prepared as described in Example 1–2.
Figure 15:
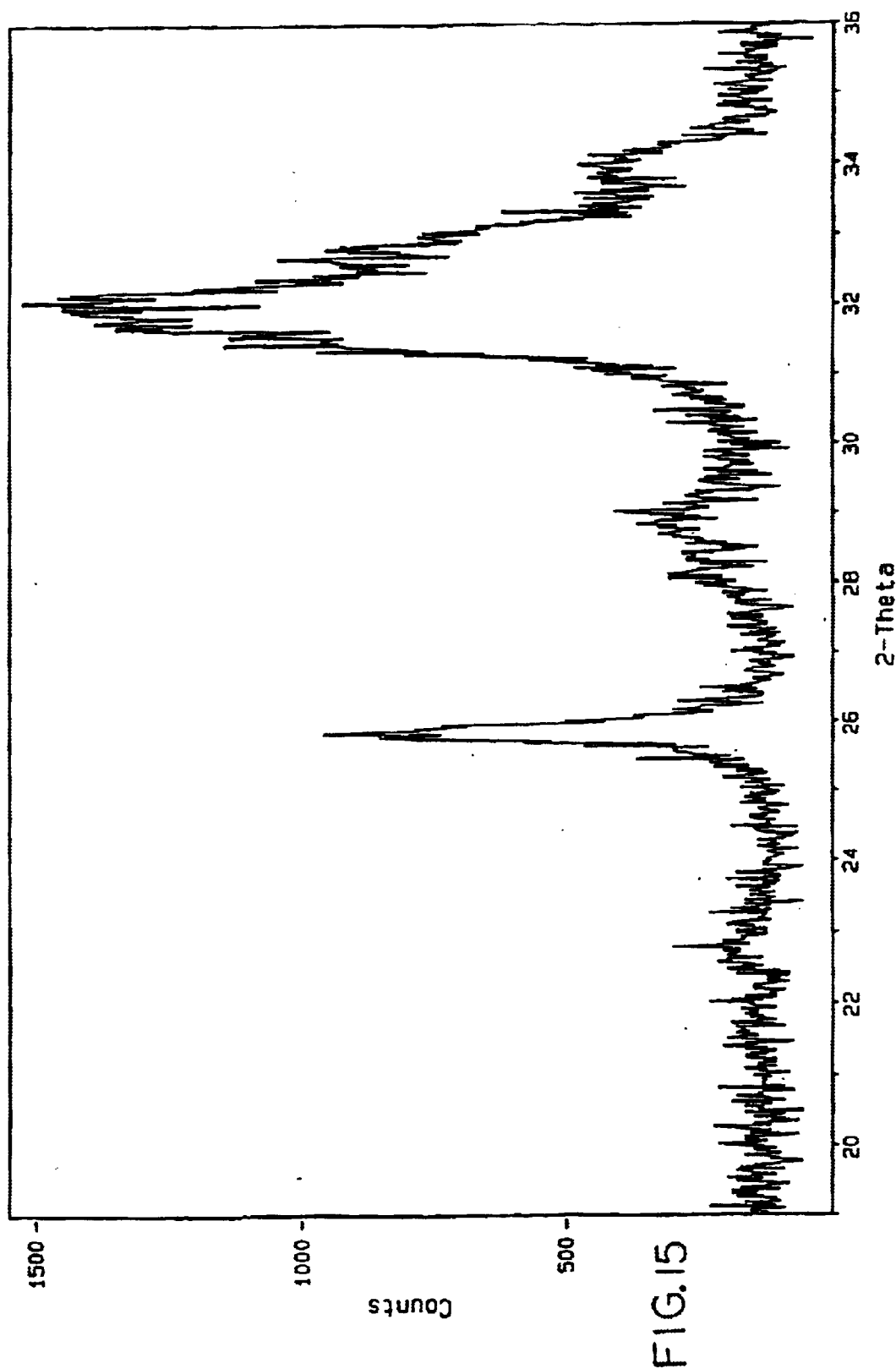
FIG. 15 is and X-ray diffraction pattern of PCA calcium phosphate prepared as described in Example 1–4.

ACP was mixed with the specific promoter at a ratio (wt/wt) of about 50:50 (see Table 1) for 5 minutes in a SPEX laboratory mill. Approximately 0.8 mL $H_2O$/g dry powders were added to the dry precursor mixture and mixed to a paste. The mixture was then shaped into a ball, wrapped in moist tissue paper and heated to 37° C. for at least 30 minutes. After 30 minutes and at various time points thereafter the paste was monitored for hardness. FIGS. 14 and 15 are representative XRD from reactions 1-2 and 1-4. The use of two different grain size hydroxyapatites as participating promoters yielded similar results as with different grain size DCPDs (see Example 10) That is, the larger grain size hydroxyapatite hardened more slowly and less completely than the smaller grain size hydroxyapatite.

EXAMPLE 2

This example demonstrates the use of a neutral apatitic calcium phosphate as a promoter for the conversion of ACP to the inventive PCA calcium phosphate to promote bone growth in vivo. Stoichiometric hydroxyapatite is mixed with reactive ACP as described in Example 1–4. Hydrated precursor paste is applied to animal subjects as described in Examples 15, 16 or 19. Bone healing and biocompatibility is monitored as described at the time points indicated.

EXAMPLE 3

This example demonstrates the production of PCA calcium phosphate from ACP using a number of different passive promoters.

Figure 13:
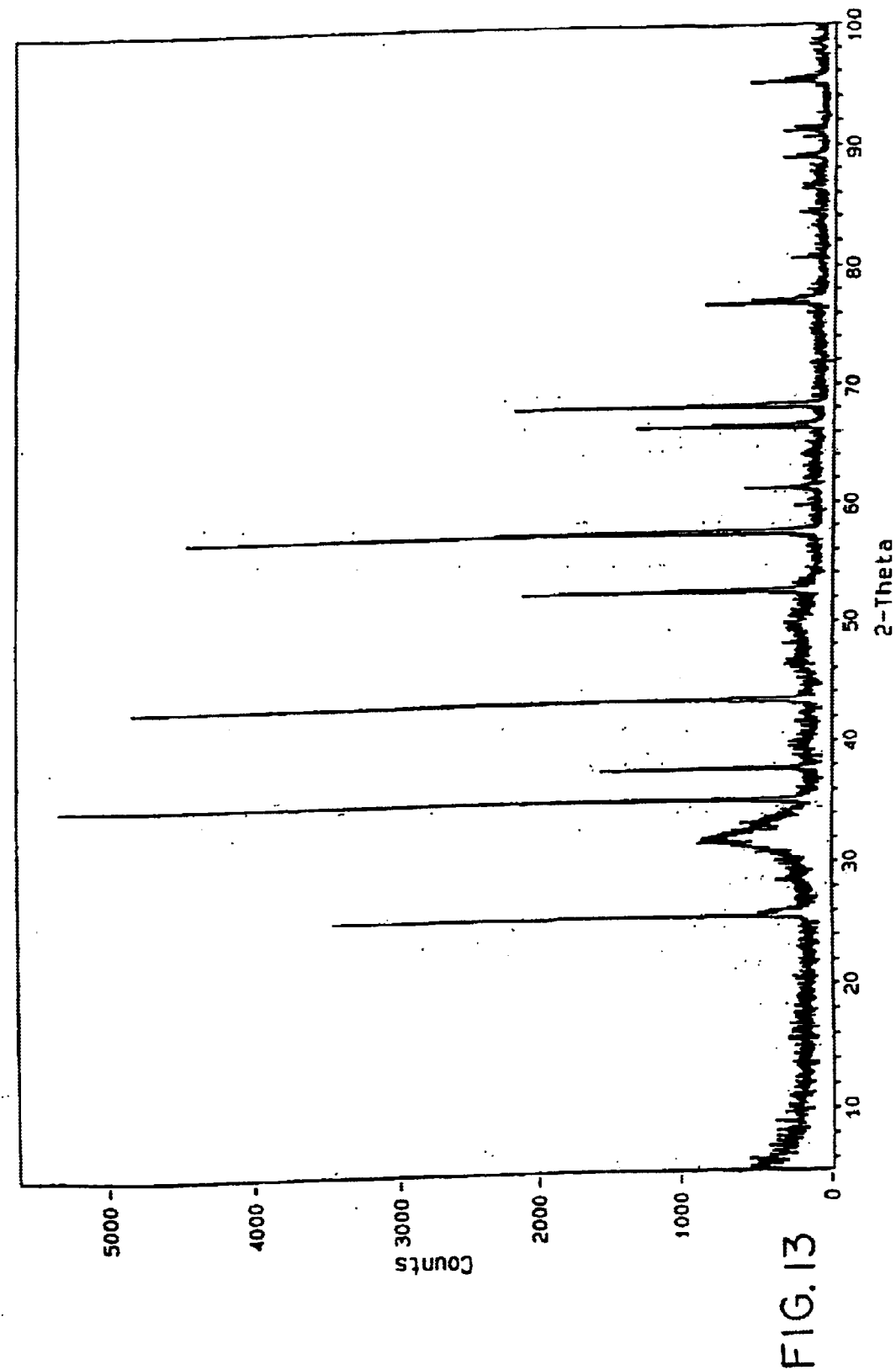
FIG. 13 is an X-ray diffraction patterns of PCA calcium phosphate prepared from $Al_2O_3$ passive promoter, in which $Al_2O_3$ peaks are indicated by lines.

Highly reactive ACP was prepared according to Example 5. ACP was mixed with the specific promoter at a ratio (wt/wt) of about 5:1 or 1:1 (see Table 2) for 5 minutes in a SPEX laboratory mill. Water (0.75–0.85 mL) was added and mixed to form a putty. The mixture was then formed into a ball, wrapped in moist tissue paper and heated to 37° C. for at least 30 minutes. After 30 minutes and at various time points thereafter the paste was monitored for hardness. FIG. 13 is a representative XRD from sample 2–4 employing an alumina promoter. In this figure the alumina peaks can be seen superimposed over the standard PCA calcium phosphate profile.

TABLE 2

ACP Conversion Using Passive Promoters

| study # | Passive Promoter (ACP:promoter) | Incubation time at 37° C. | Extent of Hardening | PCA* by FTIR | PCA* by XRD |
|---|---|---|---|---|---|
| 2-1 | SiO$_2$ (5:1) | 30 min | soft | yes | yes |
|  |  | 3 hrs | very hard |  |  |
| 2-2 | Mica (5:1) | 30 min | soft | yes | yes |
|  |  | 12 hrs | very hard |  |  |
| 2-3 | Al$_2$O$_3$ (1:1) | 30 min | soft | yes | yes |
|  |  | 12 hrs | very hard |  |  |
| 2-4 | Al$_2$O$_3$ (5:1) | 30 min | soft | yes | yes |
|  |  | 12 hrs | very hard |  |  |

*PCA = poorly crystalline apatitic calcium phosphate

EXAMPLE 4

This example demonstrates the use of a scanning differential calorimeter (DSC) to monitor temperature sensitivity and the net endothermic nature of a preferred embodiment reaction employing activated ACP and DCPD precursors.

Figure 16:
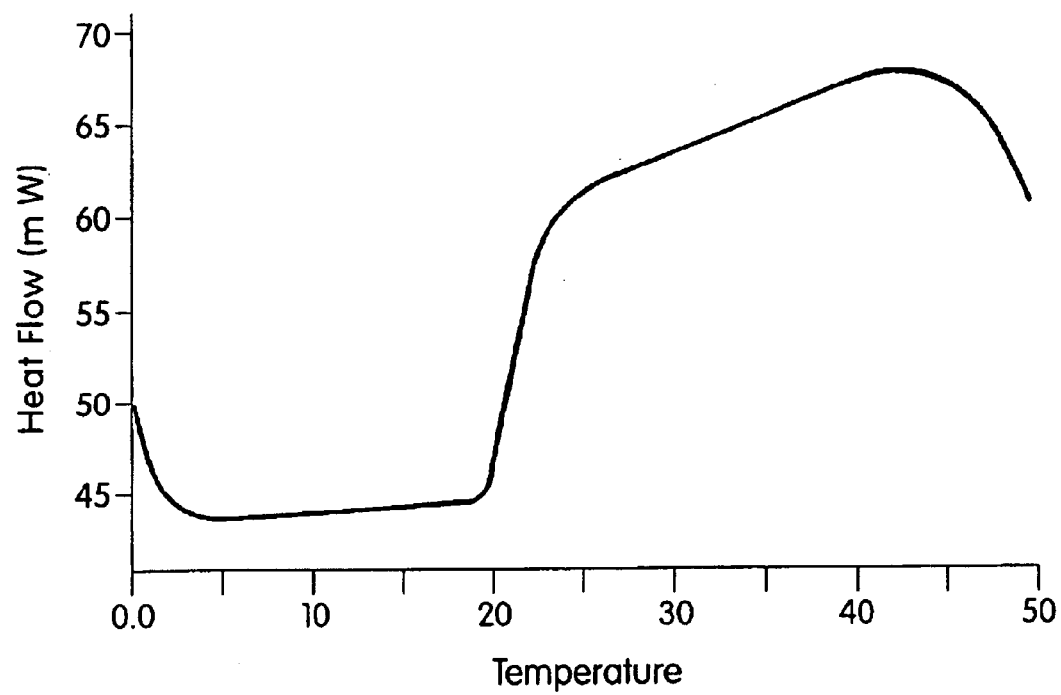
FIG. 16 is a differential scanning calorimetry PSC) plot of the reaction of reactive ACP with DCPD showing endothermic nature of the reaction.

The dry precursor mixture containing equal weights of ACP and DCPD was prepared as described in Example 9. Water (0.05 mL), prechilled to approximately 4° C., was added to 47.27 mg of the dry precursor mixture and immediately placed into the calorimeter. The DSC (Perkin Elmer 7 series thermal analysis system) was set to a starting temperature of C.° C with a scan rate of 5° C./min. The results are shown in FIG. 16. The plot represents a monitoring of the first 7 minutes of reactivity and shows essentially no heat flow between 0.0° C. and approximately 20° C., at which point onset of endothermic heat flow occurs. The heat flow properties indicate that at 37° C. the reaction is essentially endothermic, and under the conditions used, the reaction occurs only very slowly if at all at temperatures below about 20° C. Thus, the net reactivity in the system, that is, the sum of endothermic and exothermic heat flow of the system, is endothermic.

EXAMPLE 5

This example describes the step-by-step preparation and methods for the synthesis of a highly reactive amorphous calcium phosphate of the present invention.

The inert carbonited amorphous calcium phosphate was then prepared at room temperature by the rapid addition of solution B (43 g Ca(NO$_3$)$_2$.4H$_2$O (calcium nitrate tetrahydrate) and 1 g MgCl$_2$.6H$_2$O in 0.5 l of distilled water) to rapidly stirring solution A (55 g Na$_2$HPO$_4$.7H$_2$O (sodium phosphate), 50 g NaOH (sodium hydroxide), 30 g NaHCO$_3$, (sodium bicarbonate) and 2 g Na$_4$P$_2$O$_7$.10H$_2$O, in 1.3 l of distilled water). The precipitate of gel-like amorphous calcium phosphate thus formed was immediately filtered using filter paper (0.05 sq. m) with medium filter speed and a vacuum pressure of about 10$^{-2}$ torr. The material formed a thin cake and was washed with approximately 4 liters of distilled water by adding water into the filtration funnel. The washed material was then collected using spatula and immersed into a liquid nitrogen in a 2.5 L container. Following the formation of hard frozen pieces, the container was transferred into a vacuum chamber for 24 hrs (10$^-$$_1$–10$^{-2}$ torr), until a fine and dry powder was obtained.

Although the procedure described above may be performed at room temperature, the entire process preferably takes place below ambient temperature (4–5° C.), so as to further prevent the amorphous state from converting into more stable crystalline form.

An infrared spectrum of the inert amorphous material at this point in process is shown in FIG. 17a. This spectrum contains peaks characteristic of P—O groups (570 and 1040 cm$^{-1}$), CO$_3^{2-}$ group (1,420$^{-1}$, 450 cm$^{-1}$) with a relatively large O—H group peak (~3,550 cm$^{-1}$). The X-ray diffraction pattern of the same material demonstrates the amorphous nature of the material as indicated by absence of any sharp peaks in the 2θ=20 to 35 range.

The amorphous material described above was then activated to the highly reactive form by heating for 60 minutes at 450° C. (±3° C.). The IR of the heated material is shown in FIG. 17b. This spectrum shows a reduction of particular O—H and CO$_3^{2-}$-groups, indicating a significant reduction of H$_2$O and CO$_3^{2-}$ as CO$_2$ and H$_2$O. In similarly prepared samples the carbon content was observed to drop approximately 60% with a total carbonate ratio decreasing from 1.56% to 0.5%. Note, however, that the amorphous nature of the material was not lost during this process, as demonstrated by the x-ray diffraction pattern shown in FIG. 4a. The Ca/P ratio measurement of this material after the heat treatment was determined to be 1.575, using a method of quantitative electron microprobe analysis. The overall morphological and ultrastructural properties of the amorphous material was confirmed by transmission electron microscopy as shown in FIG. 1. Note the "amorphous" appearance of the material with absence of sharp edges separating each granules with certain portion of the material to exhibit shapeless form (arrows).

EXAMPLE 6

ACP was synthesized as described in Example 5 above, with the exception that solutions A and B were prepared in the following way: Solution A was prepared at room temperature by the rapid dissolution of 90.68 g of Ca(NO$_3$)$_2$.4H$_2$O in 1.2 liter of carbonated distilled H$_2$O. Solution B was prepared by dissolving 40.57 g of K$_2$HPO$_4$ in 1.53 liters of distilled H$_2$O, containing 24 ml of 45 vol. % KOH solution. Chemical and physical properties of the product amorphous calcium phosphate resulting from this procedure were similar to those of the material prepared accordingly for Example 5.

EXAMPLE 7

ACP was synthesized as described in Example 5 above, with the exception that solutions A and B were prepared in the following way: Solution A was prepared at room temperature by the rapid dissolution of 10.58 g of Ca(NO$_3$)$_2$.6H$_2$O in 0.15 liters of carbonated distilled H$_2$O at pH greater than 9.0, as adjusted by NaOH. Solution B was prepared by dissolving 7.8 g of (NH$_4$)$_2$HPO$_4$ in 0.35 liters of distilled H$_2$O.

EXAMPLE 8

This example describes the preparation of PCA calcium phosphate of the invention with manual mixing of the dry reactants.

Dicalcium phosphate dihydrate (DCPD) was prepared at room temperature by the rapid addition of solution B (17.1 g $Ca(NO_3)_2.4 H_2O$ (calcium nitrate tetrahydrate) in 250 mL distilled water) to solution A (10 g $H_9N_2O_4P$ (diammonium hydrogen phosphate) in 500 mL distilled water at a pH of 4.6–4.8) with constant stirring. Immediately thereafter, the sample was filtered using filter paper (0.05 sq. m) with medium filter speed and a vacuum pressure of about 10-2 torr. The material formed a thin cake which was washed with about 2 liters of distilled water and then dried at rock temperature for 24–72 hrs.

Figure 3:
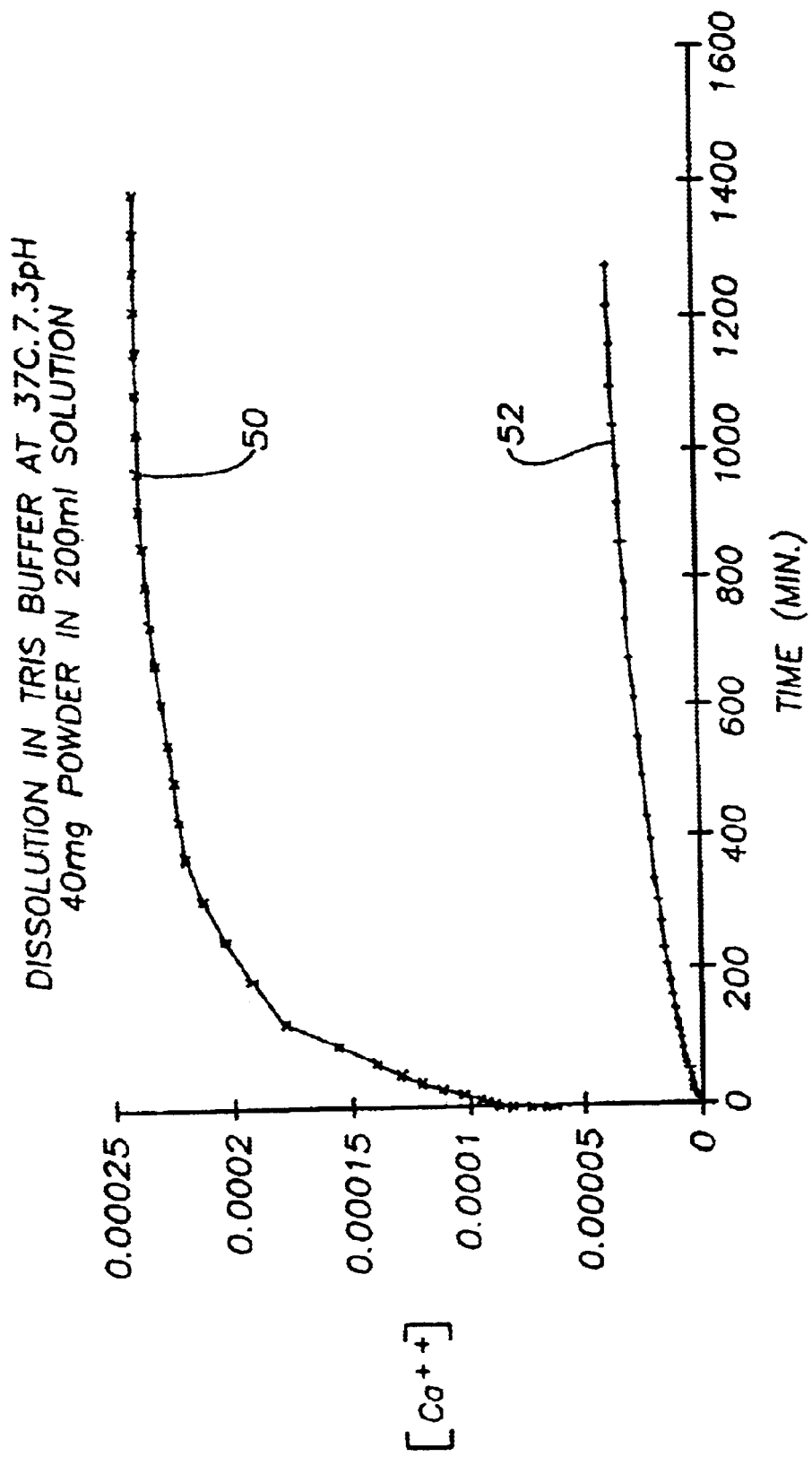
FIG. 3 is a solubility curve of a poorly crystalline apatitic calcium phosphate product derived from amorphous calcium phosphate of the present invention, as compared with a crystalline hydroxyapatite. Note the relative higher solubility of the material of the present invention versus a more crystalline form of hydroxyapatite, as measured by the amount of calcium ions released into solution at 37° C.

The reactive amorphous calcium phosplate material prepared from Example 5 was physically dry-mixed with dicalcium phosphate dihydrate ($CaHPO_4.2 H_2O$) at 50:50 wt. % using a mortar and pestle for 3–5 min. Water (1 mL/g of mixed material) was then added to the powder mixture to yield a paste-like consistency. The amount of $H_2O$ added varied, depending on whether a thick or thin paste was desired. The hydrated precursor material was then wrapped loosely in moist tissue paper and heated to 37° C. At this temperature the paste hardened into a solid mass by means of a substantially endothermic reaction. The hardening process could be delayed for several hours by refrigerating the sample at 4° C. The hardened material was composed of PCA calcium phosphate with an inherent solubility property that exceeded reported solubilities for a synthetic hydroxyapatite material. This is demonstrated in FIG. 3, where the concentration of calcium ions released into a controlled pH buffer solution over 24 hrs at 37° C., was significantly higher for the PCA calcium phosphate material of the present invention (curve 50) than the standard crystalline hydroxyapatite material (curve 52).

EXAMPLE 9

This example describes the preparation of the inventive PCA calcium phosphate using automated mixing of the dry precursors.

The dry ACP and DCPD precursors were prepared as described in Example 8. Instead of mixing with a mortar and pestle, the ACP and DCPD were mixed using a SPEX 8510 laboratory mill with a SPEX 8505 alumina ceramic grinding chamber for 2 min. Preparation of the hydrated precursor was accomplished by adding from 0.7 to 1.5 mL of water per gram of mixed dry precursors.

EXAMPLE 10

This example demonstrates the preparation of PCA calcium phosphate using DCPDs of specific grain size distributions.

DCPD was prepared as described in Example 8. The dry material was ground for 5 minutes in a SPEX 8510 laboratory mill with a SPEX 8505 alumina ceramic grinding chamber. Following grinding, the material was serially sieved through a Tyler test sieve shaker to produce DCPD with 8 different grain size distributions as indicated in Table 3 and shown in FIG. 8.

TABLE 3

DCPD Grain Size Distribution

| Sample | Grain Size Distribution | Extent of hardening at 30 min, 37° C. |
|---|---|---|
| 10-1 | <25 μm | hard |
| 10-2 | 25–35 μm | hard |
| 10-3 | 35–53 μm | hard |
| 10-4 | 53–63 μm | hard |

TABLE 3-continued

DCPD Grain Size Distribution

| Sample | Grain Size Distribution | Extent of hardening at 30 min, 37° C. |
|---|---|---|
| 10-5 | distribution B3 (FIG. 8) | hard |
| 10-6 | 106–125 μm | not fully hardened |
| 10-7 | distribution B2 (FIG. 8) | not fully hardened |
| 10-8 | unsieved distribution B1 (FIG. 8) | not fully hardened |

It has been found that the preliminary grinding of DCPD prior to sieving can be replaced by a brief hand grinding using a mortar and pestle without substantially changing the results.

The reactive amorphous calcium phosphate material prepared from Example 5 was physically dry-mixed 1:1 (wt/wt) with each of the DCPD samples from Table 3 for 10 minutes using a SPEX 8510 laboratory mill with a SPEX 8505 alumina ceramic grinding chamber. Water (0.8–1.0 mL/g of dry mix) was then added to each powder mixture to yield a hydrated PCA calcium phosphate precursor with a paste-like consistency. Six of the eight samples indicated in Table 3 hardened well in 30 minutes at 37° C. Samples 10-6, 10-7 and 10-8 did not harden as quickly or as firmly as the other samples. Each of these samples had significantly higher percentages of >100 μm particles than the other samples. It is concluded from these observations that the use of smaller grain size DCPD leads to more rapid and complete hardening than larger grain size DCPD.

EXAMPLE 11

This example describes two preferred embodiments of the instant invention.

Figure 8:
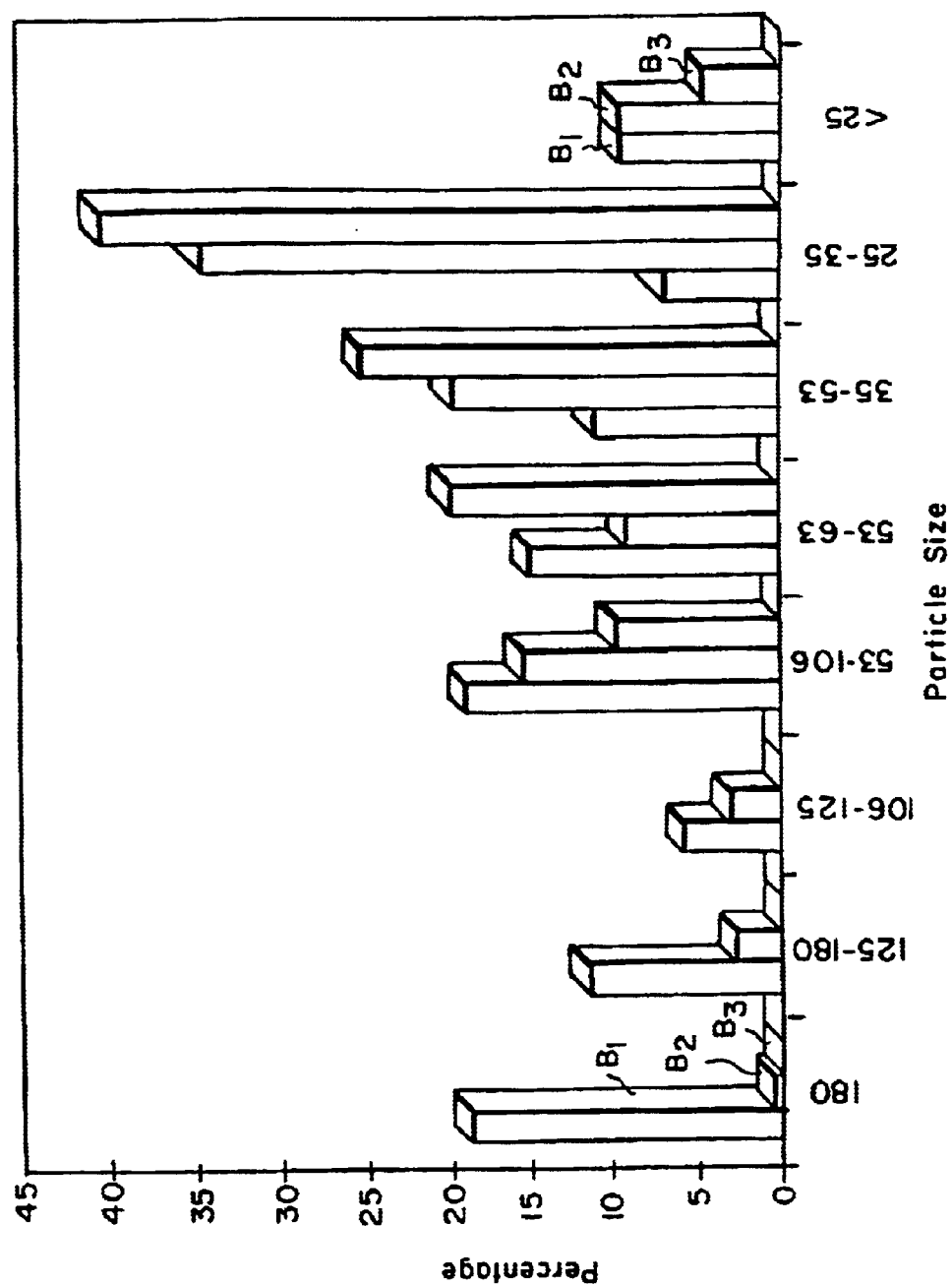
FIG. 8 is a bar graph displaying particle size distribution for various formulations described in Example 10.

(a) Reactive amorphous calcium phosphate material prepared according to Example 5 was physically dry-mixed with DCPD with a particle size distribution of B3 of FIG. 8 at 50:50 wt. % using a SPEX 8510 laboratory mill for 2 min with a SPEX 8505 alumina ceramic grinding chamber, followed by sieving to a size of less than 150 μm (Type 2 powder). Adater (0.8 mL/g of mixed material was then added to the powder mixture to from the hydrated precursor.

(b) This preferred embodiment was prepared as in (a) with the exception that samples were dry mixed and subsequently ground for 10 minutes (Type 10 powder).

Different resorption behaviors have been observed for Type 2 and Type 10 powders in soft tissues (see, Example 16); however, resorption of both powder types in hard tissue (bone) is similar. This may be due to different absorption mechanisms in soft and hard tissues. Soft tissue assays are more sensitive, therefore, and may prove valuable when assessing resorbability of new PCA materials (See, Example 16).

EXAMPLE 12

This example describes alternative methods for preparing hydrated PCA calcium phosphate precursor.

(a) Reactive ACP and DCPD were prepared as described in Example 9 with the exception that the dry precursors were not mixed. Water (0.8 mL) was added to ACP (0.5 g) and mixed thoroughly to homogeneity with a spatula to form a paste. DCPD (0.5 g) was then added to the paste and the paste was mixed for approximately 2 min. The resultant paste was placed into a moist environment at 37° C. for 30 min.

(b) Reactive ACP and DCPD were prepared as described in Example 8. Water (0.8 mL) was added to DCPD (0.5 g) and mixed thoroughly to homogeneity with a spatula to form a paste. ACP (0.5 g) was then added to the paste and the paste was mixed for an additional 2 min. The resultant paste was placed into a moist environment at 37° C. for 30 min.

In both instances, the paste hardened after 30 minutes, indicating a successful reaction.

EXAMPLE 13

This example describes hardness testing of a PCA calcium phosphate calcium phosphate.

PCA calcium phosphate calcium phosphate was prepared according to Example 9 to form a paste. The paste was placed into a 6 (dia.)×10 (depth) mm hollow Teflon® tube submersed in 37° C. water for 30 minutes. The hardened PCA calcium phosphate was then removed from the tube and placed in water at 37° C. for 1 hour and then, while still moist, placed vertically on an Instron 4206 having a dual 10 kg/15 ton load cell. Compressibility was determined using a crush test. Approximately, 200–250 N were required to bring the sample to failure. This force corresponds to a compressive strength of 7–9 Mpa.

Poly(lactide) whiskers are prepared with average dimensions of about 5–100 μm diameter by 10–250 μm length. The whiskers are mixes with poorly crystalline hydroxyapatite paste prepared as described above at a concentration 10% wt/wt. The composite paste is hardened overnight at 37° C. in moist environment. When tested for compressibility, the material is found to have improved compressibility over the non-composite PCA calcium phosphate.

EXAMPLE 14

These examples demonstrate the effect of fluid volume on the consistency and reactivity of injectable paste to be used in the formation of bone substitute material. Each of the pastes were prepared as described in Example 8, above, and the consistency and rate of reaction at room temperature and 37° C. were determined. Observations are reported in Table 4.

TABLE 4

Formability, Injectability and Reactivity of Hydrate Precursor.

| Example No. | water volume (mL) | formability | injectability | hardening time at various temps. (4° C./RT/37° C.) |
|---|---|---|---|---|
| 14-1 | 0.7 | – crumbles | – | –/–/– |
| 14-2 | 0.8* | +++ easily formed paste | + | >60 min/>60 min/ 30 min |
| 14-3 | 0.9* | ++ toothpaste | ++ | >60 min/>60 min/ 30 min |
| 14-4 | 1.0 | + liquid toothpaste | +++ | >60 min/>60 min/ 30 min |

*Under some circumstances (e.g., evaporation) these samples may dry out somewhat over a period of one hour at room temperature. In such cases, additional water may be added to restore the original consistency.

EXAMPLE 15

Implantation and Resorption of PCA calcium phosphate in a Subcutaneous Site. This example demonstrates the resorption of the inventive PCA calcium phosphate when implanted subcutaneously into rats. It also demonstrates a useful screening procedure to test resorption characteristics of new formulations of bioceramic implant materials and composites.

Eighty male and eighty female Sprague-Dawley rats were each implanted with 4 ml (2–4 gm) of the inventive PCA (prepared according to Example 8) into the dorsal subcutis (>10× the amount considered maximal in humans on a per kg basis). Control animals were treated with an equal volume of saline. Operation procedures are described in Example 16. The rats were sacrificed according to the schedule presented below in Table 5; the implant site was examined as described in Example 16.

TABLE 5

Sacrifice Schedule

| Sacrifice Timepoint | PCA calcium phosphate implant |
|---|---|
| 1 week | 5 m/5 f |
| 2 weeks | 5 m/5 f |
| 1 month | 5 m/5 f |
| 3 months | 5 m/5 f |
| 1 year | 20 m/20 f |

Blood for clinical pathology analyses was collected via retroorbital sinus or cardiac puncture (all by the same method) while the animals were under $CO_2$ anesthesia. Blood samples were collected from each group of animals prior to scheduled sacrifice. Clinical observations of the animals for general health and well-being were performed at least weekly until 3 months, and then monthly.

At 1 week PCA material was present at the implant site and was found associated with moderate to marked granulomas presumable associated with the resorption process. At week two a small amount of PCA material was still present at the implant site and associated granulomas were mild to moderate. By week four most tissue appeared normal with a few mild granulomas persisting at the implant site. At week twelve no evidence of the implant remained.

EXAMPLE 16

Implantation and Resorption of PCA calcium phosphate in an Intramuscular Site. This example describes the preparation of PCA calcium phosphates that have varied in vivo resorption times as a result of varied grinding times.

Individual dry precursors, ACP and DCPD were prepared as described in Example 8. Several different formulations of DCPD and ACP were then prepared by i) grinding DCPD for 15 sec, 30 sec, 1 min, 2.5 min, or 5 min in a SPEX grinder; ii) combining the ground DCPD 1:1 with ACP; and iii) grinding the mixture for an additional 15 sec, 30 sec, 1 min, 2.5 min, or 5 min, respectively. Total grinding times for the different preparations were therefore 30 sec, 1 min, 2 min ("Type 2" powders), 5 min, and 10 min ("Type 10" powders).

The PCA calcium phosphate, sterilized in powder form by approximately 2.5 Mrad of gamma irradiation, was prepared by taking the material in powder form and mixing with sterile water or saline and forming it into approximately 1 cm disks 2 mm thick and incubated for a minimum of 30 minutes at 37° C. Disks were implanted into adult male New Zealand White Rabbits immediately following fabrication.

Animals were assigned to dose groups which contained 3 males for a total of 15 animals. The implants were assigned to the rabbits randomly. 10–15 minutes prior to the surgery, the animal was premedicated with xylazine (10 mg/kg, i.m.). The animal was then given ketamine (50 mg/kg, i.m.). The dorsal surface of the animal was clipped free of hair and washed with a betadine surgical solution and alcohol. Before the surgery the animal was monitored to be sure that is was properly anesthetized. To do this, pressure was applied to the foot pad. When there was no response, the animal was properly anesthetized. Throughout the procedure, the animal was monitored for whisker twitching and the toe-pinch reflect, which indicated that the animal was not waking up.

Using aseptic technique and a scalpel blade, an incision 1–2 cm in length was made in the skin over the m. longissimus lumborum (which lies along both sides of the spine). When the incision was made, the underlying fascia and muscle was also cut to allow the sample to pas into the muscle. The sample disk was placed directly into the muscle, being sure that the entire implant was embedded in the muscle. The muscle was closed with a single absorbable suture and the skin was stitched closed subcutaneously. Metal skin staples were used to close the external skin surface incision. Five samples were placed on each side in this manner. Each sample was placed at the end of the incision and they were approximately 1 cm apart from each other (see diagram). The samples were in the form of 7 mm by 2 mm disks weighing approximately 150 mg. The animals were monitored and were given buprenorphine (0.02–0.05 mg/kg, s.q) upon awakening. The analgesic was administered 2 times per day for three days after surgery.

The animals were radiographed immediately after the surgery and for every two weeks thereafter. The radiographs were compared to track the resorption of the materials. A standardized method was used for the radiographs to minimize any variation between timepoints.

After euthanasia, implant sites were first evaluated by gross examination. In those sites with visible implants, the implants appeared as grey to yellow solid discs. In those sites where the implant had been resorbed, areas of red to tan discoloration of the muscle were observed.

Muscle tissue, with the implants, was removed, being careful not to disturb the implants. The tissues and the identifying marks were placed into labeled jars filled with 10% neutral buffered formalin. All implant sites were processed and evaluated microscopically. Observations included focal fibrosis, focal granulomatous inflammation, and appearance of the implant (in some cases). Fibrosis was primarily seen as fibrocytes and collagen. Animals with gross resorption had fibrosis and minimal to moderate granulomatous focal inflammation. Granulomatous inflammation was seen as focal aggregates of macrophages and giant cells, often with intracytoplasmic crystals, and occasional heterophils and lymphocytes. Inflammation around the non-resorbed implants was primarily minimal to mild fibrosis and/or granulomatous inflammation, both of which are within the acceptable range for intramuscular implants.

At four weeks, the pellets made from PCA calcium phosphate implants that had been prepared by grinding for 30 seconds, 1 minute, or 2 minutes were fully resorbed. Those that had been prepared by grinding for 5 minutes or 10 minutes were not fully resorbed.

EXAMPLE 17

Reactive amorphous calcium phosphate material is prepared as Example 5 and is dry-mixed with other calcium phosphate compounds, according to the method described in Example 8 with the following modification. Instead of DCPD, the following calcium phosphate compounds are used, including, but not limited to: $Ca(PO_3)_2$ (calcium metaphosphates), $Ca_7(P_5O_{16})_2$ (heptacalcium phosphate), $Ca_2P_2O_7$ (calcium pyrophosphate), $Ca_3(PO_4)_2$ (tricalcium phosphates). The dry-mixture ratio is properly calculated to be between Ca/P ratios of 1.5–1.70, depending on the molar Ca/P ratio of the compound mixed with the reactive amorphous calcium. The PCA calcium phosphate identity of the resulting material is then confirmed through the use of XRD and FTIR.

EXAMPLE 18

This example follows the conversion reaction occurring in association with the hardening of the hydrated precursor using X-ray diffraction and Fourier transform infrared spectrometry.

Figure 6A:
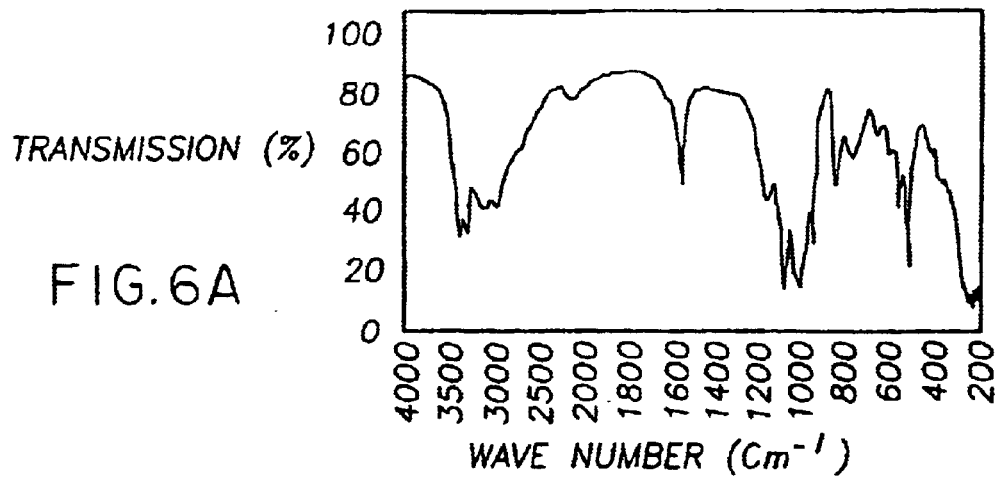
FIG. 6 is infrared spectra of (a) dicalcium phosphate dihydrate, (b) the activated ACP of the invention, and (c) the PCA material of the present invention.
Figure 6B:
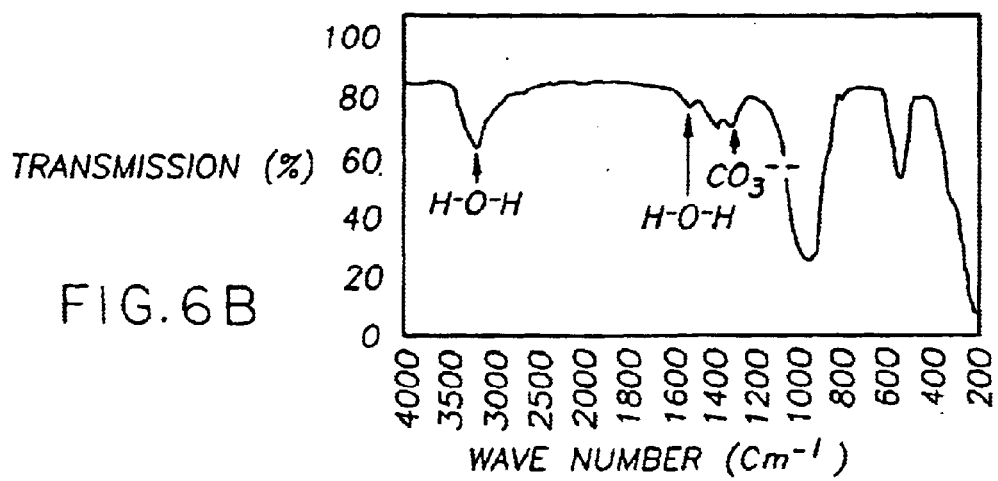
Figure 6C:
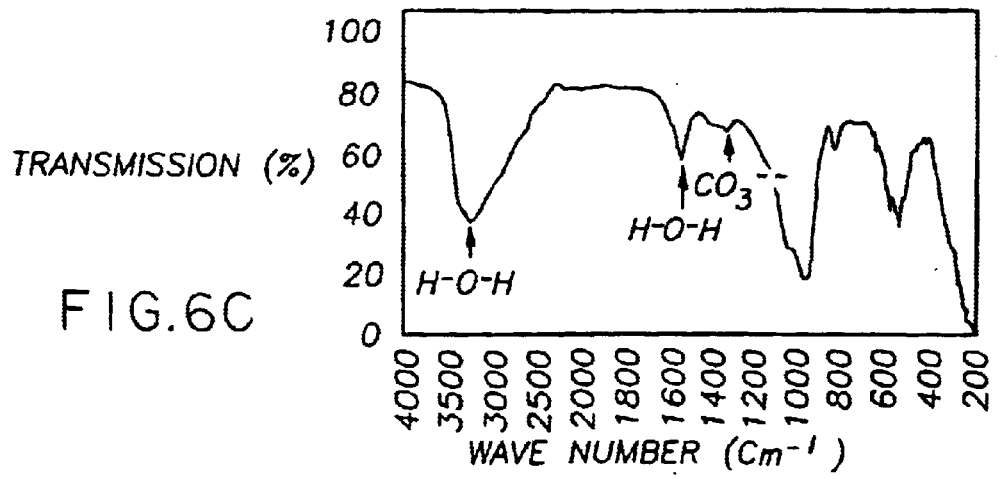

Hydrated precursor was prepared as described in Example 9. The reaction mixture was placed in a moist environment at 37° C. and examined by X-ray diffraction spectrometry at different times. FIGS. 5a–d are the X-ray diffraction spectra of the reaction product between DCPD and the reactive amorphous calcium phosphate as described in Example 5. X-ray scan conditions are (a) copper anode, (b) λ=1.4540598, and (c) a scan range 20–35° at a step of 0.02° and step interval of 2 seconds. FIG. 6 shows the infrared spectra of dicalcium phosphate dihydrate (FIG. 6a), the activated ACP of the invention (FIG. 6b), and the poorly crystalline hydroxyapatite of the present invention (FIG. 6c).

Figure 4B:
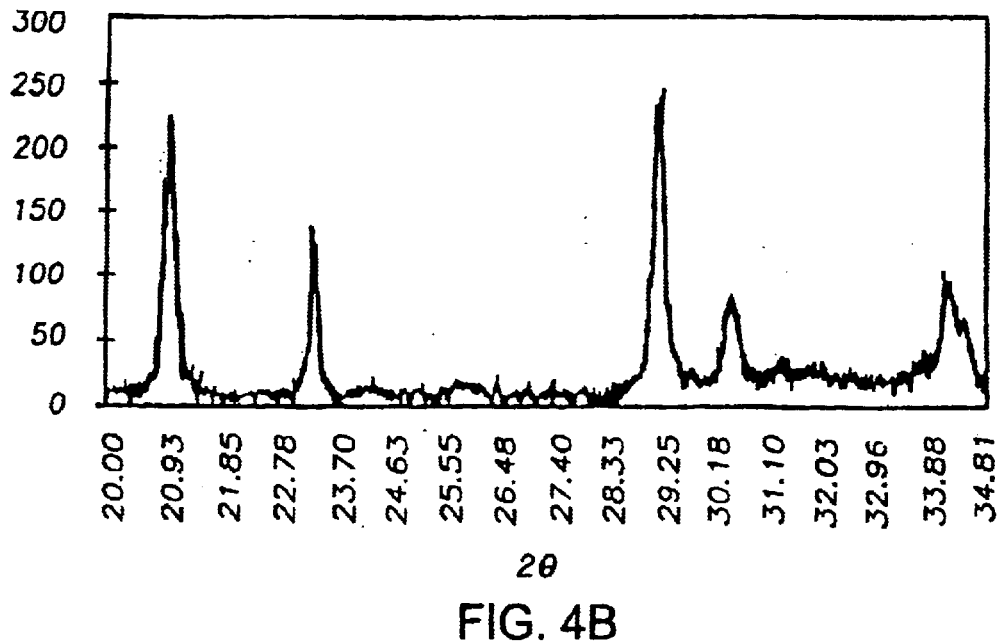
Figure 7:
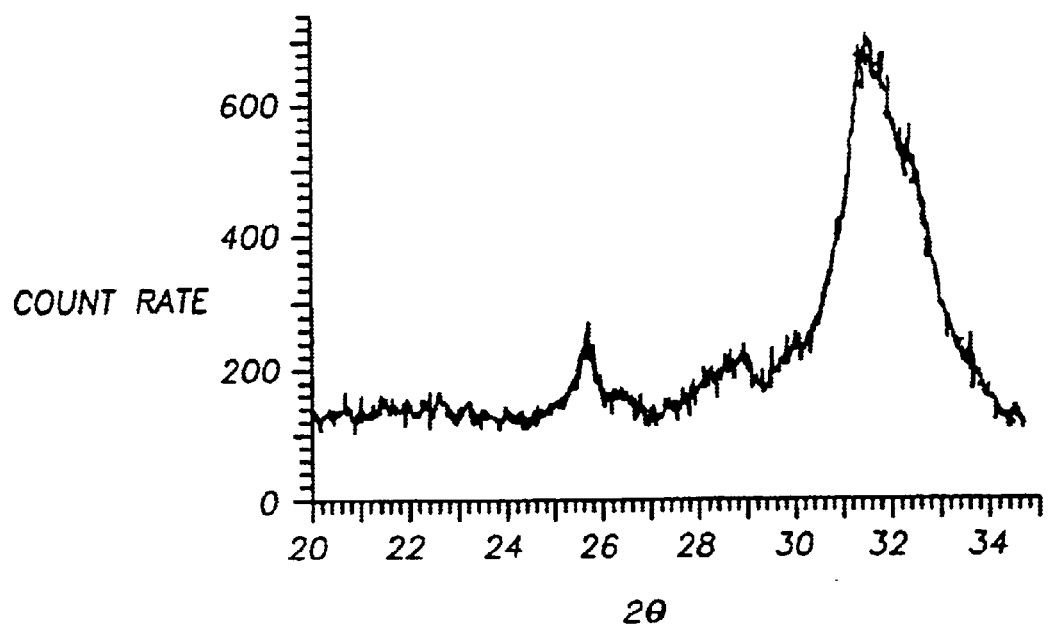
FIG. 7 is an X-ray diffraction pattern of naturally occurring bone.

Samples shown in FIGS. 5a–5d were incubated for 0, 20 min, 75 min and 5 hours, respectively. The samples were removed at the noted time and lyophilized to preserve chemical characteristics. FIG. 5a, taken at the start of the reaction, represents a combination of peaks attributable to the starting ACP and dicalcium diphosphate (see, FIG. 4 for component XRD patterns). The sharp peaks at ca. 20.25°, 23.5°, 29.5°, 30.75° and 34.2° for crystalline dicalcium diphosphate are readily observed. With increasing reaction time, the sharp crystalline peaks subside and wide (amorphous) peaks appear centered at 2θ=26°, 28.5°, 32.0° and 33.0°. It is interesting to note that there is no change in the spectra after 75 minutes of reaction, indicating that the reaction essentially complete in little more than one hour. The X-ray diffraction pattern of the bone substitute material of the invention (FIG. 5d) can be compared to that of naturally occurring bone, shown in FIG. 7. The two spectra are nearly identical.

EXAMPLE 19

Implantation and Resorption of PCA calcium phosphate in a Bony Site

The purpose of this study was to assay resorption and ossification of PCA calcium phosphate in a bony implant site. The method is also useful for testing the resorption and ossification properties of PCA calcium phosphate formulations and composites of the invention.

The test article used was a PCA calcium phosphate formulation prepared as described in Example 8. The ACP and DCPD were mixed in the specified proportions and ground for 1 minute, 30 seconds in the SPEX grinder equipment.

Adult (>5 month old) NZW male rabbits were held in quarantine and acclimatized for a minimum of 10 days prior to the initiation of the study. Animals were individually housed in suspended stainless steel cages. Wood shavings were used in dropping pans under the cages. Prior to initiation of the study, animals were assigned to groups or treatments randomly and were identified by a numbered ear tattoo and by a corresponding cage card. All animals had single defects placed in one tibia. Timepoints for evaluations were 2, 4, and 8 weeks (2 animals at each timepoint). Surgery was performed under full anesthesia and aseptic surgical conditions.

After obtaining adequate anesthesia (e.g., ketamine/xylazine to effect), using aseptic technique, an incision was made over the lateral proximal tibia. The soft tissue was deflected away and the bone exposed. Using an approximately 5 mm trephine in a low speed dental handpiece with irrigation (0.9% physiologic saline) as needed, a ~5.5 mm diameter hole was cut through the cortical portion of the bone. The bony disk was dissected free from the cortex and the site was prepared for implantation. The hydrated precursor material in paste form was placed into the defect. Defects in control animals were left untreated. The soft tissues were then closed in layers. One sample per animal was prepared using this method.

Clinical observations of the animals' general health and well-being, with special regard to their ambulator, abilities, were made at least weekly. All animals appeared to be in good health. At the end of the study the animals were euthanized with an overdose of anesthetic and the implant site collected. Radiographs of the tibiae were made at scheduled intervals including after surgery and at the time of necropsy.

The implantation sites were fixed in formalin and stained with either hematoxylin and eosin, Masson's trichrome, or Von Kossa stained slides from decalcified samples. Undecalcified histological samples were also prepared and stained with light green basic fuschin. Slides were microscopically evaluated by a board certified veterinary pathologist (ACVP) with experience in laboratory animal pathology. Subjective observations were made of bone morphology, and presence or absence of organized bone and of detectable PCA calcium phosphate material was noted.

Figure 9A:
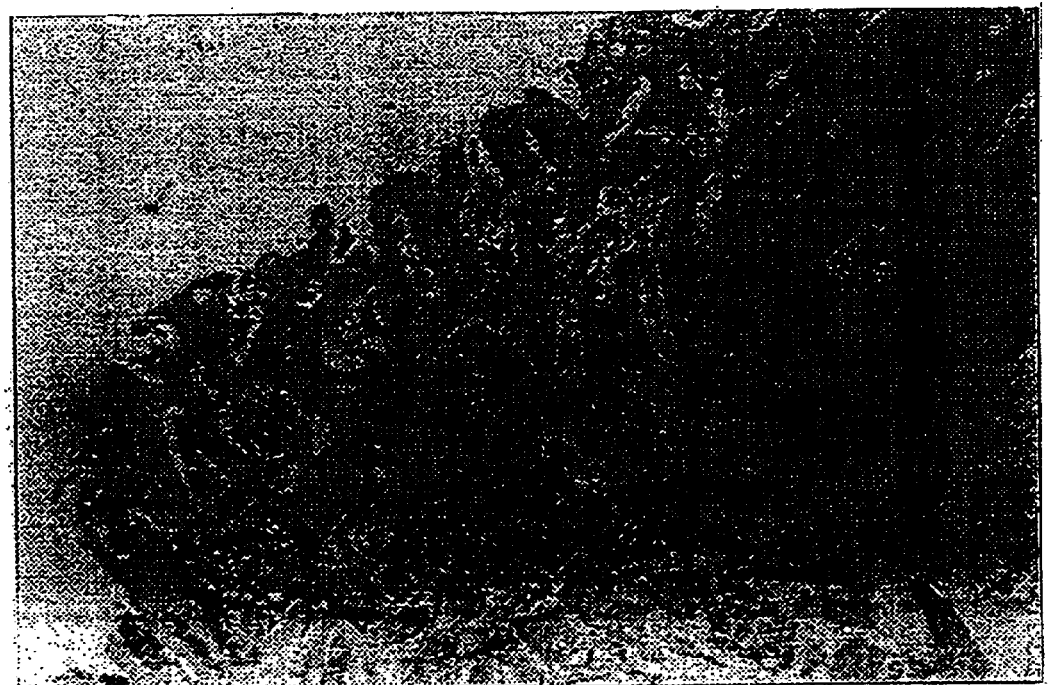
in FIG. 9a, the small arrows indicate one edge of the defect; the large arrowhead is at the yet unbridged defect.
Figure 9B:
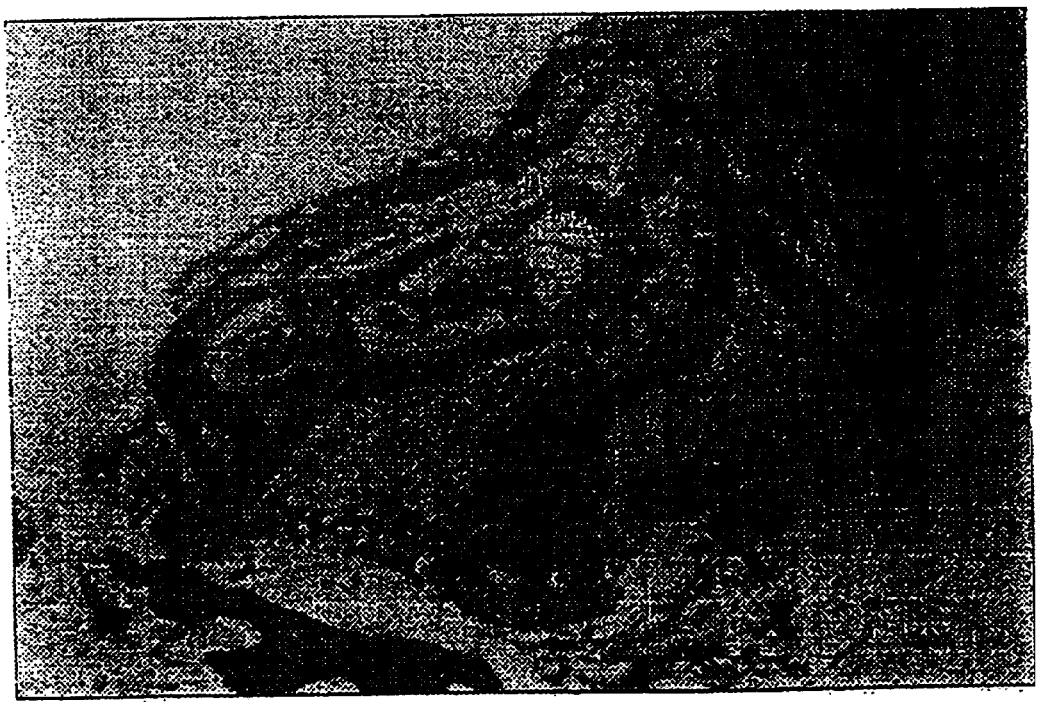
in FIG. 9b, large arrowheads denote one edge of the defect; and in both Figures, magnification is 4×, bone is decalcified, and slides are treated with hematoxylin and eosin.
Figure 10:
FIG. 10 is a photomicrograph of canine trabecular bone grown into a defect treated with the PCA material of the present invention (magnification 10×; decalcified; hematoxylin and eosin)
Figure 11:
FIG. 11 is a photomicrograph of a canine cortical bone defect that was treated with the PCA material of the present invention (magnification 4×; undecalcified, Light Green Basic Fuchsin)
Figure 12A:
FIG. 12 presents photomicrographs of untreated (FIG. 12a) and treated (FIG. 12b) rabbit tibia defects 4 weeks after surgery (magnification 4×; decalcified; Masson's Trichrome)
Figure 12B:
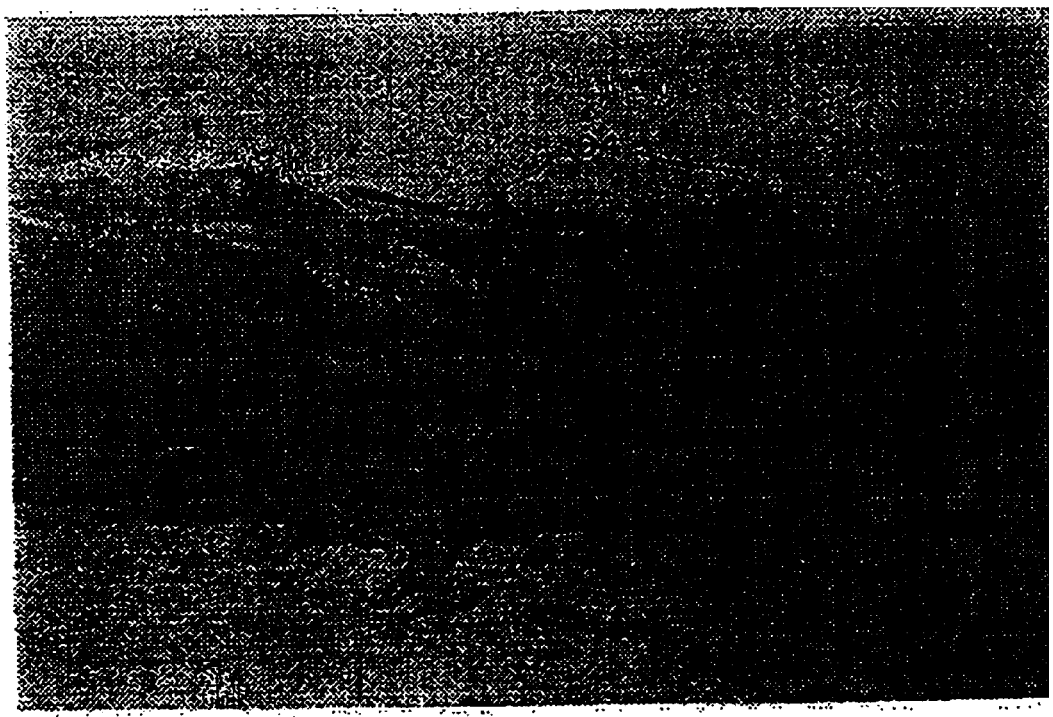

Histological results indicated some mineralization at 2 weeks. By 4–6 weeks, animals receiving implants had normal trabecular bone at the implant site with no evidence of remaining PCA calcium phosphate. The untreated controls had not fully healed in that they had less than full ingrowth and/or had non-cortical-type bone. FIGS. 9a and 9b are photomicrographs of untreated and treated tibia defects, respectively, 2 weeks after surgery. As can be seen, bone to the right of the defect edge in the untreated sample (FIG. 9a) is thin trabecular bone; new bone to the right of the defect edge in the treated sample (FIG. 9b) is thick trabecular bone.

EXAMPLE 20

This example demonstrates the difference in resorption time between two precursor formulations with different DCPD grain size distributions. PCA calcium phosphate precursor material is prepared according to example 10. Two precursor mixes are prepared. Sample A corresponds to sample 10-6 and sample B corresponds to a 2:4:3:1 mix of samples 10-1, 10-2, 10-3 and 10-4. Hydrated precursor pastes of the two samples are tested in rodents in the subcutaneous test of example 15. Resorption is monitored at various time points.

EXAMPLE 21

This example demonstrates the difference in promoting activity of DCPD of two different grain size distributions in the conversion of both highly reactive and reactive ACPs ACP was prepared as in Example 5, with the exception that for some of the samples the final heat activation step was omitted. Two samples of DCPD with grain size distributions corresponding to B1 & B3 of example 10 were prepared. The ACPs and DCPDs are then mixed for 5 minutes, either by hand or in the SPEX grinder. Hardening characteristics are then determined. It is clear that machine milled samples exhibited superior hardening properties over hand ground samples. It is also clear that the samples with a smaller particle size (B3) exhibited superior hardening properties over larger grained samples (B1).

TABLE 6

Reactions Using Different Strength Promoters

| ACP | DCPD | grinding | hardening @ 30 min |
|---|---|---|---|
| heated | B3 | mortar | ++ |
| non-heated | B3 | & | (not done) |
| heated | B1 | pestle | +/− |
| non-heated | B1 |  | − |
| heated | B3 | SPEX | +++ |
| non-heated | B3 | 5–10 min | +++ |
| heated | B1 |  | + |
| non-heated | B1 |  | (not done) |

EXAMPLE 22

This example determines the specific surface area and porosity of a PCA calcium phosphate material.

ACP was prepared according to Example 5. Samples from before and after the final heat activation step were compared for their reactivity in an in vitro hardening assay with unsieved DCPD (as described in example 8). Specific surface area and average porosity were also measured. Results are tabularized in Table 7 below.

TABLE 7

Specific surface Area and Porosity of the Inventive ACPs

| sample | specific surface area (sq. m./g) | Average Porosity (Å) | DCPD Reactivity |
|---|---|---|---|
| Pre heating | 120.5 | 130 | − |
| After heating | 76.8 | 129 | + |

EXAMPLE 23

This example describes the conversion of ACP to PCA calcium phosphate in the absence of a promoter and demonstrates the failure of the newly formed PCA calcium phosphate to harden. Likewise, promoter DCPD fails to harden or convert on its own.

DCPD and a variety of ACPs and other calcium phosphates were mixed with water and tested for their ability to harden at 37° C. Table 8 summarizes these results, as well as identification of the reaction products, if any, following the test period. Under no circumstances was hardening observed up to 3 days. It was concluded that while conversion of ACP to PCA calcium phosphate may occur, the presence of a promoter is desired to achieve setting and hardening

TABLE 8

ACP conversion in the absence of a promoter

| ACP | $H_2O$ (g) | Incubation | Hardening | FTIR | XRD |
|---|---|---|---|---|---|
| ACP (Example 5) | 0.8 | 30 min | soft | ACP | ACP |
|  |  | 12 hrs | soft | PCA* | PCA* |
| DCPD (Example 8) 38–53 μm | 0.7 | 30 min | soft | DCPD | ND |
|  |  | 12 hrs | soft | DCPD |  |
| ACP (Example 7) not heat activated | 1.5 | 30 min | soft | PCA* | ND |
|  |  | 12 hrs | soft | HA |  |
| ACP (Example 5) non-carbonated | 1.5 | 30 min | soft | ACP | ND |
| ACP (Example 6) not heat activated | 1.5 | 30 min | soft | ACP | ND |
| ACP (Example 5) non-carbonated; heat activated | 1.5 | 30 min | soft | PCA* | ND |

*PCA = poorly crystalline apatitic calcium phosphate
ND = analysis not done

EXAMPLE 24

Different Hydrating Agents Effects on Hardening and Final Product.

A hydrated precursor (ACP and DCPD) was prepared as described in Examples 8, 9, or 10, with the exception that a variety of hydration media were used. Samples were then tested for hardness and completeness of reaction at various time points. In all cases, 1 g of the mixed precursors were hydrated with 0.75–1.0 mL of hydration medium to produce a paste. Table 9 summarizes the results and demonstrates that a variety of aqueous based liquids, and in particularly physiologically acceptable media, may be used in the preparation of PCA calcium phosphate.

TABLE 9

Effect of Hydrating Agents

| Hydration Medium | Incubation Time | Hardening |
|---|---|---|
| Tris | 30 min | hard |
| 0.9 M NaCl | 30 min | hard |
| MEM | 30 min | hard |
| MOPS | 30 min | hard |
| HEPES | 30 min | hard |
| BUFFERALL | 30 min | hard |
| PBS | 30 min | hard |

EXAMPLE 25

ACP was prepared as described in Example 5, with the exception that the heating the ACP to 450° C. was carried out for either 1 hour or 6 hours. Following heating the ACP was prepared for reaction with DCPD as described in Example 8. Hydrated PCA calcium phosphate precursor prepared with ACP heated for 6 hours was found not to harden after 2 hrs at 37° C.

EXAMPLE 26

The porosity of a hardened sample of PCA calcium phosphate prepared according to Example 10-5 was determined.

A hardened sample of PCA calcium phosphate (1 g) was weighed immediately after removal from the moist incubator, and then air dried at room temperature for 12 hrs. The dried sample was carefully weighed and then the volume was calculated. The sample was placed into a 20 mL sample of water. After 1 minute the approximate displacement volume was noted. The dried sample was found to absorb up to 50–60% of its dry weight in $H_2O$. These results are interpreted to mean that the sample is up to 50–60% porous. Density was approximated at 1.65 $g/cm^3$.

EXAMPLE 27

This example demonstrates the use of a resorbable polymer to promote the conversion of ACP to PCA calcium phosphate.

Granular PLLA is prepared and sieved to a size of 100 μm. The powder thus obtained is mixed with the ACP (5:1 ACP:PLLA) of Example 9 and ground for 5 minutes in a SPEX laboratory mill. Water is added to 1 g of the mixture to form a workable paste. The paste is shaped into a ball and is heated to 37° C. in a moist environment for 1 hour. The hardened sample is analyzed using FTIR and XRD.

EXAMPLE 28

This example investigates the hardening characteristics of the hydrated precursor at sub-ambient temperatures.

Hydrated precursor was prepared with water as described in Example 9 and then tightly sealed to avoid evaporative loss either in parafilm or in an aluminum tube. The samples were then held for up to 1 hr, 24 hrs and 6 days. At the indicated time points, the hydrated sample was removed from refrigeration placed in a moist environment at 37° C. In all instances the samples hardened within 30 minutes.

EXAMPLE 29

This example demonstrates the efficacy of the inventive PCA calcium phosphate in promoting the healing in a large animal model, of a full segmental defect in a weight bearing limb.

Hydrated precursors Type 2 and Type 10 were prepared and treated immediately prior to surgery as described in Example 16.

Animals fasted for 24 hours prior to anesthesia, during this time interval water was available ad libitum. Ketamin (Aescoket®, 10 mg/kg i.m.) and atropine (1.5 mg i.m.) was administered as a pre-medication about 15 minutes before fully anesthetizing the animals. Etomidate (Hypnomidaat®, 0.3 mg/kg i.v.) was used as the anesthetic. After intubation, anesthesia was maintained with an $O_2/N_2O$-mixture (1:1, vol/vol) supplemented with 2% isoflurane.

Surgery was performed aseptically under full anesthesia. After shaving and iodinating the skin, an incision was made over the anteromedial side of the tibia. The muscles were bluntly dissected and the tibial shaft was prepared free of tissue to as great an extent as possible. After reaming the medullary cavity, an intramedullary nail (diameter 8 mm) was inserted via a hole in the anterior tibial plateau. The inserted nail was locked with two proximal and two distal bolts. A 20 mm osteoperiostal segmental defect was then created in the mid-shaft of the tibia with the aid of a thread saw and an oscillating saw.

The defect was filled according to the treatment group. In one group, autologous bone was harvested from the ipsilateral iliac crest and placed into the defect. In the other group, approximately 2–4 g of the hydrated PCA calcium phosphate precursor (type 2 or type 10) was applied by hand so fill the defect. The soft tissues and the skin were closed in layers with resorbable suture material.

The animals received post operative lincomycin/ spectinomycin (Vualin Plus®, 5 mg/10 mg per kg per day) for 3 days by intramuscular injection. The animals were kept outside in the meadow as soon as full weight bearing of the operated limb was possible. Animals were sacrificed prior to explanation of the tibiae as follows: As a premedication ketamin (Aescoket®, 500 mg i.m.) and xylazin (Rompun®, 40 mg i.m.) were given. Then 0.5 mg fentanylcitrate (Fentanyl®), 10 mg etomidate (Hypnomidate®), 4 mg pancuronium bromide (Pavulon®), and 1.4 gram potassium chloride were administered intravenously.

Animals receiving the inventive PCA calcium phosphate demonstrated complete healing at three months. The test bones were then dissected from the animal and tested for strength. Preliminary results indicated that the inventive PCA calcium phosphate was resorbed and ossified to produce bone equal to or better than autologous implants in less than three months.

EXAMPLE 30

The purpose of this study was to evaluate resorption, ossification and biocompatibility of two formulations of the inventive PCA calcium phosphate in canine mandibular sites. Prehardened PCA calcium phosphate was implanted in a canine mandibular onlay model which additionally may be used as an augmentation model.

The test article was PCA calcium phosphate in two formulations, corresponding to Types 2 and 10 described in Example 11. The PCA calcium phosphate was pre-hardened in a moist environment at approx. 40° C. immediately prior to implantation. The control implants were 3 mm×4 mm cylinders of silicone and porous hydroxyapatite, respectively.

Two adult female hound-type dogs (20 to 25 kg) were used in the study. Both dogs received two control implants (1 of each) on the right side of the mandible and one each of the Type 2 and Type 10 PCA calcium phosphate formulations on the left (opposite) side.

Implantation was performed under full anesthesia and aseptic surgical conditions. The animals were premedicated with tranquilizers and atropine-type agents and induced with barbiturates. The animal's vital signs (temperature, heart rate, respiratory rate) were monitored before and throughout the procedure. The animals were tested for proper anesthetic depth by toe pinch and corneal stimulus. After obtaining adequate anesthesia, using aseptic technique, an incision was made in the skin over the midlateral ventral surface of the mandible and proximal neck (over the mandible lower edge). The soft tissue was deflected away and the bone was exposed. The periosteum over the outer mandibular surface was elevated and the bone surface was roughened with a burr or drill until it was rough and bloody in a shape to accept the cylindrical implants. The control articles and pre-hardened PCA calcium phosphate were placed into the defects. Two samples per animal per side were onlaid onto each outer mandible surface using this method (two experimental PCA calcium phosphate samples and two controls). The samples were placed about 1 cm to insure that they do not appose each other. The periosteum was closed first using 3.0 vicryl. The soft tissues were then closed in layers with 3-0 vicryl absorbable suture. The skin was closed with simple interrupted sutures of 5-0 nylon. The animals were allowed to heal for scheduled periods of time. One dog was sacrificed at 3 weeks and the other at 3 months and the test sites were removed for histology. All animals were euthanized and identifying marks were collected.

The implantation sites were prepared as undecalcified sections. Sections were evaluated for biointegration, biodegradation, and biocompatibility.

The results were as follows: At all time points excellent biocompatibility as observed. No giant cells and minimal macrophage were observed. There as only minimal reaction layer of only a few cells thickness at the base of the PCA calcium phosphate implants. This is significantly better than was observed for either of the controls.

At three weeks, the majority of the Type 2 material was resorbed. AT twelve weeks, the Type 2 was completely resorbed to the surface of the original bone. Additionally the bone in the socket was not fully differentiated.

The Type 10 samples demonstrated osseointegration with new bone ingrowth and cell migration into the implant. The implant itself was approximately 10% resorbed after twelve weeks.

The silicon control implant, which is not resorbable, displayed a mild to moderate foreign body reaction. Voids were unfilled at three weeks, but by twelve weeks were filled with fibrous tissue. The hydroxyapatite control implant showed no signs of resorption or osseointegration within the first twelve weeks.

This experiment confirms the excellent biocompatibility of the inventive PCA calcium phosphate. Additionally, a difference in resorption time between the two PCA formulations was observed, with a prolonged resorption time course for the sample in which the precursors were mixed/ground for a longer period of time (Type B).

The results also point out the slower resorption and ossification properties observed in the non-load bearing mandible implant site as compared to the rapidly ossifying load bearing applications of Example 29. Finally, the results demonstrate the need for slowly resorbing PCAs for proper osseointegration in augmentation plastic surgery.

EXAMPLE 31

This example demonstrates the effect of maintaining the hydrated precursor uncovered at room temperature.

The dry precursor was prepared as described in Example 11(b). The dry precursor was mixed with the indicated amount of water and tested for hardening and injectability through a 16 gauge needle after standing uncovered at room temperature for various time periods. The results are reported in Table 10.

TABLE 10

Paste Injectability after Standing at Room Temperature.

| sample wt (g) | water added (mL) | mixing time (s) | standing time (min) | room temp. (° C.) | injectability for 16 gauge needle | hardening; 30 min/ 37° C. |
|---|---|---|---|---|---|---|
| 1 | 0.8 | 20 | 10 | 25 | v. good | v. good |
| 1 | 0.8 | 20 | 20 | 24 | v. good | v. good |
| 1 | 0.8 | 20 | 30 | 25 | v. good | v. good |
| 1 | 0.8 | 20 | 40 | 25 | good | v. good |
| 1 | 0.8 | 20 | 50 | 24 | poor | v. good |
| 5 | 4.2 | 40 | 10 | 24 | v. good | v. good |
| 5 | 4.2 | 40 | 20 | 25 | v. good | v. good |
| 5 | 4.2 | 40 | 30 | 25 | good | v. good |
| 5 | 4.2 | 40 | 40 | 25 | poor | v. good |

These results demonstrate that a one gram sample may be stable as an injectable paste at ambient conditions for up to 45 minutes and that a 5 gram sample may be stable as an injectable paste for up to 30 minutes at ambient conditions (in air, 25° C).

EXAMPLE 32

Compressing precursors using hydraulic press. This example illustrates the method of preparing a pellet with a hydraulic press.

A Carver Laboratory Press is used. A specific amount of powder is measured by weight. The powder is then placed into the die set mold. The height or thickness is determined in part by the amount of material used in the mold. Once the material is in the die set, the mold is placed onto the hydraulic press. A desired load is set on the press. The material is then compressed for a specific amount of time. After the time has elapsed, the resulting pellet is expelled from the die set into a holding container.

A 0.5 g sample, ID=AB com1, from lot AB971002 was compressed at 500 psi (pounds per square inch) for 5 minutes in the Carver Laboratory Press. The physical aspects of the resulting pellet were diameter=13 mm, height=3 mm, and the density was 1.27 g/cm3. The mechanical strength was described as hard and capable of being broken by hand. After FTIR analysis, the pellet was 70% PCA in wet tissue, 90% PCA in 20 ml distilled water, and 100% PCA in carbonated buffered solution (CO3–20.2 mol). A second sample of 0.5 g, ID=ABcom2, from lot AB971002 was compressed at 4700 psi for 5 minutes in the Carver Laboratory Press. The pellet had the following results: diameter=13 mm, height=2 mm, and the density is 1.99 g/cm3. The mechancial strength was described as very hard and capable of being broken by hand. When the pellet was incubated at 37 C for 60 hours and analyzed through FTIR analysis, the following results were found: 60% PCA in wet tissue, 60% PCA in 20 ml distilled water, and 60% PCA in carbonated buffered solution (CO3–20.2 mol).

EXAMPLE 33

Compressing precursors using hand-held press. This example demonstrates the method of preparing a pellet with a hand-held press.

A Perkin Elmer Quick Press is used. Pellets 7 mm in diameter are made using the selected die sets in conjunction with the Quick Press. Other die sets of various diameters can also be used depending on the desired measurements. The surface of the pellet can be flat or rounded, depending on the shape of the mold. The sample is loaded into the selected die mold. As the amount of sample increases, the thickness of the pellet also increases. Next, a reference position is selected from the various manual positions set on the top of the Quick Press. The die set is placed in position in the Quick Press. A steady pressure is applied to the handle of the Quick Press for a selected amount of time. Once the time has expired, the pellet is removed from the mold by removing the bottom cap from the die set and applying pressure to the top die in order to expel the pellet from the die set.

A 0.08 g sample, ID: AB com3, of AB from lot AB971002 was measured into the 7 mm diameter die set. The Quick Press manual position was set at 20 and compressed for 1 minute. The resulting pellet had a diameter of 7 mm and a height of 1.5 mm; the density was 1.39 g/cm3. A second sample, ID: AB com4, of 0.1 g of AB from lot AB971002 was measured into the 7 mm diameter die set. The manual position was set at 20 and compressed for 30 seconds in the Quick Press. A resulting pellet was formed with a diameter of 7.0 mm and height of 2.0 mm; the density was 1.23 g/cm3.

EXAMPLE 34

Behavior of PCA Pellets with Different Media. This example describes the behavior of PCA calcium phosphate pellets in different medias.

The four kinds of media chosen were: (–MEM (Minimum Essential Medium); TBS (Tris Bovine Serum: 50 mM of Tris+150 mM of NaCl); (–MEM +FBS (Fetal Bovine Serum 10%); and Complete Media (immersion for 2 h in TBS at 37 C and subsequent immersion into the (–MEM+FBS).

A 0.3 g sample of mixed precursors ACP and DCPD was compressed for one minute at 7 tons using the Carver Laboratory Press. The resulting pellet (a) had a diameter of 12 mm and a height of 1 mm. The pellet was put into 10 ml of distilled water at 37° C. for 30 minutes. After incubation, the pellet was put in the 6 ml of different media at 37° C. for 24 and 48 hours.

A second 1 g sample of mixed precursors ACP and DCPD was combined with 0.8 ml of distilled water. The mixture was rolled into a ball and dropped into 10 ml distilled water at 37° C. for 30 minutes. The ball was then ground using a mortar and pestle to obtain a fine powder. The powder was pressed for one minute at 7 tons using a Carver Laboratory Press. The resulting pellet (b) had a diameter of 12 mm and a height of 1 mm. The pellet was then put into the different media at 37 C for 24 and 48 hours.

The pH of the solution of media was measured (at 25(C) at different times of 0, 24, and 48 hours after incubation at 37° C. The results of this study are displayed in Table 11.

TABLE 11

| Sample Prep- | pH of Solution | | | | | | | | | | | |
|---|---|---|---|---|---|---|---|---|---|---|---|---|
| | α-MEM | | | TBS | | | α-MEM + FBS | | | Complete | | |
| aration | 0 h | 24 h | 48 h | 0 h | 24 h | 48 h | 0 h | 24 h | 48 h | 0 h | 24 h | 48 h |
| a | 7.6 | 8.1 | 7.9 | 7.5 | 7.0 | 6.8 | 7.5 | 7.7 | 8.2 | 7.6 | 7.9 | 7.9 |
| b | 7.3 | 7.3 | 7.1 | 7.3 | 6.5 | 6.0 | 7.4 | 7.5 | 7.5 | 7.5 | 7.5 | 7.3 |

EXAMPLE 35

Reacting precursors, lyopholizing, crumbling, compressing. This example illustrates how a pellet is formed from PCA calcium phosphate paste.

PCA is made using ACP and DCPD, as the promoter. Saline is used as the biologically suitable aqueous medium. The prepared PCA paste is then lyophol hardened in vitro at 37° C. and subsequently lyopholized. The hardened PCA material is then crumbled by hand. Once crumbled, the PCA material is formed into a pellet by methods described in Examples 32 and 33.

EXAMPLE 36

Shaping, hardening, lyopholizing without grinding. This example shows how a pellet is formed from PCA calcium phosphate paste.

ACP and DCPD are selected as the precursors. An appropriate amount of Saline is used to make a PCA paste. The PCA paste is shaped into the desired form. It is then incubated at 37° C. in vitro for 30 minutes. The hardened object is then lyopholized.

EXAMPLE 37

In vivo experiments comparing the methods. This example compares the methods of producing the pellets through in vivo experimentation.

Pellets are made according to Example 32. Two pellets are implanted into a dog femur. The animals are sacrificed and the implantation sites are analyzed for remaining residual material at time points of 3, 4 and 6 weeks. At each time point, decalcified and undecalcified slides of the implantation site are prepared and stained. These slides are histomorphometrically analyzed to determine the similarity of the prepared pellets to that of PCA calcium phosphate paste.

EXAMPLE 38

Incorporation of a filler or binder. This example demonstrates the use of a filler to study plastic flow, with particular interest in the effect of tensile strength in the pellet.

A compressible sugar is used as a filler in conjunction with pellet production. The sugar is mixed with the precursors ACP and DCPD in a ratio of 1:1:1 before compression. The pellet is produced according to Example 33 with modifications in the duration of the total compression cycle and the duration of the maximum compressive force. The effectiveness of the sugar filler is measured by comparing the tensile strength of the pellets. The equation used to compute tensile strength is:

$$\sigma_0 = 2F/\Pi dt,$$

where $\sigma_0$ is the tensile strength, F is the force needed to cleave the tablet, d is the diameter of the pellet, and t is the tablet thickness or height.

EXAMPLE 39

Delivery of a vaccine in a pellet. This example explains how the pellet is used as a delivery vehicle for a vaccine.

Keyhole limpet hemocyanin is prepared at a concentration of 0.5 mg/ml in phosphate buffered saline pH 7.0. 0.8 ml of this solution is added to 1 g of a 1:1 mixture of activated ACP and DCPD . . . and mixed into a putty. The prepared PCA putty is then lyopholized. The dry material is milled for 10 minutes into a powder using a SPEX 8510 laboratory mill with a SPEX 8505 alumina ceramic grinding chamber. The powdered PCA is then prepared in a pellet as described in Example 32. A pellet formed by Example 32 is implanted subcutaneously in a rat. The process is repeated on a monthly basis for four months. Blood samples are taken on a regular basis and anti-Keyhole limpet hemocyanin antibody titers are determined by ELISA.

EXAMPLE 40

This example describes the preparation of PCA calcium phosphate using alternative second calcium phosphate sources. Both pre-hardened PCA calcium phosphate and crystalline hydroxyapatite reacted with reactive amorphous ACP to produce a PCA calcium phosphate.

(a) Poorly crystalline HA is prepared as described in U.S. Ser. No. 08/554,817 filed Nov. 7, 1995, incorporated herein by reference, using only carbonate as an inhibitor (no $Mg^{++}$ or pyrophosphate). The resultant powder was then lyophilized.

(b) Hydroxyapatite was obtained in powder form from Aldrich Chemicals (#28,939-6; lot 00325AQ).

Each of the two powders was mixed 1:1 with reactive amorphous calcium phosphate, prepared as described in Example 5 and mixed with water. Both mixtures hardened within 30 minutes at 37° C. and IR spectra of the reaction products were substantially the same as that of the PCA calcium phosphate produced according to Example 8.

EXAMPLE 41

This example describes the preparation of particulate PCA calcium phosphate which may be used in the composites of the invention.

Reactive amorphous calcium phosphate and DCPD are prepared as described in Examples 5 and 8 and are used to prepare poorly crystalline hydroxyapatite as described in Example 8. The hardened PCA calcium phosphate is lyophilized overnight and pulverized in a grinder and then passed through one or more sieves to obtain a desired particle size. Particles are then introduced into a PLGA. A variety of composite matrices are prepared as follows:

(a) 25 $\mu$m average particle size PCA calcium phosphate (10% wt/wt) in PLGA;

(b) 25 $\mu$m average particle size PCA calcium phosphate (5% wt/wt) in PLGA;

(c) 100 $\mu$m average particle size PCA calcium phosphate (5% wt/wt) in PLGA; and (d) 200 $\mu$m average particle size PCA calcium phosphate (5% wt/wt) in PLGA.

The composites prepared as above are placed intramuscularly in a rodent and resorption rates determined according to Example 16 to identify composites suitable for use in resorbable bioceramic composites.

EXAMPLE 42

This example describes the preparation and testing of resorbable PCA calcium phosphate composites.

A PCA calcium phosphate/poly(lactide) composite paste is prepared as described in Example 13 or Example 41. The paste is packed into molds in the shape of intermedulary nails, support plates, and screws. The molds are heated to 37° C. for three hours in a moist environment and the hardened objects are removed from the mold. The composite objects are implanted into animal models according to the procedure set forth in Example 19, in all cases being sure to contact the object with bone forming cells. Composites which are found to be fully resorbed and ossified in less than 6 months are suitable for use as bioresorbable bioceramic composite implants.

EXAMPLE 43

This example describes a resorbable composite for use as a bone filler or cement. A PCA calcium phosphate/dextran composite may be prepared by first preparing the paste as described in Example 8. The paste may be well mixed with 10% vol/vol polydisperse dextran, hardened in a moist environment and shown to have improved strength and compressibility. The hardened composite may be then introduced into a fracture site in an animal model according to Example 19. The time for resorption and reossification are determined. Screening according to Example 29 is used to determine the suitability of the composite as a resorbable bioceramic implant.

EXAMPLE 44

This example describes the coating of PCA calcium phosphate particles with a biodegradable outer coating. Particles prepared in this way resorb and/or ossify with an initial delay period as compared to PCA calcium phosphate alone.

PCA calcium phosphate particles may be prepared as described in Example 8. The particles may be prepared in a series of homogeneous lots with average particle sizes in the range of 60–100 microns according to the method used in Example 11. These particles may be then uniformly dip coated with poly(lactide). The coated particles are placed intramuscularly in order to evaluate the resorption kinetics, which may be delayed as compared to uncoated particles.

EXAMPLE 45

This example describes the use of a PCA calcium phosphate/hydroxyapatite composite to produce new bone. This form of bone is useful in augmentation therapy.

Crystalline hydroxyapatite may be prepared or obtained as 50–200 micron particles. These particles may be introduced into a PCA calcium phosphate paste at approximately 1 to 50 wt % and may be well mixed. The resultant composite paste may be formed into the desired shape, seeded with bone forming cells and implanted adjacent to cortical bone and fixed by suturing and soft tissue approximation. The composite may also be seated on a recipient bone which has been surgically fashioned according to the method of Example 19. After three months, the implant site may be examined as in Example 19 to establish that the new bone impregnated with particulate hydroxyapatite is formed in the shape of the formed implant.

EXAMPLE 46

This example describes the formation of a PCA calcium phosphate composite with a lubricant.

PCA calcium phosphate paste may be prepared according to Example 8. Silicone oil may be mixed with the paste at a concentration in the range of 0.1 to 30 wt %. Before the hardening reaction occurs, the paste may be injected through a 16–22 gauge needle and found to have significantly improved injectability as compared to an untreated paste.

EXAMPLE 47

This example demonstrates the use of a PCA calcium phosphate composite to embed an object in the recipient's bone. In addition to placement of anchoring devices, similar approaches can be used to embed almost any desired agent into a recipient's bone, including but not limited to support rods and fibers, imaging agents and friction reducing substances such as teflon plates.

A dacron loop approximately 1 mm in diameter may be formed on a 2 cm dacron suture. A knot may be placed within the suture approximately 2 mm from the loop. The suture may be then trimmed at the knot, leaving a loop with a 2 mm knotted tail. A 1 mm diameter hole may be drilled approximately 3 mm into a recipients's bone. The knotted end of the suture may be placed within the hole and the hole may be then filled with PCA calcium phosphate paste. After six months, suture site is evaluated for resorption of the PCA material in order to evaluate the composite's suitability as a resorbable bioceramic composite.

The procedure may be repeated in a second subject with the following modification. Following placement of the knotted suture within the hole, a prehardened PCA calcium phosphate plug may be wedged securely into the hole, thereby mechanically securing the suture in place. The hole may be then sealed with poorly crystalline hydroxyapatite paste. After six months, suture site is evaluated for resorption of the PCA material in order to evaluate the composite's suitability as a resorbable bioceramic composite. (two experimental PCA calcium phosphate samples arid two controls). The samples were placed about 1 cm to insure that they do not appose each other. The periosteum was closed first using 3.0 vicryl. The soft tissues were then closed in layers with 3-0 vicryl absorbable suture. The skin was closed with simple interrupted sutures of 5-0 nylon. The animals were allowed to heal for scheduled periods of time. One dog was sacrificed at 3 weeks and the other at 3 months and the test sites were removed for histology. All animals were euthanized and identifying marks were collected, The implantation sites were prepared as undecalcified sections. Sections were evaluated for biointegration, biodegradation, and biocompatibility.

The results were as follows: At all time points excellent biocompatibility was observed. No giant cells and minimal macrophage were observed. There was only minimal reaction layer of only a few cells thickness at the base of the PCA calcium phosphate implants. This is significantly better than was observed for either of the controls.

At three weeks, the majority of the Type 2 material was resorbed. At twelve weeks, the Type 2 was completely resorbed to the surface of the original bone. Additionally the bone in the socket was not fully differentiated.

The Type 10 samples demonstrated osseointegration with new bone ingrowth and cell migration into the implant. The implant itself was approximately 10% resorbed after twelve weeks.

The silicon control implant, which is not resorbable, displayed a mild to moderate foreign body reaction. Voids were unfilled at three weeks, but by twelve weeks were filled with fibrous tissue. The hydroxyapatite control implant showed no signs of resorption or osseointegration within the first twelve weeks.

This experiment confirms the excellent biocompatibility of the inventive PCA calcium phosphate. Additionally, a difference in resorption time between the two PCA formulations was observed, with a prolonged resorption time course for the sample in which the precursors were mixed/ground for a longer period of time (Type B).

The results also point out the slower resorption and ossification properties observed in the non-load bearing mandible implant site as compared to the rapidly

EXAMPLE 48

Efficacy Study of PCA in the Canine Alveolar Augmentation/Tooth Socket Model. This example demonstrates the use of the inventive PCA to restore bone tissue in an extracted canine tooth pocket.

The animals are premedicated with tranquilizers and atropine-type agents and induced and maintained with barbiturates. The animal's vital signs (temperature, heart rate, respiratory rate) are monitored before and throughout the procedure. The animal is then tested for proper anesthetic depth by toe pinch and corneal stimulus.

After obtaining adequate anesthesia, the gingival soft tissue is gently deflected away form the periphery of each premolar. The premolars are drilled in half with a slow speed dental drill and saline irrigation from the oral surface of the tooth to the lower surface between the roots. Each tooth half is then firmly grasped with extraction forceps and gently but firmly rotated until the tooth attachments are broken. The halves of each tooth are then removed. Bleeding is stopped by pressure and time. All premolars are extracted as described. After tooth removal and before PCA calcium phosphate placement, the lingual to buccal alveolar thickness is measured and recorded in at least 3 locations; these measurements are repeated after PCA calcium phosphate placement and at the time of necropsy and are used as a measure of bone ingrowth.

PCA calcium phosphate is prepared as Type 10 as described in Example 11. The empty tooth sockets/alveoli are located along one side of the mandible in the spaces formerly occupied by the premolar teeth. All dogs are implanted with PCA calcium phosphate in one side of the mandible and the opposite side remain untreated as unfilled controls. The gingival soft tissues are then closed in layers with 3-0 suture. After the surgical procedure the animals are monitored until they are stable.

The animals are allowed to heal for scheduled periods of time. Two dogs are sacrificed at 3 weeks, and two dogs are sacrificed at 2 months.

All animals are euthanized with a commercially prepared product used for euthanasia (such as sodium pentobarbital), and the mandibles and identifying marks are then collected and preserved in 10% neutral buffered formalin or another suitable fixative for decalcified and undecalcified bone sections. Mandibles are measured as described above and radiographed. The test sites thereafter are removed for histology.

The implantation sites are prepared as decalcified and undecalcified sections. Sections are evaluated for biointegration, biodegradation, and biocompatibility.

Figure 26:
FIG. 26 is a photomicrograph of a canine tooth socket defect that was treated with the PCA calcium phosphate of the present invention (magnification 4×; undecalcified, Light Green Basic Fuchsin)

A similar procedure was performed on a single dog. The implant was shown to bioresorb and to exhibit osseointegration within four weeks. FIG. 26 is a photograph of a histological slide of the tooth socket implant site four weeks after surgery demonstrating the extent of bone ingrowth into the socket. The large arrows indicate the boarder between the natural bone 1 and implant site 2. Note the extensive ingrowth of bone tissue at site 2. The gingival tissue is indicated at 3.

EXAMPLE 49

Osteoporotic Spinal Chord. This example demonstrates the procedure used for the treatment of osteoporatic vertebra.

Figure 27:
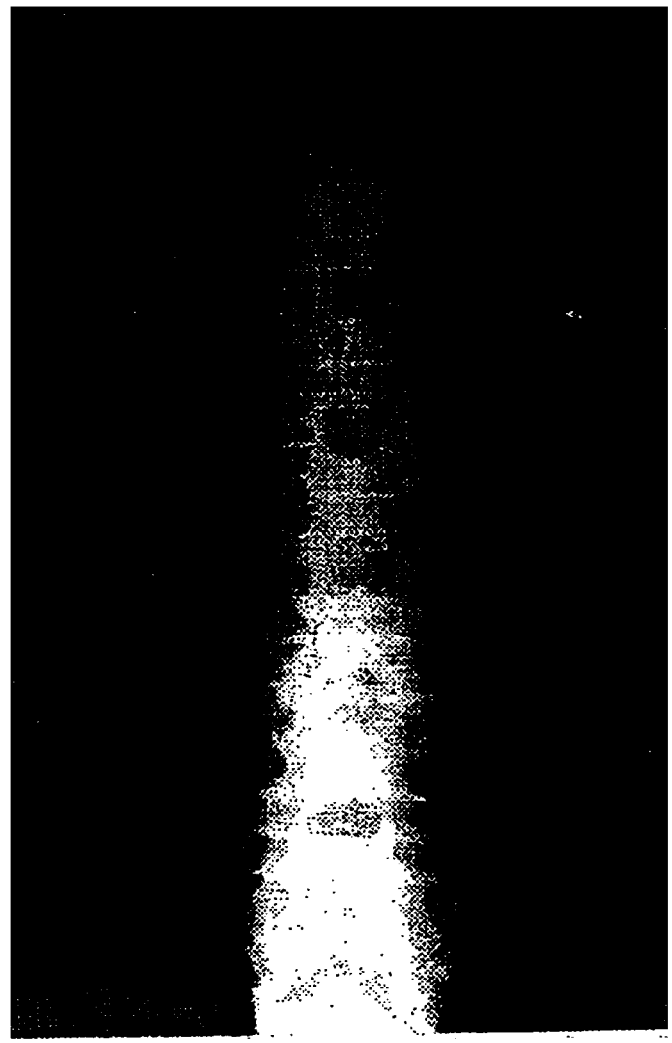
FIG. 27 is an X-ray photograph of a human cadaver osteoporotic spinal showing placement of needle prior to injection of PCA calcium phosphate.
Figures 28A, 28B:
FIG. 28 is a photograph of the top view of an individual vertebra of a human cadaver before injection of the PCA calcium phosphate (FIG. 28a) and after injection (FIG. 28b).

A spinal cord was obtained from the cadaver of an osteoporotic patient. Injectable PCA was prepared as Type 10 described in Example 11 using 1.5 mls of water per gram PCA as a hydrating agent. A 16 gauge bone biopsy needle (a Quantico bone needle is also useful for this purpose) was inserted into the trabecular vertebral bone (FIG. 27). A second 16 gauge needle affixed to an empty 50 cc syringe was inserted into the opposite side of the same vertebrae. Needle location was confirmed by X-ray (FIG. 27). Following confirmation of needle location, a syringe containing freshly hydrated PCA was affixed to the bone biopsy needle. PCA calcium phosphate was slowly injected from syringe with the biopsy needle simultaneous with slowly withdrawing the needle and applying gentle suction through the 50 cc syringe. The injected PCA can be seen as an electron dense area within the vertebrae in the X-rays in FIG. 28*b*, as compared to the osteoporotic vertebrae before implantation (FIG. 28*a*). These results confirm the injectability of the inventive PCA calcium phosphate paste into the spinal cord of an osteoporotic patient.

EXAMPLE 50

Canine anterior lumbar interbody fusion. This example describes the use of PCA calcium phosphate in the fusion of canine spinal vertebrae.

Animals were anesthetized, positioned in the right lateral decubitus position, shaved from anterior to posterior midline, extending form mid thorax to the pelvis. Following sterile prep and drape, a standard left retroperitoneal approach to the anterior lumbar spine was performed, with exposure of the L3–L6 vertebrae. The segmental vessels overlying L4 and L5 were ligated and divided, allowing anterolateral exposure of the L3–4, L4–5 and L5–6 discs. Anterior discectomies were performed at each level with the endplate prepared parallel and to bleeding subchondral bone using a parallel-paired-bladed oscillating saw (Aesculap). Following discectomy, a cylindrical titanium cage containing either PCA calcium phosphate or autologous bone or an unfilled cage was inserted into each disc space. Autogenous iliac crest bone graft was harvested from the left anterior iliac crest through a separate incision just prior to its packing into the cage and insertion into the disc space. After all three cages were inserted, internal fixation was applied using 4.5 mm vertebral body screws and a 6 mm diameter longitudinal rod from L3 to L6. Closure of the abdominal wound and iliac crest graft site was then done in layers using absorbable sutures and skin staples.

Dogs are sacrificed at two and twelve weeks and the histology of undecalcified sections are examined for evidence of new bone growth and vertebral fusion. Upon visual inspection on explant, the spinal cords using the PCA calcium phosphate of the invention appeared fused.

OTHER EMBODIMENTS

It will be understood that the foregoing is merely descriptive of certain preferred embodiments of the invention and is not intended to be limiting thereof. The following claims cover all of the generic and specific features of the invention herein described in the text and accompanying drawings.

What is claimed is:

1. A self-hardening calcium phosphate composite, comprising:

an amorphous calcium phosphate;

a second calcium phosphate having a calcium to phosphorous atomic ratio (Ca:P) of less than or equal to 1.67, wherein the amorphous calcium phosphate and the second calcium phosphate in combination have a calcium to phosphorous atomic ratio in the range of 1.1 to 1.9;

a supplemental material, said supplemental material comprising demineralized bone matrix; and a carrier fluid in an amount sufficient to form a paste or putty.

2. The composite of claim 1, wherein the amorphous calcium phosphate and the second calcium phosphate in combination have a calcium to phosphorous atomic ratio (Ca:P) of less than 1.5.

3. The composite of claim 1, wherein the amorphous calcium phosphate has a calcium to phosphorous atomic ratio (Ca:P) of about 1.55 to 1.65.

4. The composite of claim 1, wherein the second calcium phosphate is selected from the group consisting of calcium metaphosphate, dicalcium phosphate dihydrate, heptacalcium decaphosphate, tricalcium phosphate, monetite, calcium pyrophosphate dihydrate, hydroxyapatite, calcium deficient hydroxyapatite, octacalcium phosphate, and calcium pyrophosphate.

5. The composite of claim 4, wherein the second calcium phosphate comprises dicalcium phosphate dihydrate.

6. The composite of claim 5, wherein the dicalcium phosphate dihydrate has an average grain size of less than 95 microns.

7. The composite of claim 6, wherein the dicalcium phosphate dihydrate has an average grain size of about 35–45 microns.

8. The composite of claim 1, wherein the amorphous calcium phosphate and the second calcium phosphate are present in proportions ranging from 5:1 to 1:5 wt/wt, respectively.

9. The composite of claim 1, wherein the carrier fluid is selected from the group consisting of pH buffered solution, saline solution, tissue culture medium and serum.

10. The composite of claim 1, wherein the carrier liquid is present in an amount in the range of about 0.5 mL to about 2.0 mL liquid per gram calcium phosphate.

11. The composite of claim 1, wherein the supplemental material comprises 1–50 vol % of the composite.

12. The composite of claim 11, wherein the supplemental material comprises 1–20 vol % of the composite.

13. The composite of claim 1, wherein the supplemental material is in particulate form.

14. The composite of claim 1, wherein the supplemental material is in fiber form.

* * * * *

UNITED STATES PATENT AND TRADEMARK OFFICE
CERTIFICATE OF CORRECTION

PATENT NO. : 6,953,594 B2  Page 1 of 1
APPLICATION NO. : 09/993739
DATED : October 11, 2005
INVENTOR(S) : Lee et al.

It is certified that error appears in the above-identified patent and that said Letters Patent is hereby corrected as shown below:

Column 1, Line 36, replace "stiochiometric" with --stoichiometric--.

Column 38, Line 42, replace "cry stallization piomoting" with --crystallization promoting--.

Column 40, Line 23, replace "implait" with --implant--.

Column 41, Line 4, replace "th" with --the--.

Column 45, Line 12, replace "phosplate" with --phosphate--.

Column 51, Line 22, replace "ambulator," with --ambulatory--.

Column 57, Line 31, replace "mechancial" with --mechanical--.

Signed and Sealed this

Twenty-seventh Day of March, 2007

JON W. DUDAS
*Director of the United States Patent and Trademark Office*